(12) United States Patent
Ishiwata et al.

(10) Patent No.: US 6,962,984 B2
(45) Date of Patent: Nov. 8, 2005

(54) IGA NEPHROPATHY-RELATED DNA

(75) Inventors: Tetsuyoshi Ishiwata, Tokyo (JP); Mikiko Sakurada, Tokyo (JP); Ayako Kawabata, Tokyo (JP); Satoshi Nakagawa, Tokyo (JP); Tatsunari Nishi, Tokyo (JP); Tetsuro Kuga, Yamaguchi (JP); Shigemasa Sawada, Tokyo (JP); Masami Takei, Saitama (JP); Kenji Shibata, Tokyo (JP); Akiko Furuya, Tokyo (JP)

(73) Assignee: Nihon University, Tokyo (JP)

( * ) Notice: Subject to any disclaimer, the term of this patent is extended or adjusted under 35 U.S.C. 154(b) by 88 days.

(21) Appl. No.: 09/730,559

(22) Filed: Dec. 7, 2000

(65) Prior Publication Data
US 2003/0207828 A1 Nov. 6, 2003

Related U.S. Application Data

(63) Continuation-in-part of application No. 09/090,672, filed on Jun. 4, 1998, which is a continuation-in-part of application No. PCT/JP97/04468, filed on Dec. 5, 1997.

(30) Foreign Application Priority Data

Dec. 5, 1996 (JP) .............................. 8-325763

(51) Int. Cl.[7] .......................... C12Q 1/68; C12N 5/00; C07H 21/02; C07H 21/04
(52) U.S. Cl. .................... 536/23.1; 536/23.5; 536/24.5; 436/6; 436/325
(58) Field of Search .............................. 536/23.1, 23.5, 536/24.5; 435/6, 325

(56) References Cited

U.S. PATENT DOCUMENTS 5,378,464 A  1/1995  McEver .................... 424/143.1

FOREIGN PATENT DOCUMENTS

| DK | 4238778 | 11/1992 |
| EP | 269072 | 6/1988 |
| EP | 915 156 | 5/1999 |
| WO | 99/26980 | 6/1999 |

OTHER PUBLICATIONS

Genbank entry M58511, Human iron-respnsive element binding protein Jul. 14, 1995.*
Rouault et al. PNAS 87: 7958–7962, Oct. 1990.*
Samaniego et al. JBC 269(49):30904–30910, Dec. 9, 1994.*
N89899, EMBL (Aug. 15, 1996) XP002238226.
Plant, Physiol, vol. 106 (1994), pp. 1241–1255.
Clin. Exp. Immunol., vol. 103 (1996), pp. 125–132.
Kidney International, vol. 2 (1996), pp. 571–577.
FEBS Letters, vol. 351 (1994), pp. 231–236.
Gerken, et al., May 23, 1995. Accession #L29874.
Podgorski, et al., 1989, Mol. Cell Biol. (9):3938–3950.
Adams, et al., Aug. 1993. WO9316178–A.
Gantt, Mar. 21, 1995. Accession # Z11508.
Soares et al., Apr. 13, 1994. Accession #T10350.
Lindr, et al., Jan. 1995. Accession #M14618.
Kraus, et al., Jun. 1991. WO9108214–A.
Alberts, et al., Molecular Biology of the Cell, Third Edition, Garland Publishing, 1994.
Ding, et al., 2000, J Exp Med., 191(2):213–223.
Database EMBL Online, "Human Cosmid LUCA22", pp. 1–12, (Oct. 10, 1996).
Database SWISSPROT Online, "LUCA15", pp. 1–3, (Oct. 1, 1996).
Lai Kar Neng, et al., "Increased mRNA encoding for transforming factor–βin CD4+ cells from patients with IgA nephropathy", Kidney International , vol. 46, No. 4, pp. 862–868, (1994).
Database EMBL 'Online!, Accession Nr. AA772278, Jan. 31, 1998 (XP00217919).
Database EMBL 'Online!, Accession Nr. AA634469, Oct. 31, 1997 (XP002175920).
Database EMBL 'Online!, Accession Nr. AA381126, Apr. 18, 1997 (XP002175921).
Toyabe, et al., "IgA nephropathy–specific expression of the IgA Fc receptors . . . ", Clin. Exp. Immunol, vol. 110, No. 2 (1997), pp. 226–232.
Duque, et al., "Interaction of IgA with Fcα Receptors of Human . . . ", J. Immunol., vol. 159 (1997), pp. 3474–3482.
Ichinose, et al., "Detection of crytokine mRNA–expressing cells in peripheral blood . . . ", Clinical and Experimental Immunology, vol. 103, No. 1 (1996), pp. 125–132.
Database EMBL 'Online!, Accession No. AL023657, May 22, 1998, XP–00219247.
Sayos, et al., Nature, vol. 395, No. 6701 (1998), pp. 462–469.

* cited by examiner

Primary Examiner—Joe Woitach
(74) Attorney, Agent, or Firm—Fitzpatrick, Cella, Harper & Scinto

(57) ABSTRACT

A novel DNA whose expression level fluctuates in leukocytes of IgA nephropathy patients in comparison with leukocytes of healthy persons, a process for isolating the DNA, a novel protein encoded by the DNA, an antibody recognizing the protein, methods for detecting the protein and the DNA, and methods of diagnosis and treatment of IgA nephropathy.

10 Claims, 4 Drawing Sheets

ANTISERA OF RATS IMMUNIZED WITH KLH-COMPOUND 1

ANTISERA OF RATS IMMUNIZED WITH KLH-COMPOUND 2

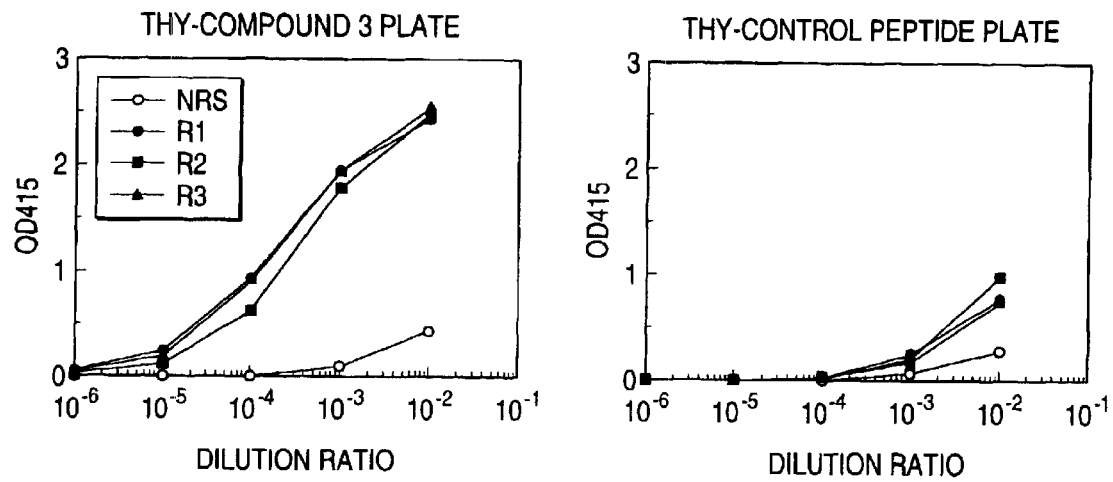
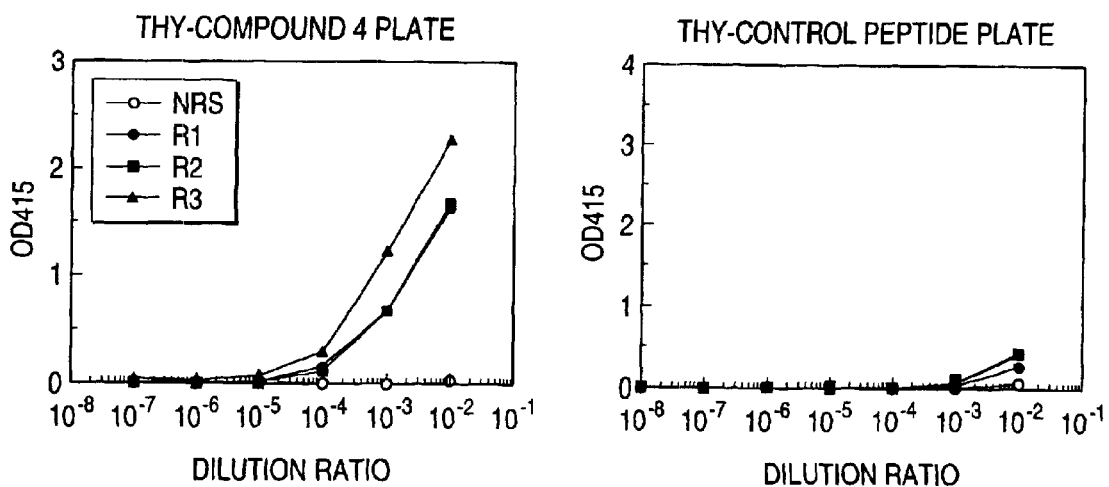

SEQUENCE LISTING

<160> NUMBER OF SEQ ID NOS: 121

<210> SEQ ID NO 1
<211> LENGTH: 4276
<212> TYPE: DNA
<213> ORGANISM: Homo sapiens
<220> FEATURE:
<221> NAME/KEY: CDS
<222> LOCATION: (53)..(742)

<400> SEQUENCE: 1

```
ttctaccgtt ttttccctgc tttctattcc aggtcagtct tcactgtttc cg atg gaa      58
                                                         Met Glu
                                                           1 gat gga ttc ttg gat gat ggc cgt ggg gat cag cct ctt cat agt ggc       106
Asp Gly Phe Leu Asp Asp Gly Arg Gly Asp Gln Pro Leu His Ser Gly
          5                  10                  15 ctg ggt tca cct cac tgc ttc agt cac cag aat ggg gag aga gtg gaa       154
Leu Gly Ser Pro His Cys Phe Ser His Gln Asn Gly Glu Arg Val Glu
 20                  25                  30 cga tat tct cga aag gtg ttt gta ggc gga ttg cct cca gac att gat       202
Arg Tyr Ser Arg Lys Val Phe Val Gly Gly Leu Pro Pro Asp Ile Asp
 35                  40                  45                  50 gaa gat gag atc aca gct agt ttt cgt cgc ttt ggc cct ctg att gtg       250
Glu Asp Glu Ile Thr Ala Ser Phe Arg Arg Phe Gly Pro Leu Ile Val
                  55                  60                  65 gat tgg cct cat aaa gct gag agc aaa tcc tat ttt cct cct aaa ggc       298
Asp Trp Pro His Lys Ala Glu Ser Lys Ser Tyr Phe Pro Pro Lys Gly
              70                  75                  80 tat gca ttc ctg ctg ttt caa gat gaa agc tct gtg cag gct ctc att       346
Tyr Ala Phe Leu Leu Phe Gln Asp Glu Ser Ser Val Gln Ala Leu Ile
          85                  90                  95 gat gca tgc att gaa gaa gat gga aaa ctc tac ctt tgt gta tca agt       394
Asp Ala Cys Ile Glu Glu Asp Gly Lys Leu Tyr Leu Cys Val Ser Ser
     100                 105                 110 ccc act atc aag gat aag cca gtc cag att cgg cct tgg aat ctc agt       442
Pro Thr Ile Lys Asp Lys Pro Val Gln Ile Arg Pro Trp Asn Leu Ser
115                 120                 125                 130 gac agt gac ttt gtg atg gat ggt tca cag cca ctt gac cca cga aaa       490
Asp Ser Asp Phe Val Met Asp Gly Ser Gln Pro Leu Asp Pro Arg Lys
                135                 140                 145 act ata ttt gtt ggt ggt gtt cct cga cca tta cga gct gtg gag ctt       538
Thr Ile Phe Val Gly Gly Val Pro Arg Pro Leu Arg Ala Val Glu Leu
            150                 155                 160 gcg atg gta atg gat cgg cta tac gga ggt gtg tgc tac gct ggg att       586
Ala Met Val Met Asp Arg Leu Tyr Gly Gly Val Cys Tyr Ala Gly Ile
        165                 170                 175 gat acc gac cct gag cta aaa tac cca aaa gga gct ggg aga gtt gcg       634
Asp Thr Asp Pro Glu Leu Lys Tyr Pro Lys Gly Ala Gly Arg Val Ala
    180                 185                 190 ttc tct aat caa cag agt tac ata gct gct atc agt gcc cgc ttt gtt       682
Phe Ser Asn Gln Gln Ser Tyr Ile Ala Ala Ile Ser Ala Arg Phe Val
195                 200                 205                 210 cag ctg cag cat gga gag ata gat aaa cgg gta agc ctt ata cta cat       730
Gln Leu Gln His Gly Glu Ile Asp Lys Arg Val Ser Leu Ile Leu His
                215                 220                 225 ttt gga aaa ttc tagaaatggt cctctaaatg tgtgattacc aatattagaa           782
Phe Gly Lys Phe
            230
```

-continued

```
cgggagcatt ttatgacaat aaagtgacag ctgacaattt tgcctataga gttaattatg      842
gtctataata catgaaataa tgtcctatga atttctttta tctttcagtt ttttgagtag      902
cctaatcaga acactacaat ttacttgagt taatttaatc ttctctaact tccattcaat      962
ctcaatccat ccgtccattc attcacttag tttgtaagtc attcaataaa tatttactga     1022
atcctttgtt ctgtgttata tcaagtatac aaacaggaat gcccttgagg tttcctgccc     1082
ttttttttgt ttgttttta atcctgggac atagggaaga cctcagcaag ccctatttct      1142
caatgaattg tactcacaga tttctttttt tttttttttt tcttttttcca cagccgccac    1202 ctctcaccga tttattcctt agcttggtgt ttcatgtatt caacaaacgt tttagtgctt     1262
agggcaagaa gttcctgtcc tcatgagttt atttcctagc agatagaact gtatcacttg     1322
ccagtactac tcagagtgtg gcctgtggac tgacctccag tctgtaaact tagtttgtag     1382
tgagatagga atttagacca gaatgtgtaa tcaaccacat tactgggcac aatgtttggt     1442
ccagctggcg attttttttt catagaaagc ctttattgat gagggaagca atatattgat     1502
ttatattttg gggtcacctt tttatttcat ggcacactgg cactttcatg catgctgact     1562
ttgatatcca tcactctgag gcattgtgct aaaatagatt gatttatcg tgttgttctc     1622 aattcaagat gtaaaaatca tcaagtcagt agcagttttt gcttttatg tttcatgtca     1682 tgtacagtct acttcactgg cagtaaaaaa atttaagata gtggtggtca tcctacaaac    1742
tgtgaatcta ttaaagagaa aagtatctgt tctattctaa gcatggggga gggacaagat    1802
tagtatgtta acatgcctac tttgtttgtt tgagatggag tctctctccg tcacccaggc    1862
tggagtgcag tggtacagtc tcagctcact ccaacctctg cctcccgggt tcaagtgatt    1922
ctcctgcctt agcctcccga gtaggtggaa ttacaggcat ataccaccat gcccaacaaa    1982
tgtttgtatt tttagtggag acagggtttc accgtgttgg tcaggccagt ttcaaactcc    2042
tgacctcaag ggatccacct gcctcaccccc ctcaaagtgc tgggattaca ggcatgagcc   2102
acccaccatg cctggcctac ttggtttttt atgcacacta aaaatacct acatctcact     2162 gccttattcc aacataagtt tcagagctgt gggattggtc attagaaatt cagactgaat    2222
ttgtgttcct ctgcaatgaa atcctttgcc cagtgttcat gtcactctgt agacattatg    2282
gagcagccta gaggcagaa gcccagtgct ctccttatgc ctgctcttcc tgggcttcgt     2342
gacactcttc ttctccttt gtacttttat tttttagtt aaaaaatttt ttttagaggg      2402
agggtctcac tctgtcaccc aggctggagc acagaatcac aatcatgact cactgcatgt    2462
tcttctcctt ttgttcatgg ctaatcttgg tcaggattcc ttgtcagagc tgggtggcac    2522
cagtgctggt gacagcctgc tgtaagggag tttcagccat gaatctctcc agactaaaaa    2582
taaccagctc ttttctagct gatgaattaa taaccaggtg actgttaatg cttgaaaggt    2642
tcacatgaca ggttggccga tagaacgctg gaacaggccc agttttagaa attcacctct    2702 gactttaga ctcaggtgaa ccattcttac tgagaaagaa caaagcaggg ttttagactg     2762
tgaatcctat ggctgcatct tttttttttt tttaacagag ttccaggttt gtgattataa    2822
cccaacatgt gtacactata aatagaaacc acgagccagg cttttacga cagctcagaa     2882 tcttgtgacg cagtagtcag gcatcttcac accgacttga atattgaagt gcagttgtgt    2942
ggaacttgga tcatcttagt tgattttgtt taaattatga ttccacatat gacaaaaatc    3002
cagatccact aattaaaatg agggtttatg tctatgaata atctcctgtg ggtttaatct    3062
cataacattc tagtctaaac agttggcttc acttcatgat gtctgctcaa atccttttc     3122 cttttaaagga tgtttatttta ataagaaaaa aaatgtaaaa tgatagataa taaaagccctt  3182
```

-continued

```
actaggttct taaaagatga actatccata tttcagtaaa tgaataatta gtccttcctc    3242
tttgggcacc ttggaacaga ttcattcaga tagtgggtgg aaatgtacat gtatggtaag    3302
cattgctggc ctagtcactg aaaaatgtaa actcttattt ttgattgcag gtggaagtta    3362
agccatatgt cttggatgat cagctgtgtg atgaatgtca gggggcccgt tgtgggggga    3422
aatttgctcc attttctgt gctaatgtta cctgtctgca gtattactgt gaatattgct    3482
gggctgctat ccattctcgt gctggcaggg aattccacaa gccctggtg aaggaaggcg    3542 gtgaccgccc tcggcatatt tcattccgct ggaactaaag gataactgca gtgctcattt    3602
tcaggcctca gaataagtgc actcttctgt tcattctgac ccttcctca acctcttcac    3662 gctggcatgt ccttttgtag cagtctgtaa cttaactata gtaatgaa aagaatgacc    3722 tataatatag gtgttttgta gattcttgtg tcactgcaaa caatatgaac tccttttcg    3782 tattgccatc gggttgcatg gaagttttat tctcttgttt tgctggaaac caagaggatc    3842
caaacttcct gcaacatttt cttagaggag agagagaaat attaaagag aaatgaaaca    3902 atagagtatt ttgggttttt aattaaatta ttgttaataa tataacatat aagaatactt    3962
ttattaaaat aaccatgcaa caataacact atcggtctat ctgacagttt tccccccagg    4022
gaagtgcttt tgccttttcc tttcttttt tttttttc atctttttg ttctctctct    4082 tttttccatc ccttttaat ttttttaaca gcaatggagg aagttaacaa ttttaatgg    4142 aaagagcatg ttagagcaaa caaatgcata agcaagactg agcagcatta taattaattt    4202
tcagggtttt gaggctgaac ataatttcat tatccctcaa aaagttacca ccacatcaga    4262
aaaaaaaaaa aaaa                                                      4276

<210> SEQ ID NO 2
<211> LENGTH: 2689
<212> TYPE: DNA
<213> ORGANISM: Homo sapiens
<220> FEATURE:
<221> NAME/KEY: CDS
<222> LOCATION: (107)..(535)

<400> SEQUENCE: 2
gttggaggtt ctggggcgca gaaccgctac tgctgcttcg gtctctcctt gggaaaaaat     60
aaaatttgaa ccttttggag ctgtgtgcta aatcttcagt gggaca atg ggt tca       115
                                                    Met Gly Ser
                                                      1 gac aaa aga gtg agt aga aca gag cgt agt gga aga tac ggt tcc atc      163
Asp Lys Arg Val Ser Arg Thr Glu Arg Ser Gly Arg Tyr Gly Ser Ile
  5                  10                  15 ata gac agg gat gac cgt gat gag cgt gaa tcc cga agc agg cgg agg      211
Ile Asp Arg Asp Asp Arg Asp Glu Arg Glu Ser Arg Ser Arg Arg Arg
 20                  25                  30                  35 gac tca gat tac aaa aga tct agt gat gat cgg agg ggt gat aga tat      259
Asp Ser Asp Tyr Lys Arg Ser Ser Asp Asp Arg Arg Gly Asp Arg Tyr
                 40                  45                  50 gat gac tac cga gac tat gac agt cca gag aga gag cgt gaa aga agg      307
Asp Asp Tyr Arg Asp Tyr Asp Ser Pro Glu Arg Glu Arg Glu Arg Arg
             55                  60                  65 aac agt gac cga tcc gaa gat ggc tac cat tca gat ggt gac tat ggt      355
Asn Ser Asp Arg Ser Glu Asp Gly Tyr His Ser Asp Gly Asp Tyr Gly
         70                  75                  80 gag cac gac tat agg cat gac atc agt gac gag agg gag agc aag acc      403
Glu His Asp Tyr Arg His Asp Ile Ser Asp Glu Arg Glu Ser Lys Thr
     85                  90                  95
```

| | |
|---|---|
| atc atg ctg cgc ggc ctt ccc atc acc atc aca gag agc gat att cga<br>Ile Met Leu Arg Gly Leu Pro Ile Thr Ile Thr Glu Ser Asp Ile Arg<br>100                   105                      110                    115 | 451 |
| gaa atg atg gag tcc ttc gaa ggc cct cag cct gcg gat gtg agg ctg<br>Glu Met Met Glu Ser Phe Glu Gly Pro Gln Pro Ala Asp Val Arg Leu<br>                    120                           125                       130 | 499 |
| atg aag agg aaa aca ggt gag agc ttg ctt agt tcc tgatattatt<br>Met Lys Arg Lys Thr Gly Glu Ser Leu Leu Ser Ser<br>            135                         140 | 545 |
| gttctcttcc ccattcccac ctcagtccct aaagaacatc ctgattcccc cagtcttcaa | 605 |
| gcacatgaat tcagaatgaa aggtttgcca tggctaagga atgtgactct ttgaaaacca | 665 |
| tgttagcatc tgaggaactt tttttaaactt tgttttaggg acttttttttt ccttaggtaa | 725 |
| gtaatgattt ataaactcct tttttttttttt ttgactatag tcggttgcat ggttacttta | 785 |
| agcgtggaat caaatggagt ggcatttagt tcaggcggct tgttccttgc catggcaaag | 845 |
| tatcaagaag atccccaagt caagtcacat ttgtaaagct gcttcccaat ggctttgtc | 905 |
| acgcagtgtt gaagcagtgg gagagagatt cacctgttat aaaggaactg actaacacaa | 965 |
| gtatcccgtc tatatctgaa tgctgtctct aggtgtaagc cgtggtttcg ccttcgtgga | 1025 |
| gttttatcac ttgcaagatg ctaccagctg atggaagcc aatcaggttg cttcactcac | 1085 |
| caagtctaga tattcatgaa aatggaacaa gtctgtacaa ttttaaaaaa aggttgaagg | 1145 |
| agtggtttgt tccaaaggag tgactttttt ttaaaaaaaa aagctttgta tatattaaaa | 1205 |
| ttgatgttac tagaataagt acagtaccaa ggacttcatt atagaatttg ttctgccttt | 1265 |
| aaacatggct acctacctgg cagggctttg ttaactactg aatacctgtc tggtaatcac | 1325 |
| taaaacatct taatgtttcc ctttttttcta gtttgttata ttcctattat gtccattgag | 1385 |
| agtaagctta gtatatcaaa ctctccatt gacagtgaag agaacatagt gaaagtctgt | 1445 |
| ggcggcattt ttataagtaa ttccttattt ctgcctgaag accacaaagc ctcctggagg | 1505 |
| cgtaactgct cagaccggtc ttcagggaat atttaaggac ttagtggaat ttatgaacaa | 1565 |
| taagtctgat gagattagcc tgggagtggt gtcctgcagc tgtctaatct agttagagtg | 1625 |
| gcattaacat tctaatctcc ttgagaatgc cttttatagt ctgttcaaag caagtcattg | 1685 |
| atggttcttc gaggtagtgt taactgaagt gttcttcagt ttgtcaagat aatgttcagt | 1745 |
| gcttggcact taaataacat tttttgcaag aactccaagg cacattattg aatgccttta | 1805 |
| accaagtgca ttctgggaag tttgcttgac tcattatctt gcttttctgc agcattctgt | 1865 |
| gatttgagtc atccatgaat ccatgaataa agttacatt ctttgattgg taatattgcc | 1925 |
| atttataaca agactcacta atgagggtat cactttgact gactgatttg ttaaagtttt | 1985 |
| taagcctctc atttttcctaa cccagaaatc acagcctgat tttattaaaa gtagagcttc | 2045 |
| attcatttca taccatagat accatcctag taaatccaga acatatacaa ggttcatgtg | 2105 |
| agtctgcttt cttgacatga tagcattgtt tgatgcagtg gatatgtcag aatgactaac | 2165 |
| ctaggagttt aaaactccta agaaactaaa acctgtaaga catttaaaag tctccacaat | 2225 |
| tttaatgtat acaaagctat gttactgtgt aacacattac agttcaaatt cactccagaa | 2285 |
| ataaaaggcc agtaggatta gggactcact ggtagtttgg agtctcccag cacacatccc | 2345 |
| tcctagtggg atgatctatt cacatatctc ccagcttttt tattttttgct tctgtatatc | 2405 |
| acagtgagtg gatggcccctt cagctttttc tctcctggcc agacatgcag tcttgccttt | 2465 |
| agatatcgca gagacaaaat tcacagcatg tcttaaatct tccaggattt gcaagaacca | 2525 |
| aattgctcaa cagtatgtat gtttagaggg gttagactcc tttttaaaat ctggatatct | 2585 |

-continued

| | |
|---|---|
| aaccacctac ttaaatctgt ttgatagtgt caaaccaccc ccaccettga tcctcccacc | 2645 |
| cccaaaaaaa aaaaaaaaaa aaaaaaaaaa aaaaaaaaaa aaaa | 2689 |

<210> SEQ ID NO 3
<211> LENGTH: 2981
<212> TYPE: DNA
<213> ORGANISM: Homo sapiens
<220> FEATURE:
<221> NAME/KEY: CDS
<222> LOCATION: (1297)..(1608)

<400> SEQUENCE: 3

| | |
|---|---|
| cctctctctc tctttcacag agtcttgctc tgtcgcccag gctggagtgc agtggcacaa | 60 |
| tctcactgca agctccgcct cctgggttca cgccattctc ctgcctcagc ctcccaaata | 120 |
| gctgggacaa caggcacctg ccaccacgcc cggctaattt tttgtatttt tagtagagac | 180 |
| agggtttcac catgttagcc aggatggtct caatctcctg acctcgtgat ccacccgcct | 240 |
| cagcctccca aagtgctgag attacaggtg tgagccacca cgcccagcca catctttctt | 300 |
| tctttcttt tggttttgt tgttgtttg agacagggtc ttgctctgtc gccctggctc | 360 |
| acgtgaacct cccacctcag cctcccaagt agctgagacc acaggtgtga ccaccactc | 420 |
| ctgggtaatg tttgtatttt tttgtagaga tggggtttca ccgtgctgcc cagactgctc | 480 |
| tcaaactcct gggctcaagt gatccacctg ccttgacctc ctaaagtgct ggaattacag | 540 |
| gtgtgagcca ccgtgctcag ccgagtgtct ttcgtatgtt ttctgagcac gtggatttcc | 600 |
| atctctctgc attctctgtt catctcagcc tgtttgttcc attgagataa atgactttt | 660 |
| cttggtaact tagagtactt tgtgtatta caggttaatc ccttatcaat ttatatcagt | 720 |
| tgctgctatc tttctagga ttttctttt catttaaaa attacattgt tcaatgaac | 780 |
| agaatttta agttttaacg tagtccactt tgtccatttt ctttatgacc ggtgcattt | 840 |
| agggtcttgt ttaagaaatc gttctttatc ctgaggtcat aaagatagtc tactgtatt | 900 |
| tcttttaaga gctgaaaagg tgttttatat ttaatttatt tgggattggc ttttgtgtgg | 960 |
| tggggataag gatcacaatt ttatttcatt ttttttccac ttggttatgc cagtggcccc | 1020 |
| atttccatt tttgaatagt ctttctgtgc agaaaagact tcactagcag agaagtcctg | 1080 |
| agacttaccc ttcaaaaggc cccattcaca aggctagcac ttggcgtgca tctgagaacc | 1140 |
| tggatttggg ggtggttcct ataatgtggt gtatgctgaa cacccaccctt tccttctggg | 1200 |
| agtctggaat ttgggtatat gttggacaga ggctgcctaa gtgaccagct tcaacaacag | 1260 |
| ccctgggtgc tgggtcactc atgacccata gacaaa atg cca cac atg ttg tca | 1314 |
| | Met Pro His Met Leu Ser |
| | 1 5 |
| cag ctt att gct gga gga gtt agc aca tcc tgt gtg act gca ctg gga | 1362 |
| Gln Leu Ile Ala Gly Gly Val Ser Thr Ser Cys Val Thr Ala Leu Gly | |
| 10 15 20 | |
| gag gaa act ggt gcc tgg ttc cct gtg tat ttg tcc cac gcc tcc agt | 1410 |
| Glu Glu Thr Gly Ala Trp Phe Pro Val Tyr Leu Ser His Ala Ser Ser | |
| 25 30 35 | |
| ccc ttt gct gat ctc gtt ttt tgt cct ttt gct gag ata aat cac agc | 1458 |
| Pro Phe Ala Asp Leu Val Phe Cys Pro Phe Ala Glu Ile Asn His Ser | |
| 40 45 50 | |
| cag gag tat gac aat atg cgg ggt cct gtg agt cct cct aac aaa cag | 1506 |
| Gln Glu Tyr Asp Asn Met Arg Gly Pro Val Ser Pro Pro Asn Lys Gln | |
| 55 60 65 70 | |

```
ttc aat ctg ggg gtg atc ttt ggg atc ccc aac aac tgt cgt ttc ccc       1554
Phe Asn Leu Gly Val Ile Phe Gly Ile Pro Asn Asn Cys Arg Phe Pro
            75                  80                  85 act gat aat aaa ata act gag aag cag cta ttg ggc aat gtt ctg aac       1602
Thr Asp Asn Lys Ile Thr Glu Lys Gln Leu Leu Gly Asn Val Leu Asn
            90                  95                 100 tac cct tgaacattca tgtcttcatc tgaacatcca tctactaccc ctgattttt         1658
Tyr Pro cagtgcaggg tgcatatcct gtatcaccca ataaatggtc attgatcacc ataggaaagg    1718
aacagtgaaa gctccacggt ggtttggagg aaggtggcag gcattcagcg gtaacttttt    1778
tgagcagata gattttatgt tttgcaatg agtgaaataa attttcccat atctatttaa     1838
ggttggcaat cattatcttt ttatcatctt ggaacatttg gaattccttt aatatgttta    1898
gttaggaatt ttctaccttc ctcatcttgt ccgatagttt aaaatcccac agttattca     1958 cgggctcctc atacctgcct gtgtgatttc taacatgtca cgctatgcaa ccagttgctt    2018
ttacttgtag agtgtttctt taggtaatag cttattattg gttatgtgat tacagtgtgt    2078
taaagacagg tctgtagtta tgtaaaatgc cgtttctctg agtatcatgg tcatttccac    2138
atatttctct attcatgtat ttgtaagaat atatctattt ttgcagtatt ttatttattt    2198 atttttatttt atttttctgaa acggagcctt gttctgtcac ctaggctgga gtgcagtggt  2258
gtgatctcga ctcactgtga cctcccctc ccaggttcaa gcgattctcc cgcctcatcc     2318
tcccaagtca ttgggattac agtcacgtgc catgaagccc tgctaatttt ttgtattttt    2378
agtagagaca ggatttcacc atgttggcga tgctggtttc gaactcctgg tttcgaactc    2438
ctgacctcaa gtgatccacc tgcctcggcc tcccaaagaa ctgggattat gggcgtgaac    2498
caccacgcca ggtcagtttt gcagtgtttt aaatactgtt gtctttgaga ggagagaggc    2558
acgcacatag actatggtga ttaccatcat atactggaaa gtgcaaagtg tagcgcagtt    2618
aactgtgagc catctcatca aaccctaaca gatgtccat ttgtccataa aggggcttct    2678
gtcccataga aattcatgta cccaacctac tcttcaacca tgattttct ctgatggcct    2738 gtgtgaacag attaatggtg tccatctaat tccttcccca ctgggggaaa gcaaatcatc    2798
aggcccattg caaaaactgc tcttggttga gcttcctgcc ttaaatcata cccacagtga    2858
atggcgtccc tttatcaccg ctaatgactc tgacatctct ctccactcac atgtgagcct    2918
cctcagctct cgataaacaa gtctgtctcg gttcatttat tctacaaaaa aaaaaaaaa    2978 aaa                                                                 2981

<210> SEQ ID NO 4
<211> LENGTH: 1461
<212> TYPE: DNA
<213> ORGANISM: Homo sapiens
<220> FEATURE:
<221> NAME/KEY: CDS
<222> LOCATION: (282)..(680)

<400> SEQUENCE: 4
aattcggcac gagcagcttt ctagttggat taggcaacag aatcctttga aaatgtgtgt      60
gcacagacca ggtggctctc tgggccagtg tactctgaaa gatgtgtgtc ctggcctagc    120
tggttgagga aaagcagggc aagcctagcc aaatcacaca tcttgaacag ccctcattcg    180
ttatactaac tttcccacct tctggtgtgt ataggagata aagatggcag acgtgctatt    240
aggctgccaa tgggagtggg ctctgatatg gtctttcaaa t atg aat cac ccc tgg    296
                                            Met Asn His Pro Trp
                                              1               5
```

| | | | | | | | | | | | | | | |
|---|---|---|---|---|---|---|---|---|---|---|---|---|---|---|
| cat | gtg | tgt | ttc | ctg | ttt | aag | gtt | ctc | agg | tat | tac | cca | act | gca | cca | 344 |
| His | Val | Cys | Phe | Leu | Phe | Lys | Val | Leu | Arg | Tyr | Tyr | Pro | Thr | Ala | Pro |
| | | | 10 | | | | 15 | | | | 20 | | | | |

```
cat gtg tgt ttc ctg ttt aag gtt ctc agg tat tac cca act gca cca      344
His Val Cys Phe Leu Phe Lys Val Leu Arg Tyr Tyr Pro Thr Ala Pro
            10                  15                  20 ata tta aaa tgg aca cat acc gtg tca tgc agt tgg tgc cga agt gtt      392
Ile Leu Lys Trp Thr His Thr Val Ser Cys Ser Trp Cys Arg Ser Val
        25                  30                  35 tta agg gaa gtt gta ggc aat gtg agt tta tca gaa aac ttc acc ata      440
Leu Arg Glu Val Val Gly Asn Val Ser Leu Ser Glu Asn Phe Thr Ile
    40                  45                  50 tca gca ttt tgc cct gag ctt aca cca ttc cca gat caa ggt aca agc      488
Ser Ala Phe Cys Pro Glu Leu Thr Pro Phe Pro Asp Gln Gly Thr Ser
55                  60                  65 aca atg att tcc ttt ctt gaa aag ttc aac aaa agc aag aga gag aga      536
Thr Met Ile Ser Phe Leu Glu Lys Phe Asn Lys Ser Lys Arg Glu Arg
70                  75                  80                  85 ttg gag ttg atg ctg cat ttt tat tct gtg tta agt ctt gaa cct gct      584
Leu Glu Leu Met Leu His Phe Tyr Ser Val Leu Ser Leu Glu Pro Ala
                90                  95                  100 gtt gct gaa cat tgg tca ggg gaa ttt gag aag tgg aaa gtg ggc ttt      632
Val Ala Glu His Trp Ser Gly Glu Phe Glu Lys Trp Lys Val Gly Phe
                    105                 110                 115 ttt cac cct ttg aaa aga gag gat gga ttc ttc acc aga act gac att      680
Phe His Pro Leu Lys Arg Glu Asp Gly Phe Phe Thr Arg Thr Asp Ile
                120                 125                 130 taaaaaaagt cagcgtggca cgttttagta tgtgtggcag atctaaasag acaatatttt    740
gatctcagga gtgtttattc ttgaaccatt ttcagaactc taagatttga gaaataataa    800
aatattgacc atccttcaaa gagaaaaaca cagggcgatc tttggcatag cctgtcattt    860
tgctcacatt tcacttctct ctctccaact tcagagcccc tgctgtggaa caggtgctgt    920
gctgggtggc aggggaggtc tctggctttt ttttttttg atctccgtct taacatctag    980
cctactggag gaagtgtatt taatcatcca cttatctgtt aacaattatc tctgagggcc   1040
cgtcacattc agagaagatt ctaggttctc tacaagtatc ctctcactgt gtacatacta   1100
aatcaacatc ctgctggatt tcccccagac atctcccttc atcaccattg gagagtatcc   1160
tctaattgcc agcccctattc accatactca tctcatttga tctggagttt tctgagagtg   1220 accggggggtg ggatggacag gataaatttag caagagtgta taagtaaaat ctatataata  1280
aaagttatct ccctgtgccc cccatgatct attctttatg tagcagtctg aatgagattt   1340
tcagaaacaa gaaccacttt accttagtct cttcttcttc ttcttcttct tttcttttct    1400
ttttttttag tattatgggc aacagagcaa gacccagtct caggaaaaaa aaaaaaaaaa   1460
a                                                                    1461
```

<210> SEQ ID NO 5
<211> LENGTH: 3329
<212> TYPE: DNA
<213> ORGANISM: Homo sapiens
<220> FEATURE:
<221> NAME/KEY: CDS
<222> LOCATION: (637)..(1035)

<400> SEQUENCE: 5

```
ccaaagtgct gggattatag gcatgagcca ctgcgcccgg ccagaatacc ctatccttaa     60
acatgaattt aggggagggg aggacacaat tcaatctata acaactatca ctggctgatt    120
ttggcagagg cctgtggcct ccagtatttt gagggagctg agggccactg atctctccat    180
atgctctcaa catcatggga ctagtaggat gaaagcaagc ctcagaccag attctacctc    240
```

```
aagcaggcac acaaacattc atgcagcttc tacttggagc ctgatgaagt tcaaattgtt      300
tgtcctctga ggctctcttt gcatggaaat ttctcccatg acagatgaga agttctggg       360 gcagcattca gctttctagt tggattaggc aacagaatcc tttgaaaatg tctgtgcaca      420
gaccaggtgg ctctctgggc cagtgtactc tgaaagatgt gtgtcctggc ctagctggtt      480
gaggaaaagc agggcaagcc tagccaaatc acacatcttg aacagccctc attcgttata     540
ctaactttcc caccctctgg tgtgtatagg agataaagat ggcagacgtg ctattaggct      600
gccaatggga gtgggctctg atatggtctt tcaaat atg aat cac ccc tgg cat       654
                                        Met Asn His Pro Trp His
                                         1               5 gtg tgt ttc ctg ttt aag gtt ctc agg tat tac cca act gca cca ata      702
Val Cys Phe Leu Phe Lys Val Leu Arg Tyr Tyr Pro Thr Ala Pro Ile
         10                  15                  20 tta aaa tgg aca cat acc gtg tca tgc agt tgg tgc cga agt gtt tta      750
Leu Lys Trp Thr His Thr Val Ser Cys Ser Trp Cys Arg Ser Val Leu
     25                  30                  35 agg gaa gtt gta ggc aat gtg agt tta tca gaa aac ttc acc ata tca      798
Arg Glu Val Val Gly Asn Val Ser Leu Ser Glu Asn Phe Thr Ile Ser
 40                  45                  50 gca ttt tgc cct gag ctt aca cca ttc cca gat caa ggt aca agc aca      846
Ala Phe Cys Pro Glu Leu Thr Pro Phe Pro Asp Gln Gly Thr Ser Thr
 55                  60                  65                  70 atg att tcc ttt ctt gaa aag ttc aac aaa agc aag aga gag aga ttg      894
Met Ile Ser Phe Leu Glu Lys Phe Asn Lys Ser Lys Arg Glu Arg Leu
             75                  80                  85 gag ttg atg ctg cat ttt tat tct gtg tta agt ctt gaa cct gct ttt      942
Glu Leu Met Leu His Phe Tyr Ser Val Leu Ser Leu Glu Pro Ala Phe
                 90                  95                 100 gct gaa cat tgg tca ggg gaa ttt gag aag tgg aaa gtg ggc ttt ttt      990
Ala Glu His Trp Ser Gly Glu Phe Glu Lys Trp Lys Val Gly Phe Phe
            105                 110                 115 cac cct ttg aaa aga gag gat gga ttc ttc acc aga act gac att         1035
His Pro Leu Lys Arg Glu Asp Gly Phe Phe Thr Arg Thr Asp Ile
        120                 125                 130 taaaaaaagt cagcgtggca cgttttagta tgtgtggcag atctaaagag acaatatttt     1095
gatctcagga gtgtttattc ttgaaccatt tcagaactc taagatttga gaaataataa     1155
aatattgacc atccttcaaa gagaaaaaca cagggcgatc tttggcatag cctgtcattt     1215
tgctcacatt tcacttctct ctctccaact tcagagcccc tgctgtggaa caggtgctgt      1275
gctgggtggc aggggaggtc tctggctttt ttttttttgat ctccgtctta acatctagcc    1335
tactggagga agtgtattta atcatccact tatctgttaa caattatctc tgagggcccg     1395
tcacattcag agaagattct aggttctcta caagtatcct ctcactgtgt acatactaaa     1455
tcaacatcct gctggatttc ccccagacat ctcccttcat caccattgga gagtatcctc     1515
taattgccag ccctattcac catactcatc tcatttgatc tggagttttc tgagagtgac     1575
cgggggtggg atggacagga taatttagca agagtgtata agtaaaatct atataataaa    1635
agttatctcc ctgtgccccc catgatctat tctttatgta gcagtctgaa tgagattttc     1695
agaaacaaga accactttac cttagtctct tcttcttctt cttcttcttt tcttttcttt     1755
ttttttagta ttatggggat ctgtttctgt tgcccagggt ggagtgcagt ggtatgatct     1815
tggctcacag cagccttgaa ctcccgggct caagtggtcc tcctgcctct gcttccctag     1875
tagctaggac tgcaggtttg tgccaccaca cctggctaat tgaaaaaaga aattttttt      1935 caatagagac agtgtcttgc tatgtcccca ggctggtctc aaactcctgg cctcaagtga    1995
```

-continued

```
tcctcctgtc tcatcctccc aaagtgttgg aattacaggt gtgagctact atactcggcc      2055
agtacccttc tcaaaacact tcagcacttc ccattgcact tgggttgaaa ttcccaccac      2115
tcactgggc ccacaagact cttcaagact gaatccttgc tcaacattgt gacctgcccc       2175
ctaccacctg cagcctcact tgctgtgctc cagccatgtg gatcttcctc ctgtctctaa      2235
aactgcctca ggtcatttgc acctgctgtt cttcccaaag gctgtgtgat ttccatcagt      2295
cagtcttagc tcgtataccct ccttggagac acctcttctg accaaccagt ccaaagaatc     2355
tcctcttatc atgtcactct gtttttattta tttatttaga gatggagtct cgctctgtca     2415
cccaggctgg agtgcagtgg cgcgatctct gctcactgca agctccacct cctgggttca     2475
tgccgttctc ctgcctcagc ctcctgagta actgggacta tgggcaccca ccactacacc     2535
cggctaattt tttgtatttt tagtggggat ggggtttcac tgtgttagcc aggatggtct     2595
tgatctcctg accttgtgat ctgcctgcct ccacctccca aagtgtttta tttattttaa     2655
aggcatgtat cactctctga aaattagctt ctttcttctt tttccttgtt atcatccatt     2715
tccccgaacc agaatagaag ttcctgaggc cagaacttct gtctctctgc ccctcactat     2775
gtgtctctgg cacatacccc agtgcctgcc tgctctaaag taaaatctta gtaaatatta     2835
ctgttgacta aataaatgaa taaatccctt ttaatgcccc tttggaagtt gccaagtaaa     2895
gaataggatc ccttttttaag attacacttt tggctattga tctgtgtgtc tggaacaaga    2955
tacagtttga agatactacc atgggacatg acatcagttg agctgattaa ggttttagta     3015
ataagaatcc aggatgtgtc cggtgcggt gctcacgcct gtaatcctag cattttggga      3075
gaccgaggcg ggcagatcac gaggtcagca gtttgagacc agcctgacca acatggtgaa    3135
accccgtctc tactaaaaaa tacagaaatt agccgggtgt ggtggtgtcc acctgtagtc     3195
ctagctactc aggaggctgg ggcaggagaa tttcttgaac ccgggaggcg gaggttgcag     3255
tgagccgaga tcacaccagt gcactccagc ctgggcaaca gagcaagacc cagtctcagg    3315
aaaaaaaaaa aaaa                                                       3329
```

<210> SEQ ID NO 6
<211> LENGTH: 2276
<212> TYPE: DNA
<213> ORGANISM: Homo sapiens
<220> FEATURE:
<221> NAME/KEY: CDS
<222> LOCATION: (103)..(486)

<400> SEQUENCE: 6

```
ctgaactggg agtcaggtgg ttgacttgtg cctggctgca gtagcagcgg catctccctt       60
gcacagttct cctcctcggc ctgcccaaga gtccaccagg cc atg gac gca gtg        114
                                              Met Asp Ala Val
                                                1 gct gtg tat cat ggc aaa atc agc agg gaa acc ggc gag aag ctc ctg       162
Ala Val Tyr His Gly Lys Ile Ser Arg Glu Thr Gly Glu Lys Leu Leu
  5                  10                  15                  20 ctt gcc act ggg ctg gat ggc agc tat ttg ctg agg gac agc gag agc       210
Leu Ala Thr Gly Leu Asp Gly Ser Tyr Leu Leu Arg Asp Ser Glu Ser
                 25                  30                  35 gtg cca ggc gtg tac tgc cta tgt gtg ctg tat cac ggt tac att tat       258
Val Pro Gly Val Tyr Cys Leu Cys Val Leu Tyr His Gly Tyr Ile Tyr
             40                  45                  50 aca tac cga gtg tcc cag aca gaa aca ggt tct tgg agt gct gag aca       306
Thr Tyr Arg Val Ser Gln Thr Glu Thr Gly Ser Trp Ser Ala Glu Thr
         55                  60                  65
```

-continued

| | | |
|---|---|---|
| gca cct ggg gta cat aaa aga tat ttc cgg aaa ata aaa aat ctc att<br>Ala Pro Gly Val His Lys Arg Tyr Phe Arg Lys Ile Lys Asn Leu Ile<br>    70                      75                        80 | 354 |
| tca gca ttt cag aag cca gat caa ggc att gta ata cct ctg cag tat<br>Ser Ala Phe Gln Lys Pro Asp Gln Gly Ile Val Ile Pro Leu Gln Tyr<br>85                      90                        95                          100 | 402 |
| cca gtt gag aag aag tcc tca gct aga agt aca caa ggt act aca ggg<br>Pro Val Glu Lys Lys Ser Ser Ala Arg Ser Thr Gln Gly Thr Thr Gly<br>                      105                        110                        115 | 450 |
| ata aga gaa gat cct gat gtc tgc ctg aaa gcc cca tgaagaaaaa<br>Ile Arg Glu Asp Pro Asp Val Cys Leu Lys Ala Pro<br>                    120                        125 | 496 |
| taaaacacct tgtactttat tttctataat ttaaatatat gctaagtctt atatattgta | 556 |
| gataatacag ttcggtgagc tacaaatgca tttctaaagc cattgtagtc ctgtaatgga | 616 |
| agcatctagc atgtcgtcaa agctgaaatg gacttttgta catagtgagg agctttgaaa | 676 |
| cgaggattgg gaaaagtaat tccgtaggtt attttcagtt attatattta caaatgggaa | 736 |
| acaaaaggat aatgaatact ttataaagga ttaatgtcaa ttcttgccaa atataaataa | 796 |
| aaataatcct cagttttttgt gaaaagctcc attttttagtg aaatattatt ttatagctac | 856 |
| taatttttaaa atgtcttgct tgattgtatg gtgggaagtt ggctggtgtc ccttgtcttt | 916 |
| gccaagttct ccactagcta tggtgtcata ggctcttttg ggattttttga agctgtatac | 976 |
| tgtgtgctaa acaagcact aaacaaagag tgaaggattt atgtttaatt ctgaaagcaa | 1036 |
| ccttcttgcc tagtgttctg atattggaca gtaaaatcca cagaccaacc tggagttgaa | 1096 |
| aatcttataa tttaaaatat gctctaaaca tgtttatcgt atttgatgct acaggatttg | 1156 |
| aaattgtatt acaaatccaa tgaaatgagt ttttctttttc atttacctct gccccagttg | 1216 |
| tttctactac atggaagacc tcattttgaa gggaaatttc agcagctgca gctcatgagt | 1276 |
| aactgatttg taacaagcct ccttttaaag taaccctaca aaaccactgg aaagtttatg | 1336 |
| gttgtattat tttttaaaaa aattccaagt gattgaaact tacacgagat acagaattttt | 1396 |
| atgcggcatt ttcttctcac attttatattt ttgtgattttt gtgattgatt atatgtcact | 1456 |
| ttgctacagg gctcacagaa ttcattcact caacaaacat aatagggcgc tgagggcata | 1516 |
| gaagtaaaaa cacctggtcc ctgctctcag ttcactgtct tgttggacga aaaacaata | 1576 |
| acgataaaag acagtgaaag aaaataacga taaagacag tgaaagaaaa taacaataaa | 1636 |
| agacaaggaa aaaataacaa tgaaagttga taagtacatg ataagcgagg ttccccgtgt | 1696 |
| gtaggtagat ctggtctttta gaggcagata ataggtcag tgcaaatact ctggtccatg | 1756 |
| ggccatatga aaaggctaag cttcactgta aaataataac tgggaattct gggttgtgta | 1816 |
| tgggtgttgg tgaacttggt tttaattagt gaactgctga gagacagagc tattctccat | 1876 |
| gtactggcaa gacctgattt ctgagcattt aatatggatg ccgtgggagt acaaaagtgg | 1936 |
| agtgtggcct gagtaatgca ttatgggtgg tttaccatttt cttgaggtaa agcatcaca | 1996 |
| tgaacttgta aaggaattta aaaatcctac tttcataata agttgcatag gtttaataat | 2056 |
| ttttaattat atggcttgag tttaaattgt aataggcgta actaatttta actctataat | 2116 |
| gtgttcattc tggaataatc ctaaacatat gaattatgtt tgcatgttca cttccaagag | 2176 |
| ccttttttttg aaaaaaagct tttttttgaat catcaagtct ttcacattta aataaagtgt | 2236 |
| ttgaaagctt tatttaaaaa aaaaaaaaaa aaaaaaaaa | 2276 |

-continued

```
<210> SEQ ID NO 7
<211> LENGTH: 4343
<212> TYPE: DNA
<213> ORGANISM: Homo sapiens
<220> FEATURE:
<221> NAME/KEY: CDS
<222> LOCATION: (1)..(1029)

<400> SEQUENCE: 7 atg gac gcc cca aaa gca gga tac gcc ttt gag tac ctt att gaa aca        48
Met Asp Ala Pro Lys Ala Gly Tyr Ala Phe Glu Tyr Leu Ile Glu Thr
 1               5                  10                  15 tta aat gac agt tca cat aag aag ttc ttc gat gta tct aaa ctt ggc        96
Leu Asn Asp Ser Ser His Lys Lys Phe Phe Asp Val Ser Lys Leu Gly
             20                  25                  30 acc aag tat gat gtt ctg cct tac tca ata cgg gtc ttg ttg gaa gct       144
Thr Lys Tyr Asp Val Leu Pro Tyr Ser Ile Arg Val Leu Leu Glu Ala
         35                  40                  45 gct gta cga aat tgt gat ggc ttt tta atg aag aag gaa gat gtt atg       192
Ala Val Arg Asn Cys Asp Gly Phe Leu Met Lys Lys Glu Asp Val Met
     50                  55                  60 aac att tta gac tgg aaa acc aaa caa agc aat gtt gaa gtg ccc ttt       240
Asn Ile Leu Asp Trp Lys Thr Lys Gln Ser Asn Val Glu Val Pro Phe
 65                  70                  75                  80 ttc cct gcc cgt gtt ctt ctt caa gat ttt act gga ata cca gca atg       288
Phe Pro Ala Arg Val Leu Leu Gln Asp Phe Thr Gly Ile Pro Ala Met
                 85                  90                  95 gtg gat ttt gct gct atg agg gag gca gtg aaa act ctt gga ggt gat       336
Val Asp Phe Ala Ala Met Arg Glu Ala Val Lys Thr Leu Gly Gly Asp
            100                 105                 110 cct gag aaa gtc cat cct gct tgt ccg aca gat ctt aca gtt gac cat       384
Pro Glu Lys Val His Pro Ala Cys Pro Thr Asp Leu Thr Val Asp His
        115                 120                 125 tct tta caa att gac ttc agt aaa tgt gca ata cag aat gca cca aat       432
Ser Leu Gln Ile Asp Phe Ser Lys Cys Ala Ile Gln Asn Ala Pro Asn
    130                 135                 140 cct gga ggt ggt gac ctg cag aaa gca gga aag ctc tct cca ctt aaa       480
Pro Gly Gly Gly Asp Leu Gln Lys Ala Gly Lys Leu Ser Pro Leu Lys
145                 150                 155                 160 gtg cag cct aag aag ctt ccc tgc aga ggc cag act acc tgc cga gga       528
Val Gln Pro Lys Lys Leu Pro Cys Arg Gly Gln Thr Thr Cys Arg Gly
                165                 170                 175 tct tgt gat tct gga gaa cta ggc cga aac tca gga aca ttt tct tcg       576
Ser Cys Asp Ser Gly Glu Leu Gly Arg Asn Ser Gly Thr Phe Ser Ser
            180                 185                 190 cag att gag aat aca ccc atc ctg tgt cct ttt cat ttg caa cca gtg       624
Gln Ile Glu Asn Thr Pro Ile Leu Cys Pro Phe His Leu Gln Pro Val
        195                 200                 205 cct gaa cct gaa aca gtg tta aaa aat caa gaa gta gaa ttc ggc aga       672
Pro Glu Pro Glu Thr Val Leu Lys Asn Gln Glu Val Glu Phe Gly Arg
    210                 215                 220 aat cga gag agg ctt cag ttt ttt aag tgg agt tca aga gtt tta aag       720
Asn Arg Glu Arg Leu Gln Phe Phe Lys Trp Ser Ser Arg Val Leu Lys
225                 230                 235                 240 aat gtg gca gtg atc cct cct gga act gga atg gct cat caa ata aac       768
Asn Val Ala Val Ile Pro Pro Gly Thr Gly Met Ala His Gln Ile Asn
                245                 250                 255 tta gaa tat ttg tca aga gtg gtt ttt gaa gaa aaa gac ctc ctc ttc       816
Leu Glu Tyr Leu Ser Arg Val Val Phe Glu Glu Lys Asp Leu Leu Phe
            260                 265                 270
```

|  |  |
|---|---|
| cca gac agt gta gtc ggc aca gat tca cac ata acg atg gtg aat ggt<br>Pro Asp Ser Val Val Gly Thr Asp Ser His Ile Thr Met Val Asn Gly<br>        275                      280                      285 | 864 |
| tta ggg att ctg ggg tgg ggg gtt gga ggc att gaa aca gaa gca gtt<br>Leu Gly Ile Leu Gly Trp Gly Val Gly Gly Ile Glu Thr Glu Ala Val<br>        290                      295                      300 | 912 |
| atg ctt ggt ctg cca gtt tct ctt act tta cca gag gtg gtt gga tgt<br>Met Leu Gly Leu Pro Val Ser Leu Thr Leu Pro Glu Val Val Gly Cys<br>305                      310                      315                      320 | 960 |
| gag tta act ggg tca tca aac cct ttt gtt aca tcc ata gat gtt gtt<br>Glu Leu Thr Gly Ser Ser Asn Pro Phe Val Thr Ser Ile Asp Val Val<br>                  325                      330                      335 | 1008 |
| ctt ggt att aca aag gta agt taaagttgtg gtagctctat gacttactga<br>Leu Gly Ile Thr Lys Val Ser<br>                340 | 1059 |
| acattatttt tataaaaatt gaagagctct atgagagcag ggatttgggt tcattactgc | 1119 |
| atcctcaggt ctcttgacgt tagccacatc atcatagtta tcatagtaat aacaacaaac | 1179 |
| agagcattta gtttgtacta ataaatacaa agaaatttgt tgtgttcact tatgttagct | 1239 |
| catttagtcc ttataacaag cctgtgagat ggatactatt actattctca ttgtaactct | 1299 |
| gagaaaacta aggtacagta gggtttagtg acttaccaaa gggtcgaagg cctgagtata | 1359 |
| aggggtagag caaagattcc aggcagtcag attcttgagt catgtctaac cattatgcct | 1419 |
| tattagtgcc ttgttgcctt aataaacact tgctggacta catatttttt ttctcttttt | 1479 |
| taacttgaat taaaaaaaaa tgtttagcaa aagttgawtg tgtcgtcttt aattaaatta | 1539 |
| tttgcccgtt agaaactgtt gctctactaa gtaatgcttt caaaaacatg gactgtagaa | 1599 |
| atgtgatata tcatttttct gttgccgttt taacatttct ctggattatt atgtaaaaat | 1659 |
| cttctctctg aattttttaaa atactggctt cagaacttca atacatacac tgagcttgtt | 1719 |
| aagcatatta atacacaggc tcacggattt cctagtgaac aataaatttgt aactcttctt | 1779 |
| cctaaatgtc tggcctttgc taactttatt ttaatgatta atcctatttt tgttaaatga | 1839 |
| atgtacctgg aaaatgttcc acatataatt ccaatttgag tcccaatctc agcattttg | 1899 |
| gttagattat tggtacgaag gctttctgga tactccagtg taaggaaatg ataatgcctc | 1959 |
| cctctcagca tttggtattg atccttcttc cctaattaga aaagaatttg gcatcttaga | 2019 |
| gaaattattg attcaacgta tgataccaaa agatcaagta gtaaattggg aattgcagga | 2079 |
| ttattcctag aggaaaagga gtatcccatt atgtttttac agaaatcaat tctttacttt | 2139 |
| agacatcctg aaaactaacg ctgcttttta gccttctcta gctgtttttt cctgacaata | 2199 |
| ttactgtgtg ttttttgaca ttttagttta atgttaaaaa attaatctat tatatatgtt | 2259 |
| tacatttatt gaatatattg attacttctt ttttgagatc ctgttccatt tgtgatcctt | 2319 |
| ataggaataa tcctgtattg ttttttgat gagagcagca tttggtttgt aatatctaat | 2379 |
| ctgtgtttct ttcatcctaa aaaataaaac cataggccgg gcgcggtggc tcacgcctgt | 2439 |
| aatcccagca ctttgggagg ccgaggcggg tggatcatga ggtcaggaga tcgagaccat | 2499 |
| cctggctaac aaggtgaaac cccgtctcta ctaaaaatac aaaaaattag ccgggcgcgg | 2559 |
| tggcgggcgc ctgtagtccc agcttctcgg gaggctgagg caggagaatg gcgtgaaccc | 2619 |
| gggaggcgga gcttgcagtg agccaagatt gcgccactgc agtccgcagt ccggcctggg | 2679 |
| cgacagagcg agactctgty tcaaaaaaaa aaaaaaaaa aaaaaaacca taaatgagga | 2739 |
| aacgcatctt tacacttagg gtttgagttt ctgtatctat aaaaagggt ttggattaag | 2799 |
| tgatccctgg cacttataaa atgttagggc ttaatattat tcatagatcg aggatagttt | 2859 |

| | |
|---|---|
| cattcttagt cgcctcctta gtcactcttc ctataccaat ctgagaccat tttacaattt | 2919 |
| agaaaagaca ataactggt tgggttactt gatagtataa taaccaagaa aaataatttt | 2979 |
| agaaggaatt aagtttgaaa ccacatgtta acaaattcta ccaaagtggg atttgcctgt | 3039 |
| gattaaagat gctgtaaaca tttgggccag tagttataat ttgaaaaatg tttatagcca | 3099 |
| atatataatt ttttatttaa atatacagtt tcatcagtct attagtattt cattaagtct | 3159 |
| aagatgccat cagtggttag caaacaccac tgttttatgc actgctaaga aagaataaag | 3219 |
| ggctgtgtgc agtggctcac acctgtggga cgccaaggca ggagcatcac ttgaggccag | 3279 |
| aagttcaaga ccaacctggt caacattgta agaccctgtc tctacaaaaa aaaaaaagtt | 3339 |
| aaaaattagc tgggtgcggt ggcacatgcc tgtagttcca gctactctgg aggctaaggt | 3399 |
| gggaggattg ctagagccac ggtgttggaa gctgcaatga gctgtgacca caccactgcg | 3459 |
| ctccagcgtg ggcaacagag tgagaccctg tttctaaaag aaagaaagaa aaagggctg | 3519 |
| ccacctaaac agacacacta ttgagttgag gtaccctgat ttcaaagaca tgaaaatgtt | 3579 |
| aattatagcc accttgaagc tttcaggscc cttttctaccc tgaattaaca gtgacattgg | 3639 |
| accagtcttc tctttacttc ttatcttaaa atacccccaa aaccagaatg agttgattca | 3699 |
| taaggacaat gaaggatctc attccttcac catcactagt attggttaaa aatttttattt | 3759 |
| tatagttttc agacaatcgt tgctaatctt atctttgcaa ttttgtatgt gtttctgtgt | 3819 |
| attccttata tagcacctca ggcaagtagg agtggctgga aagtttgttg agtttttgg | 3879 |
| aagtggagtt tcacaattat ctatagttga tcgaactaca atagcaaaca tgtgtccgga | 3939 |
| atatggtgct atcctcagct ttttccctgt tgacaatgtg acattaaaac atttagaaca | 3999 |
| tacaggtaag aagataaaag atcactagaa taaacatgtt acatttccaa tgtgtttgat | 4059 |
| aatatttat aaattactac cttatccatg ttatttacta ctcacaaaat tacattatgt | 4119 |
| tgaaacaaca acttcaagc aaacatcaga tgtcttaaa gagtgttgtg tcctcaaacc | 4179 |
| ctagttccct gtgacacatt gaaagcaatt taaaggaatt attcaaacca ttgatcctga | 4239 |
| cttgactgtt tcccataatg atggatacct cccctctac ttaggggtca taggtgcaat | 4299 |
| ttaatggagt cagcccttaa acatattcac agcagtcccc ttct | 4343 |

<210> SEQ ID NO 8
<211> LENGTH: 155
<212> TYPE: DNA
<213> ORGANISM: Homo sapiens

<400> SEQUENCE: 8

| | |
|---|---|
| cacttataaa atgttagggc ttaatattat tcatagatcg aggatagttt cattcttagt | 60 |
| cgcctcctta gtcactcttc ctataccaat ctgagaccat tttacaattt agaaaagaca | 120 |
| aataactggt tgggttactt gatagtataa taacc | 155 |

<210> SEQ ID NO 9
<211> LENGTH: 278
<212> TYPE: DNA
<213> ORGANISM: Homo sapiens
<220> FEATURE:
<221> NAME/KEY: unsure
<222> LOCATION: (29), (32), (35)
<223> OTHER INFORMATION: A or G or C or T

<400> SEQUENCE: 9

| | |
|---|---|
| gaaggagaat atgaagaggt tagaaaagnt cnggnttctg ttggtgaaat gaaggatgaa | 60 |
| ggggaagaga cattaaatta tcctgatact accattgact tgtctcacct tcaaccccaa | 120 |

```
aggtccatcc agaaattggc ttcaaaagag gaatcttcta attctagtga cagtaaatca      180
cagagccgga gacatttgtc agccaaggaa agaagggaaa tgaaaaagaa aaaacttcca      240
agtgactcag gagatttaga agcgttagag ggaaagga                             278
```

```
<210> SEQ ID NO 10
<211> LENGTH: 135
<212> TYPE: DNA
<213> ORGANISM: Homo sapiens

<400> SEQUENCE: 10
ttctgacaat gagtaagaag aaagagggtc ttgcccttg gttattaaga tttatcatag      60
agcaataata astaaatcgg tgttatacca gcacagagat tagacaaata aaccaaggga    120
ctggactaaa taagc                                                     135
```

```
<210> SEQ ID NO 11
<211> LENGTH: 197
<212> TYPE: DNA
<213> ORGANISM: Homo sapiens

<400> SEQUENCE: 11
atggtaccca gtttcaaatt aacatggtta ttttacttgt gttcccaaat ttaacattag     60 ggaattttg gttgtgggtc tgttatcact agaaaaatat atatattggt gctgaagata    120
attttgagat aattagacaa gacagtttag catttacaag aacaagtttg gcagttgaag    180
aatctattta tatgact                                                   197
```

```
<210> SEQ ID NO 12
<211> LENGTH: 137
<212> TYPE: DNA
<213> ORGANISM: Homo sapiens

<400> SEQUENCE: 12
ccaccgcacc tggctgatgc ttttctatct gacttctttc agaggaccct gaaagacact     60
aagtggaatc tttccttgaa gtcttccaag ctaaaacaat tctctggaaa gatcacctct    120
gttcagtcct ggtctct                                                   137
```

```
<210> SEQ ID NO 13
<211> LENGTH: 274
<212> TYPE: DNA
<213> ORGANISM: Homo sapiens

<400> SEQUENCE: 13
cgtttacaga ttctcttgcg gctggcggtg gaactacaaa gggatcggtg cctatatcac     60
aataccaaac ttgataataa tctagattct gtgtytctgc ttatagacca tgtttgtagt    120
aggtaagagg aaaacttcct atattctgaa acagcctaac attttacaaa attttagttt    180
tcttttttag agtcttatcc tgtagctata taacagttca tgtctgattt agcatttgtt    240
cacgagtaaa gctggaacta tgaaaattga aaat                                274
```

```
<210> SEQ ID NO 14
<211> LENGTH: 171
<212> TYPE: DNA
<213> ORGANISM: Homo sapiens
<220> FEATURE:
<221> NAME/KEY: unsure
<222> LOCATION: (72), (127), (150)
<223> OTHER INFORMATION: A or G or C or T
```

```
<400> SEQUENCE: 14
gattaggtga ccttccttga aragccacgg gtttcccata tcgaaatgct attcattacc      60
cgagtcacct angttcttac aaaggaagcg agaaaattgc ttttgttggg ccatgccct     120 tttgcanagg ttcctaagta tagtcgccan aatttttta atggcctaaa g              171

<210> SEQ ID NO 15
<211> LENGTH: 161
<212> TYPE: DNA
<213> ORGANISM: Homo sapiens

<400> SEQUENCE: 15
aggggcgctt gttctgctct cagcagattg gttacacgcg tcaggtggtg gcgatgactt     60
aattcctagc ccaagaagaa tataatgtta aaactggtta tgtaattttt gtgcctctcc   120
tttttaatgc agtatttagt tcagatgttg gcgattttc a                         161

<210> SEQ ID NO 16
<211> LENGTH: 323
<212> TYPE: DNA
<213> ORGANISM: Homo sapiens

<400> SEQUENCE: 16
tataaggwgg gaaccttact atctctaatg accttactga tgctgacttt aatactctgt     60
gaaggttaga gttcagtgaa tgttacctag aaacagcccc ggctgtggaa tactttattc   120
ttagccctat atttggggtt tggatgtcca ctgtgctggt tcccagagat agtaagggga   180
tgagagtatt ggttacatct cctgacccac atacttaaga tccagatgaa caagacagtt   240
ttcactcctg cttggtagaa cctatttgyk shaggaaaca gytcctaaag aatggttcta   300
gccagaccct gtcgytacca gaa                                           323

<210> SEQ ID NO 17
<211> LENGTH: 138
<212> TYPE: DNA
<213> ORGANISM: Homo sapiens

<400> SEQUENCE: 17
agtatgacaa atagtttctg cctgattggt gagatttggg atgggccccc actttgtttc     60
tctttctgca taaaaatttc aacattttta caaaatttttt aaaaacttct cctcagtctg   120
tacatctttg ttaatcag                                                  138

<210> SEQ ID NO 18
<211> LENGTH: 135
<212> TYPE: DNA
<213> ORGANISM: Homo sapiens

<400> SEQUENCE: 18
tgatccccac aatttcttgt gattggtgag gaactataaa tgactcccat ccaagcttat     60
accagaaaaa aggagcacat tttctacaaa ttatatcatt tttaatccat taccacatta   120
ttttagggga actac                                                    135

<210> SEQ ID NO 19
<211> LENGTH: 219
<212> TYPE: DNA
<213> ORGANISM: Homo sapiens
```

```
<400> SEQUENCE: 19
ctgagaggag ccatgtatac aaaccacttt ttctaacatg gtctttatta aactttgaat      60
ataagtacac ctgctcgaag tgttcatcta tattatttaa gaacaagcaa ctgtaaaaca     120
gtaaaatcac aaaaggtaag ttgttggaag acaacaaaaa agaattacta tatctgatcc     180
tgcgtgttta ttttagaatc tgttaatagg cctacagct                            219

<210> SEQ ID NO 20
<211> LENGTH: 191
<212> TYPE: DNA
<213> ORGANISM: Homo sapiens

<400> SEQUENCE: 20
acagtgagtg tggctgaaac ctaagctgaa ggaagggagg agcaggcact gccatgaggg      60
gtccctggac agaaactctt cagcaggcct tgaagtttag ttcagggggct acatggaata    120 ccactattta gcacacaggt gtgatctgag gtgagggact acctttttcga tcttggtttt    180 ctcatttatt t                                                         191

<210> SEQ ID NO 21
<211> LENGTH: 148
<212> TYPE: DNA
<213> ORGANISM: Homo sapiens

<400> SEQUENCE: 21
ctggaggtga agggaaggaa agaaaggaaa aactatctac ctggcaggaa aagagataag      60
ctcccaagaa caccaaagca gatgatgagt ctagctctac ccagccttcc tccccacgaa     120
tccagatcat agtaagaaac tctgggct                                       148

<210> SEQ ID NO 22
<211> LENGTH: 306
<212> TYPE: DNA
<213> ORGANISM: Homo sapiens

<400> SEQUENCE: 22
ccaccaccag aaatgaacaa aaagcatttt acctaaaaat acaccagcaa aatgtactca      60
gcttcaatca caaatacgac tgcttaaaac cgcagaaatt tcctcaacac tcagccttta    120
tcactcagct ggattttttc cttcaacaat cactactcca agcattgggg aacacaactt    180
ttaatcatac tccagtcgtt tcacaatgca ttctaatagc agcgggatca gaacagtact    240
gcatttactt gccaacagaa cagacagacc tgaagtcaag caactgcat tctctgtgaa     300 gtctgt                                                               306

<210> SEQ ID NO 23
<211> LENGTH: 357
<212> TYPE: DNA
<213> ORGANISM: Homo sapiens

<400> SEQUENCE: 23
gtagcatttt ggcagaacca ttgttaatta aagggactty tggaccgcaa cyttaatgta      60
ccagattatt gagcrgccca atgaatgctt cattctcatt gtttaaggtg ctgctttgat     120
ttttttttca attctttgta ctattttta tttttttggag aggcacatcc ccaaatttgg    180
atgaggtatt tgttgataaa taattcatca atttccacaa tgcagacaaa aatgtctgcc    240
cagagtggaa aaataaaaca aggggggagaa gagtttgagt aacggagaag ttctgtggaa    300
tcctagtgac aaaagttgag aaactacctt taaataagac agtgaggtaa caaatgt       357
```

```
<210> SEQ ID NO 24
<211> LENGTH: 219
<212> TYPE: DNA
<213> ORGANISM: Homo sapiens

<400> SEQUENCE: 24
tggaatagcc aggagaattc tgaaaagta gaataatgag gtagggcttc ccttcgctat      60
tttgaagtgc agattacact atgtaaaacc attaggaact ggcacgtgaa tagacagatc    120
aatagttaat agctgtatta gccagaaaat ggtgtaagga caacaggcta actaaccctg    180
tcacttgtta tgctaaaatt aagtctagat agagtcctc                           219

<210> SEQ ID NO 25
<211> LENGTH: 251
<212> TYPE: DNA
<213> ORGANISM: Homo sapiens

<400> SEQUENCE: 25
tgaaagggga atagaagcac aagagtcagt aatcaataac aaacaactca aggtgctcct     60
tccttacact ggtgttcccc aaagtgaggt gaattgccag ccactgggag tcagggccag    120
ttacataaga cattctcggt aagccccctt tgggtatccc aaataaggac tggggtgggt    180
ttatgtgtag tccattatta caactaaac gaacaaacct agtgaattgc ataaaattca     240
caccaacaga a                                                         251

<210> SEQ ID NO 26
<211> LENGTH: 233
<212> TYPE: DNA
<213> ORGANISM: Homo sapiens

<400> SEQUENCE: 26
gttgaaagag tccttggaag gcttttagac caaacccctc tgcatgctca arccttgggt     60
acaggatttc taagaagtgg aacagtctcc agggtgtgg arctcatcgc tcaaggcagg    120
ttatcttatc tgaataattt tgtctgttga ctattgggat agttctcctt cagatgagct    180
gaaattttct ccatagcttc ctctattaaa cccaattcca cttctcaggg tca           233

<210> SEQ ID NO 27
<211> LENGTH: 176
<212> TYPE: DNA
<213> ORGANISM: Homo sapiens

<400> SEQUENCE: 27
caaaagcgct gaagttaagc attaatacgc cagattcatg atttatgatc agtatccaaa     60
actccaacta caaacaatgc aaagtagtgc tcctcagtat tatttttgca attgttagta    120
atgttaagca tcaaggaaaa taaaacacat cattgcacat tacagccgca aaaaac        176

<210> SEQ ID NO 28
<211> LENGTH: 241
<212> TYPE: DNA
<213> ORGANISM: Homo sapiens

<400> SEQUENCE: 28
agagagtaaa gcaagctatt ttgacagcaa cctaataaca gctgtcttct tccacttctt     60
ggctaactca tcccccagat agccttcttt tctcttatca attccctgtt gcaacaataa    120
taaatgccac acctgatgga gtcattaggc actttcctag tgacaagtgc ctaggacaga    180
```

| | |
|---|---|
| ggagaaaaca aagaaacact gacaaccact gaaaactgac atatcaggcc aggcatgtca | 240 |
| c | 241 |

<210> SEQ ID NO 29
<211> LENGTH: 217
<212> TYPE: DNA
<213> ORGANISM: Homo sapiens

<400> SEQUENCE: 29

| | |
|---|---|
| gctggagagg tggtgatgtt gctgaataat tgcttttta agctggaggg gacttccaag | 60 |
| agtctctcat ttaagaaraa aaattaaaga cataattggt aacggttttg actgctgcag | 120 |
| aggcaacact ttgctcacaa tcctacagat ctacttcacc tgtaactaca attttcctga | 180 |
| agacatagaa gaaaaatcaa ttgttctaat ccatatg | 217 |

<210> SEQ ID NO 30
<211> LENGTH: 233
<212> TYPE: DNA
<213> ORGANISM: Homo sapiens

<400> SEQUENCE: 30

| | |
|---|---|
| aatcttagca taatgcttcc tgggaaattc tgaaattgat tccatttctg ccgttacaaa | 60 |
| cacacacgaa gttcctagtt cactgggact tcctgatttg ttcttttagc ttgctccttc | 120 |
| tcacctagaa gctctgttta tttctgagca accctggggc ttgtctcata ggacaggatt | 180 |
| tatttatctc atcaaggctg agtgtgcctt aggaagtcat aaacataaaa aga | 233 |

<210> SEQ ID NO 31
<211> LENGTH: 228
<212> TYPE: DNA
<213> ORGANISM: Homo sapiens

<400> SEQUENCE: 31

| | |
|---|---|
| tatagacagg gtagggacga ttagcccctc gacaactttt cacaaatata cacacgttta | 60 |
| actacctctc aggtcatgat aaagaccggc cgggcagaaa cactgtaatc ccagctactc | 120 |
| gggagcctga ggcatgagaa tcacttgaac ctggaggtg gaggttgcca tgagccgaga | 180 |
| tcacgccatt gcactacagc cttggcgaca agagtgaaac tccatctg | 228 |

<210> SEQ ID NO 32
<211> LENGTH: 298
<212> TYPE: DNA
<213> ORGANISM: Homo sapiens
<220> FEATURE:
<221> NAME/KEY: unsure
<222> LOCATION: (44)
<223> OTHER INFORMATION: A or G or C or T

<400> SEQUENCE: 32

| | |
|---|---|
| gcttatgatt acaaacatcc ctcatatgaa aatctcagca tttnctggct gctgccttca | 60 |
| atcgcttttt ctgaaatagg tatcccttga tgtcgactat ttgatttcag ccagtcgttt | 120 |
| ctctctggca gtgctccctg caaatgtgtc ctttcaagaa aacaaaacct gcaagtggct | 180 |
| tgtaatgtac catgacctta tcatgtgaag gacaaatggc tcttgtgctt attagatagc | 240 |
| agatgaactg atgaactgaa ttcttggtct gaagctttga taaggtcaga tgtctttg | 298 |

<210> SEQ ID NO 33
<211> LENGTH: 291
<212> TYPE: DNA
<213> ORGANISM: Homo sapiens

<400> SEQUENCE: 33

```
acttcgaagg gaaaagagg aaggaaaagg actgttaata aaataacaaa ggcagcaatc     60
agaatgaacc agagccagga cagcgtaaag gctaggttca cagtgagatg aaagaacctg   120
aaaacaagtt taaaactcaa aagaggatta ttctcaagtt atactacagt gaaaaacat    180
ggaaaaacac aaaaaggaca ggcaataagg cacaggcata catacaaggc aaattgtaac   240
acaatattta cttgcaaaag agcccacaga gacatgtcaa tgaagtcata g            291
```

<210> SEQ ID NO 34
<211> LENGTH: 230
<212> TYPE: PRT
<213> ORGANISM: Homo sapiens

<400> SEQUENCE: 34

```
Met Glu Asp Gly Phe Leu Asp Asp Gly Arg Gly Asp Gln Pro Leu His
  1               5                  10                  15

Ser Gly Leu Gly Ser Pro His Cys Phe Ser His Gln Asn Gly Glu Arg
                 20                  25                  30

Val Glu Arg Tyr Ser Arg Lys Val Phe Val Gly Gly Leu Pro Pro Asp
             35                  40                  45

Ile Asp Glu Asp Glu Ile Thr Ala Ser Phe Arg Arg Phe Gly Pro Leu
         50                  55                  60

Ile Val Asp Trp Pro His Lys Ala Glu Ser Lys Ser Tyr Phe Pro Pro
 65                  70                  75                  80

Lys Gly Tyr Ala Phe Leu Leu Phe Gln Asp Glu Ser Ser Val Gln Ala
                 85                  90                  95

Leu Ile Asp Ala Cys Ile Glu Glu Asp Gly Lys Leu Tyr Leu Cys Val
            100                 105                 110

Ser Ser Pro Thr Ile Lys Asp Lys Pro Val Gln Ile Arg Pro Trp Asn
            115                 120                 125

Leu Ser Asp Ser Asp Phe Val Met Asp Gly Ser Gln Pro Leu Asp Pro
        130                 135                 140

Arg Lys Thr Ile Phe Val Gly Gly Val Pro Arg Pro Leu Arg Ala Val
145                 150                 155                 160

Glu Leu Ala Met Val Met Asp Arg Leu Tyr Gly Gly Val Cys Tyr Ala
                165                 170                 175

Gly Ile Asp Thr Asp Pro Glu Leu Lys Tyr Pro Lys Gly Ala Gly Arg
            180                 185                 190

Val Ala Phe Ser Asn Gln Gln Ser Tyr Ile Ala Ala Ile Ser Ala Arg
        195                 200                 205

Phe Val Gln Leu Gln His Gly Glu Ile Asp Lys Arg Val Ser Leu Ile
    210                 215                 220

Leu His Phe Gly Lys Phe
225                 230
```

<210> SEQ ID NO 35
<211> LENGTH: 143
<212> TYPE: PRT
<213> ORGANISM: Homo sapiens

<400> SEQUENCE: 35

```
Met Gly Ser Asp Lys Arg Val Ser Arg Thr Glu Arg Ser Gly Arg Tyr
  1               5                  10                  15

Gly Ser Ile Ile Asp Arg Asp Asp Arg Asp Glu Arg Glu Ser Arg Ser
                 20                  25                  30
```

```
Arg Arg Arg Asp Ser Asp Tyr Lys Arg Ser Asp Asp Arg Arg Gly
        35                  40                  45

Asp Arg Tyr Asp Asp Tyr Arg Asp Tyr Asp Ser Pro Glu Arg Glu Arg
    50                  55                  60

Glu Arg Arg Asn Ser Asp Arg Ser Glu Asp Gly Tyr His Ser Asp Gly
65                  70                  75                  80

Asp Tyr Gly Glu His Asp Tyr Arg His Asp Ile Ser Asp Glu Arg Glu
                85                  90                  95

Ser Lys Thr Ile Met Leu Arg Gly Leu Pro Ile Thr Ile Thr Glu Ser
            100                 105                 110

Asp Ile Arg Glu Met Met Glu Ser Phe Glu Gly Pro Gln Pro Ala Asp
        115                 120                 125

Val Arg Leu Met Lys Arg Lys Thr Gly Glu Ser Leu Leu Ser Ser
    130                 135                 140

<210> SEQ ID NO 36
<211> LENGTH: 104
<212> TYPE: PRT
<213> ORGANISM: Homo sapiens

<400> SEQUENCE: 36

Met Pro His Met Leu Ser Gln Leu Ile Ala Gly Gly Val Ser Thr Ser
1               5                   10                  15

Cys Val Thr Ala Leu Gly Glu Glu Thr Gly Ala Trp Phe Pro Val Tyr
            20                  25                  30

Leu Ser His Ala Ser Ser Pro Phe Ala Asp Leu Val Phe Cys Pro Phe
        35                  40                  45

Ala Glu Ile Asn His Ser Gln Glu Tyr Asp Asn Met Arg Gly Pro Val
    50                  55                  60

Ser Pro Pro Asn Lys Gln Phe Asn Leu Gly Val Ile Phe Gly Ile Pro
65                  70                  75                  80

Asn Asn Cys Arg Phe Pro Thr Asp Asn Lys Ile Thr Glu Lys Gln Leu
                85                  90                  95

Leu Gly Asn Val Leu Asn Tyr Pro
            100

<210> SEQ ID NO 37
<211> LENGTH: 133
<212> TYPE: PRT
<213> ORGANISM: Homo sapiens

<400> SEQUENCE: 37

Met Asn His Pro Trp His Val Cys Phe Leu Phe Lys Val Leu Arg Tyr
1               5                   10                  15

Tyr Pro Thr Ala Pro Ile Leu Lys Trp Thr His Thr Val Ser Cys Ser
            20                  25                  30

Trp Cys Arg Ser Val Leu Arg Glu Val Val Gly Asn Val Ser Leu Ser
        35                  40                  45

Glu Asn Phe Thr Ile Ser Ala Phe Cys Pro Glu Leu Thr Pro Phe Pro
    50                  55                  60

Asp Gln Gly Thr Ser Thr Met Ile Ser Phe Leu Glu Lys Phe Asn Lys
65                  70                  75                  80

Ser Lys Arg Glu Arg Leu Glu Leu Met Leu His Phe Tyr Ser Val Leu
                85                  90                  95

Ser Leu Glu Pro Ala Val Ala Glu His Trp Ser Gly Glu Phe Glu Lys
            100                 105                 110
```

```
Trp Lys Val Gly Phe Phe His Pro Leu Lys Arg Glu Asp Gly Phe Phe
        115                 120                 125

Thr Arg Thr Asp Ile
    130

<210> SEQ ID NO 38
<211> LENGTH: 133
<212> TYPE: PRT
<213> ORGANISM: Homo sapiens

<400> SEQUENCE: 38

Met Asn His Pro Trp His Val Cys Phe Leu Phe Lys Val Leu Arg Tyr
  1               5                  10                  15

Tyr Pro Thr Ala Pro Ile Leu Lys Trp Thr His Thr Val Ser Cys Ser
             20                  25                  30

Trp Cys Arg Ser Val Leu Arg Glu Val Val Gly Asn Val Ser Leu Ser
         35                  40                  45

Glu Asn Phe Thr Ile Ser Ala Phe Cys Pro Glu Leu Thr Pro Phe Pro
     50                  55                  60

Asp Gln Gly Thr Ser Thr Met Ile Ser Phe Leu Glu Lys Phe Asn Lys
 65                  70                  75                  80

Ser Lys Arg Glu Arg Leu Glu Leu Met Leu His Phe Tyr Ser Val Leu
                 85                  90                  95

Ser Leu Glu Pro Ala Phe Ala Glu His Trp Ser Gly Glu Phe Glu Lys
            100                 105                 110

Trp Lys Val Gly Phe Phe His Pro Leu Lys Arg Glu Asp Gly Phe Phe
        115                 120                 125

Thr Arg Thr Asp Ile
    130

<210> SEQ ID NO 39
<211> LENGTH: 128
<212> TYPE: PRT
<213> ORGANISM: Homo sapiens

<400> SEQUENCE: 39

Met Asp Ala Val Ala Val Tyr His Gly Lys Ile Ser Arg Glu Thr Gly
  1               5                  10                  15

Glu Lys Leu Leu Leu Ala Thr Gly Leu Asp Gly Ser Tyr Leu Leu Arg
             20                  25                  30

Asp Ser Glu Ser Val Pro Gly Val Tyr Cys Leu Cys Val Leu Tyr His
         35                  40                  45

Gly Tyr Ile Tyr Thr Tyr Arg Val Ser Gln Thr Glu Thr Gly Ser Trp
     50                  55                  60

Ser Ala Glu Thr Ala Pro Gly Val His Lys Arg Tyr Phe Arg Lys Ile
 65                  70                  75                  80

Lys Asn Leu Ile Ser Ala Phe Gln Lys Pro Asp Gln Gly Ile Val Ile
                 85                  90                  95

Pro Leu Gln Tyr Pro Val Glu Lys Lys Ser Ser Ala Arg Ser Thr Gln
            100                 105                 110

Gly Thr Thr Gly Ile Arg Glu Asp Pro Asp Val Cys Leu Lys Ala Pro
        115                 120                 125

<210> SEQ ID NO 40
<211> LENGTH: 343
<212> TYPE: PRT
<213> ORGANISM: Homo sapiens
```

```
<400> SEQUENCE: 40

Met Asp Ala Pro Lys Ala Gly Tyr Ala Phe Glu Tyr Leu Ile Glu Thr
1               5                   10                  15

Leu Asn Asp Ser Ser His Lys Lys Phe Phe Asp Val Ser Lys Leu Gly
            20                  25                  30

Thr Lys Tyr Asp Val Leu Pro Tyr Ser Ile Arg Val Leu Leu Glu Ala
        35                  40                  45

Ala Val Arg Asn Cys Asp Gly Phe Leu Met Lys Lys Glu Asp Val Met
    50                  55                  60

Asn Ile Leu Asp Trp Lys Thr Lys Gln Ser Asn Val Glu Val Pro Phe
65                  70                  75                  80

Phe Pro Ala Arg Val Leu Leu Gln Asp Phe Thr Gly Ile Pro Ala Met
                85                  90                  95

Val Asp Phe Ala Ala Met Arg Glu Ala Val Lys Thr Leu Gly Gly Asp
            100                 105                 110

Pro Glu Lys Val His Pro Ala Cys Pro Thr Asp Leu Thr Val Asp His
        115                 120                 125

Ser Leu Gln Ile Asp Phe Ser Lys Cys Ala Ile Gln Asn Ala Pro Asn
130                 135                 140

Pro Gly Gly Gly Asp Leu Gln Lys Ala Gly Lys Leu Ser Pro Leu Lys
145                 150                 155                 160

Val Gln Pro Lys Lys Leu Pro Cys Arg Gly Gln Thr Thr Cys Arg Gly
                165                 170                 175

Ser Cys Asp Ser Gly Glu Leu Gly Arg Asn Ser Gly Thr Phe Ser Ser
            180                 185                 190

Gln Ile Glu Asn Thr Pro Ile Leu Cys Pro Phe His Leu Gln Pro Val
        195                 200                 205

Pro Glu Pro Glu Thr Val Leu Lys Asn Gln Glu Val Glu Phe Gly Arg
    210                 215                 220

Asn Arg Glu Arg Leu Gln Phe Phe Lys Trp Ser Ser Arg Val Leu Lys
225                 230                 235                 240

Asn Val Ala Val Ile Pro Pro Gly Thr Gly Met Ala His Gln Ile Asn
                245                 250                 255

Leu Glu Tyr Leu Ser Arg Val Val Phe Glu Glu Lys Asp Leu Leu Phe
            260                 265                 270

Pro Asp Ser Val Val Gly Thr Asp Ser His Ile Thr Met Val Asn Gly
        275                 280                 285

Leu Gly Ile Leu Gly Trp Gly Val Gly Gly Ile Glu Thr Glu Ala Val
    290                 295                 300

Met Leu Gly Leu Pro Val Ser Leu Thr Leu Pro Glu Val Val Gly Cys
305                 310                 315                 320

Glu Leu Thr Gly Ser Ser Asn Pro Phe Val Thr Ser Ile Asp Val Val
                325                 330                 335

Leu Gly Ile Thr Lys Val Ser
            340

<210> SEQ ID NO 41
<211> LENGTH: 305
<212> TYPE: DNA
<213> ORGANISM: Homo sapiens
<220> FEATURE:
<221> NAME/KEY: unsure
<222> LOCATION: (53), (54), (55), (56), (57), (58)
<223> OTHER INFORMATION: A or G or C or T
```

```
<400> SEQUENCE: 41
tcatgaagtg aagccaactg tttagactag aatgttatga gattaaaccc acnnnnnntt      60
attcatagac ataaaccctc attttaatta gtggatctgg attttttgtca tatgtggaat    120 cataatttaa acaaaatcaa ctaagatgat ccaagttcca cacaactgca cttcaatatt    180
caagtcggtg tgaagatgcc tgactactgc gtcacaagat tctgagctgt cgtaaaaagc    240
ctggctcgtg gtttctattt atagtgtaca catgttgggt tataatcaca aacctggaac    300
tctgt                                                                305

<210> SEQ ID NO 42
<211> LENGTH: 256
<212> TYPE: DNA
<213> ORGANISM: Homo sapiens

<400> SEQUENCE: 42
gaaaccacgg cttcacccta gagacagcat tcagatatag acgggatact tgtgttagtc      60
agttccttta taacaggtga atctctctcc cactgcttca acactgcgtg acaaagccaa    120
ttgggaagca gctttacaaa tgtgacttga cttggggatc ttcttgatac tttgccatgg    180
caaggaacaa gccgcctgaa ctaaatgcca ctccatttga ttccacgctt aaagtaacca    240
tgcaaccgac tatagt                                                    256

<210> SEQ ID NO 43
<211> LENGTH: 244
<212> TYPE: DNA
<213> ORGANISM: Homo sapiens
<220> FEATURE:
<221> NAME/KEY: unsure
<222> LOCATION: (227), (237)
<223> OTHER INFORMATION: A or G or C or T

<400> SEQUENCE: 43
tactcttcaa ccatgatttt tctctgatgg cctgtgtgaa cagattaatg gtgtccatct      60
aattccttcc ccactggggg aaagcaaatc atcaggccca ttgcaaaaac tgctcttggt    120
tgagcttcct gccttaaatc atacccacag tgaatggcgt cccttatca ccgctaatga     180 ctctgacatc tctctccact cacatgtgag cctcctcagc tctcganaaa caagtcngtc    240
tcgg                                                                 244

<210> SEQ ID NO 44
<211> LENGTH: 258
<212> TYPE: DNA
<213> ORGANISM: Homo sapiens
<220> FEATURE:
<221> NAME/KEY: unsure
<222> LOCATION: (39), (40), (41)
<223> OTHER INFORMATION: A or G or C or T

<400> SEQUENCE: 44
tctcagaaaa ctccagatca aatgagatga gtatggtgnn nagggctggc aattagagga     60
tactctccaa tggtgatgaa gggagatgtc tggggaaat ccagcaggat gttgatttag    120
tatgtacaca gtgagaggat acttgtagag aacctagaat cttctctgaa tgtgacgggc   180
cctcagagat aattgttaac agataagtgg atgattaaat acacttcctc cagtaggcta   240
gatgttaaga cggagatc                                                 258
```

```
<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 45
gggcttaata ttattcatag atcgag                                          26

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 46
gttattatac tatcaagtaa cccaac                                          26

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 47
gtggatctgg atttttgtca tatgt                                           25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 48
gtttgtgatt ataccccaac atgtg                                           25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 49 gaagggaag agacattaaa ttatc                                            25

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 50
gcttctaaat ctcctgagtc actt                                            24
```

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 51
gacaatgagt aagaagaaag aggg                                         24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 52
gtccagtccc ttggtttatt tgtc                                         24

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 53
ggtacccagt ttcaaattaa catgg                                        25

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 54
gattcttcaa ctgccaaact tgttc                                        25

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 55
gctgatgctt ttctatctga cttc                                         24

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 56
gaccaggact gaacagaggt ga                                           22

```
<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 57
gcttatagac catgtttgta gtagg                                         25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 58
gtgaacaaat gctaaatcag acatg                                         25

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 59
gccacgggtt tcccatatcg aa                                            22

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 60
gactatactt aggaacctct gcaa                                          24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 61
gttctgctct cagcagattg gtta                                          24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 62
gccaacatct gaactaaata ctgc                                          24
```

```
<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 63
gttcagtgaa tgttacctag aaaca                                              25

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 64
ggagtgaaaa ctgtcttgtt catc                                               24

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 65
gtatgacaaa tagtttctgc ctgat                                              25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 66
gattaacaaa gatgtacaga ctgag                                              25

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 67
gagacagcat tcagatatag acgg                                               24

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 68
gcgtggaatc aaatggagtg gc                                                 22
```

```
<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 69
gatggcctgt gtgaacagat taat                                            24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 70
gagagagatg tcagagtcat tagc                                            24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 71
gatccccaca atttcttgtg attg                                            24

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 72
gttcccctaa aataatgtgg taatg                                           25

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 73
gaggatactc tccaatggtg atg                                             23

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 74
gtcttaacat ctagcctact ggag                                            24
```

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 75
gagaggagcc atgtatacaa acca                                      24

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 76
gcacgcagga tcagatatag taattc                                    26

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 77
gctgaaacct aagctgaagg aagg                                      24

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 78
gtccctcacc tcagatcaca cc                                        22

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 79
gctatctacc tggcaggaaa agag                                      24

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 80
gagtttctta ctatgatctg gattc                                     25

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 81
gcaaaatgta ctcagcttca atcac                                          25

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 82
gtaaatgcag tactgttctg atcc                                           24

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 83
gaatgcttca ttctcattgt ttaagg                                         26

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 84
gtcactagga ttccacagaa cttc                                           24

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 85
gaggtagggc ttcccttcgc ta                                             22

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 86
gcataacaag tgacagggtt agtta                                          25

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 87
ggtgctcctt ccttacactg gt                                          22

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 88
gactacacat aaacccaccc cag                                         23

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 89
gggtacagga tttctaagaa gtgg                                        24

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 90
ggagaaaatt tcagctcatc tgaag                                       25

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 91
gctgaagtta agcattaata cgcc                                        24

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 92
gcggctgtaa tgtgcaatga tgt                                         23

```
<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 93
gacagcaacc taataacagc tgtc                                              24

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 94
gtcctaggca cttgtcacta gg                                                22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 95 gagggggactt ccaagagtct ct                                               22

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 96
gtcttcagga aaattgtagt tacag                                             25

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 97
gttacaaaca cacgaagt tcct                                                24

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 98
gacttcctaa ggcacactca gc                                                22
```

```
<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 99
gtttaactac ctctcaggtc atga                                          24

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 100
gtcgccaagg ctgtagtgca at                                            22

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 101
gaaataggta tcccttgatg tcga                                          24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 102
gaccaagaat tcagttcatc agtt                                          24

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 103
gaatgaacca gagccaggac ag                                            22

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 104
gccttgtatg tatgcctgtg cc                                            22
```

```
<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 105
aagagtccac caggccatgg a                                              21

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 106
taccttgtgt acttctagct gag                                            23

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 107
gttttttttt ttttta                                                    17

<210> SEQ ID NO 108
<211> LENGTH: 17
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 108
gttttttttt tttttg                                                    17

<210> SEQ ID NO 109
<211> LENGTH: 17
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 109
gttttttttt tttttc                                                    17

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 110
cagagtgatg gatatcaa                                                  18
```

```
<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 111
atgaaagtgc cagtgtgcca tg                                              22

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 112
cccatcacca tcttccagga gc                                              22

<210> SEQ ID NO 113
<211> LENGTH: 26
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 113
ttcaccacct tcttgatgtc atcata                                          26

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 114

Cys Pro Leu Lys Arg Glu Asp Gly Phe Phe Thr Arg Thr Asp Ile
  1               5                  10                  15

<210> SEQ ID NO 115
<211> LENGTH: 16
<212> TYPE: PRT
<213> ORGANISM: Artificial Sequence
<220> FEATURE:
<221> NAME/KEY: MOD_RES
<222> LOCATION: (16)
<223> OTHER INFORMATION: AMIDATION, GluAmide

<400> SEQUENCE: 115

Cys Ser Phe Leu Glu Lys Phe Asn Lys Ser Lys Arg Glu Arg Leu Xaa
  1               5                  10                  15

<210> SEQ ID NO 116
<211> LENGTH: 15
<212> TYPE: PRT
<213> ORGANISM: Artificial Sequence
<220> FEATURE:
<221> NAME/KEY: MOD_RES
<222> LOCATION: (15)
<223> OTHER INFORMATION: AMIDATION, GlyAmide
```

-continued

```
<400> SEQUENCE: 116

Cys Ala Glu His Trp Ser Gly Glu Phe Glu Lys Trp Lys Val Xaa
 1               5                  10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 117

Cys Glu Ile Asp Lys Arg Val Ser Leu Ile Leu His Phe Gly Lys Phe
 1               5                  10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 118

Cys Arg Leu Met Lys Arg Lys Thr Gly Glu Ser Leu Leu Ser Ser
 1               5                  10                  15

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 119

Cys Thr Ser Ile Asp Val Val Leu Gly Ile Thr Lys Val Ser
 1               5                  10

<210> SEQ ID NO 120
<211> LENGTH: 16
<212> TYPE: PRT
<213> ORGANISM: Artificial Sequence
<220> FEATURE:
<221> NAME/KEY: MOD_RES
<222> LOCATION: (16)
<223> OTHER INFORMATION: AMIDATION, LysAmide

<400> SEQUENCE: 120

Cys Ser Ala Glu Thr Ala Pro Gly Val His Lys Arg Tyr Phe Arg Xaa
 1               5                  10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 121

Cys Lys Ile Thr Glu Lys Gln Leu Leu Gly Asn Val Leu Asn Tyr Pro
 1               5                  10                  15
```

IGA NEPHROPATHY-RELATED DNA

CROSS-REFERENCE TO RELATED APPLICATION

This is a continuation-in-part application of U.S. patent application Ser. No. 09/090,672 filed on Jun. 4, 1998, which is a continuation-in-part application of PCT/JP97/04468 filed on Dec. 5, 1997.

BACKGROUND OF THE INVENTION

1. Field of the Invention

The present invention relates to a novel DNA whose expression level fluctuates in leukocytes of IgA nephropathy patients in comparison with leukocytes of healthy persons, a process for isolating the DNA, a novel protein encoded by the DNA, an antibody recognizing the protein, a method for detecting the protein or the DNA, and methods of diagnosis and treatment of IgA nephropathy.

2. Brief Description of the Background Art

IgA nephropathy is a chronic glomerulonephritis which is characterized in that an IgA immune complex considered to be derived from blood deposits in glomerulus of the kidney. In Japan, the IgA nephropathy occupies 30% or more of primary renal diseases, having the highest frequency as a single renal disease, and 15 to 30% of the disease becomes renal failure due to poor prognosis. However, since the cause of the disease of IgA nephropathy is still unclear, a fundamental therapeutic method has not been found. Additionally, definite diagnosis of IgA nephropathy imposes heavy burden on patients, because the method is carried out by taking out a portion of the kidney by biopsy and recognizing deposition of the IgA immune complex in mesangium by means of immunological staining.

It has been reported that about 50% of the patients with IgA nephropathy have a high blood IgA level [*Diseases of the Kidney*, 5th edition (1993), *Nephron*, 29, 170 (1981)]. It is considered that B cells relate to the production of IgA in blood and T cells relate to the regulation of the production. Furthermore, it has been reported that the production of cytokine, such as interleukin 4, interleukin 5, interleukin 6 or TGF-β (transforming growth factor-β), is high in peripheral T cells of IgA nephropathy patients in comparison with healthy persons [*Clinical & Experimental Immunology*, 103, 125 (1996), *Kidney International*, 46, 862 (1994)] and that integrin, such as VLA (very late activation)-4 and VLA-5, are strongly activated in peripheral lymphocytes of IgA nephropathy patients [*Nephrology, Dialysis, Transplantation*, 10, 1342 (1995)]. On the basis of these facts, it is considered that, in IgA nephropathy, the production of IgA becomes excess due to abnormality in the immune system, the resulting IgA immune complex in blood deposits on the glomerulus, and activation of the complement system caused thereby and the like exert influence upon disorders of the glomerulus, but the cause of IgA nephropathy has not been reported.

SUMMARY OF THE INVENTION

Elucidation of the cause of IgA nephropathy and its treatment or diagnosis which can reduce a burden on patients are expected.

A novel DNA related to IgA nephropathy, a method for isolating the DNA, a novel protein related to IgA nephropathy, a method for producing the protein, an antibody recognizing the protein, and a therapeutic drug and a diagnostic drug using the above-described protein, DNA or antibody are desired.

The present invention is useful for these objects.

The present invention relates to the following (1) to (21):

(1) A DNA related to IgA nephropathy comprising a nucleotide sequence selected from the nucleotide sequences represented by SEQ ID NO:1 to NO:33 and SEQ ID NO:41 to NO:44, or, a DNA which hybridizes with said DNA under stringent conditions.

(2) A DNA comprising a nucleotide sequence identical to continuous 5 to 60 residues in a nucleotide sequence selected from the nucleotide sequences represented by SEQ ID NO:1 to NO:33, or a DNA comprising a sequence complementary to said DNA.

(3) The DNA according to claim 2, comprising a nucleotide sequence selected from the nucleotide sequences represented by SEQ ID NO:45 to NO:106.

(4) A method for detecting mRNA of an IgA nephropathy-related gene using the DNA according to any one of (1) to (3).

(5) An IgA nephropathy diagnostic agent comprising the DNA according to any one of (1) to (3).

(6) A method for inhibiting transcription of an IgA nephropathy-related gene or translation of mRNA of an IgA nephropathy-related gene using the DNA according to (2) or (3).

(7) An IgA nephropathy therapeutic agent comprising the DNA according to (2) or (3).

(8) A method for isolating a DNA related to IgA nephropathy from leukocytes of a patient with IgA nephropathy comprising conducting a differential display method.

(9) A protein comprising an amino acid sequence selected from the amino acid sequences represented by SEQ ID NO:34 to NO:40, or a protein comprising an amino acid sequence in which one or several amino acids are deleted, substituted or added in the amino acid sequence of said protein, and having an activity related to IgA nephropathy.

(10) A DNA encoding the protein according to (9).

(11) A recombinant DNA obtained by inserting the DNA according to (10) into a vector.

(12) A transformant obtained by introducing the recombinant DNA according to (11) into a host cell.

(13) A method for producing the protein according to (9), comprising: culturing the transformant according to (12) in a medium to produce and accumulate said protein in the culture; and recovering said protein from the resulting culture.

(14) An antibody which recognizes the protein according to (9).

(15) A method for immunologically detecting the protein according to (9) using the antibody according to (14).

(16) An IgA nephropathy diagnostic agent comprising the antibody according to (14).

(17) An IgA nephropathy therapeutic agent comprising the antibody according to (14).

(18) A composition comprising the DNA according to any one of (1) to (3) and a diagnostic acceptable carrier.

(19) A composition comprising the DNA according to (1) or (3) and a pharmaceutical acceptable carrier.

(20) A composition comprising the antibody according to (14) and a diagnostic acceptable carrier.

(21) A composition comprising the antibody according to (14) and a pharmaceutical acceptable carrier.

BRIEF EXPLANATION OF THE DRAWINGS

FIG. 3 is a graph showing the binding reactivity of rat antisera, which were obtained by immunizing rats with a conjugate of a peptide (Compound 3) having the amino acid sequence represented by SEQ ID NO:116 with KLH, to Compound 3 examined by the enzyme immunoassay. The binding reactivity to Compound 3 is shown in the left, while the binding reactivity to a control peptide is shown in the right. R1 to R3 and NRS show antisera of 3 rats immunized with Compound 3 and a normal rat serum, respectively.

FIG. 4 is a graph showing the binding reactivity of rat antisera, which were obtained by immunizing rats with a conjugate of a peptide (Compound 4) having the amino acid sequence represented by SEQ ID NO:117 with KLH, to Compound 4 examined by the enzyme immunoassay. The binding reactivity to Compound 4 is shown in the left, while the binding reactivity to a control peptide is shown in the right. R1 to R3 and NRS show antisera of 3 rats immunized with Compound 4 and a normal rat serum, respectively.

DETAILED DESCRIPTION OF THE INVENTION

Figure 1:
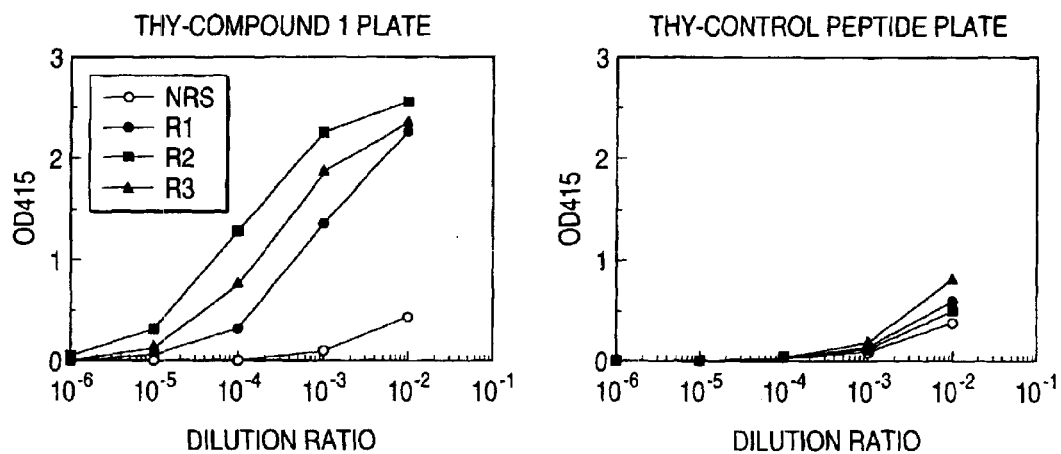
FIG. 1 is a graph showing the binding reactivity of rat antisera, which were obtained by immunizing rats with a conjugate of a peptide (Compound 1) having the amino acid sequence represented by SEQ ID NO:114 with KLH (manufactured by Calbiochem), to Compound 1 examined by the enzyme immunoassay. The binding reactivity to Compound 1 is shown in the left, while the binding reactivity to a control peptide is shown in the right. R1 to R3 and NRS show antisera of 3 rats immunized with Compound 1 and a normal rat serum, respectively.

This application is based on Japanese application No. 8-325763 filed on Dec. 5, 1996, PCT/JP97/04468 filed on Dec. 5, 1997, and U.S. patent application Ser. No. 09/090, 672 filed on Jun. 4, 1998, the entire contents of which are incorporated hereinto by reference.

The DNA of the present invention is a IgA nephropathy-related DNA. Examples include a DNA comprising a nucleotide sequence selected from the nucleotide sequences represented by SEQ ID NO:1 to NO:33 and SEQ ID NO:41 to NO:44, and a DNA which hybridizes with the DNA under stringent conditions.

The DNA which hybridizes under stringent conditions with a DNA comprising a nucleotide sequence selected from the nucleotide sequences represented by SEQ ID NO:1 to NO:33 and SEQ ID NO:41 to NO:44 means a DNA which is obtained by colony hybridization, plaque hybridization, Southern blot hybridization or the like using, as a probe, a DNA comprising a nucleotide sequence selected from the nucleotide sequences represented by SEQ ID NO:1 to NO:33 and SEQ ID NO:41 to NO:44. Examples include DNA which can be identified by carrying out hybridization at 65° C. in the presence of 0.7–1.0 M NaCl using a filter on which a DNA prepared from colonies or plaques is immobilized, and then washing the filter with 0.1× to 2×SSC solution (the composition of 1×SSC comprises 150 mM sodium chloride and 15 mM sodium citrate) at 65° C.

The hybridization can be carried out in accordance with known methods described in, for example, *Molecular Cloning, A Laboratory Manual,* Second Edition, Cold Spring Harbor Laboratory Press (1989) (referred to as "*Molecular Cloning,* 2nd ed." hereinafter), *Current Protocols in Molecular Biology,* John Wiley & Sons (1987–1997) (referred to as "*Current Protocols in Molecular Biology*" hereinafter), *DNA Cloning 1: Core Techniques, A Practical Approach,* Second Edition, Oxford University (1995) or the like. Specific examples of the DNA which can be hybridized include a DNA having a homology of 60% or more with a nucleotide sequence selected from the nucleotide sequences represented by SEQ ID NO:1 to NO:33 and SEQ ID NO:41 to NO:44, preferably a DNA having a homology of 80% or more, and more preferably a DNA having a homology of 95% or more.

Also, the DNA of the present invention includes an oligonucleotide and antisense oligonucleotide containing a partial sequence of the IgA nephropathy-related DNA.

Examples of the oligonucleotide include oligonucleotides comprising a sequence identical to a sequence of continuous 5 to 60 residues, preferably continuous 10 to 50 residues, in a nucleotide sequence selected from the nucleotide sequences represented by SEQ ID NO:1 to NO:33 and SEQ ID NO:41 to NO:44. Examples of the antisense oligonucleotide include antisense oligonucleotides of the oligonucleotides. Specific examples include oligonucleotides comprising a nucleotide sequence selected from the nucleotide sequences represented by SEQ ID NO:45 to NO:106.

Examples of the protein of the present invention include proteins having an activity related to IgA nephropathy. Specific examples include a protein comprising an amino acid sequence selected from the amino acid sequences represented by SEQ ID NO:34 to NO:40, and a protein comprising an amino acid sequence in which one or several amino acids are deleted, substituted or added in the amino acid sequence of said protein and having an activity related to IgA nephropathy.

The protein comprising an amino acid sequence in which one or several amino acids are deleted, substituted or added in the amino acid sequence of the protein that has an amino acid sequence selected from the amino acid sequences represented by SEQ ID NO:34 to NO:40 and having an activity related to IgA nephropathy can be prepared in accordance with known methods described in, for example, *Molecular Cloning*, 2nd ed., *Current Protocols in Molecular Biology, Nucleic Acids Research,* 10, 6487 (1982), *Proc. Natl. Acad. Sci. USA,* 79, 6409 (1982), *Gene,* 34, 315 (1985), *Nucleic Acids Research,* 13, 4431 (1985), *Proc. Natl. Acad. Sci. USA,* 82, 488 (1985) and the like. The number of the amino acids which are deleted, substituted or added is not particularly limited; however, they are preferably one to decades, more preferably one to several, amino acids. Also, in order that the polypeptide of the present invention has an activity relating to IgA nephropathy, it is preferred that they have a homology of at least 60% or more, generally 80% or more, and particularly 95% or more, with an amino acid sequence selected from the amino acid sequences represented by SEQ ID NO:34 to NO:40.

Examples of the antibody of the present invention include antibodies which recognize the above-described proteins.

The present invention is described in detail.

1. Preparation of IgA Nephropathy-Related DNA

Taking note of the difference in the expression quantity of mRNA in leukocytes between patients with IgA nephropathy and healthy persons, the IgA nephropathy-related DNA is isolated using the differential display method [*FEBS Letters,* 351, 231 (1994)]. That is, an amplified cDNA fragment of a novel gene (referred to as "IgA nephropathy-related gene" hereinafter) whose expression level increases or decreases significantly in leukocytes of a patient with IgA nephropathy as compared with leukocytes of a healthy person is obtained by subjecting total RNA or mRNA extracted from cells to the polymerase chain reaction (PCR) using various primers.

This method is described below.

Total RNA or mRNA is prepared from leukocytes of patients with IgA nephropathy and leukocytes of healthy persons.

Examples of the method for the preparation of total RNA include guanidine thiocyanate-cesium trifluoroacetate method [*Methods in Enzymol.,* 154, 3 (1987)] and the like.

Examples of the method for preparing poly(A)$^+$ RNA from total RNA include oligo(dT)-immobilized cellulose column method (*Molecular Cloning,* 2nd ed.) and the like.

The mRNA can also be prepared using a kit, such as Fast Track mRNA Isolation Kit (manufactured by Invitrogen), Quick Prep mRNA Purification Kit (manufactured by Pharmacia) or the like.

Using an anchor primer, cDNA is synthesized in the usual way from the RNA extracted by the above-described method from leukocytes of a patient with IgA nephropathy or leukocytes of a healthy person, and then the cDNA is amplified by subjecting it to PCR using an anchor primer having a 5'-end labeled with fluorescence and an arbitrary primer.

The anchor primer is a primer in which an oligonucleotide of adenine, guanine or cytosine, excluding thymidine, is added to the 3'-end of an oligo(dT) sequence which hybridizes with a 3'-end poly(A) sequence of mRNA, and the primer can be synthesized using DNA Synthesizer Model 392 (manufactured by Perkin-Elmer) or the like.

The arbitrary primer is an oligonucleotide which amplifies various cDNA sequences and can yield a large number of amplified DNA fragments by a single reaction. Examples include OPD-1 to 20, OPE-1 to 20, OPV-1 to 20 (manufactured by Operon Technologies), and the like. Preferably, the arbitrary primer may have a length of about 10 bases.

Each of the DNA amplified by PCR is subjected to polyacrylamide gel electrophoresis, and the amount of fluorescence of the resulting bands is measured using Fluoro Imager (manufactured by Molecular Dynamics).

By comparing intensities of fluorescence of respective bands, a portion of the gel, which corresponds to the position of band where the intensities of fluorescence are fluctuated between the IgA nephropathy patient and healthy person, is cut off and the DNA fragment contained in the gel is amplified by PCR.

The nucleotide sequence of the DNA is determined by inserting the amplified DNA fragment into a vector, directly or after blunt-ending its termini using a DNA polymerase, in the usual way and then analyzing it by a usually used nucleotide sequence analyzing method such as the dideoxy method of Sanger et al. [*Proc. Natl. Acad. Sci. USA,* 74, 5463 (1977)] or using a nucleotide sequence analyzer such as 373A DNA Sequencer (manufactured by Perkin Elmer) or the like.

Examples of the vector used for the integration of the amplified DNA fragment include pBluescript KS(+) (manufactured by Stratagene), pDIRECT [*Nucleic Acids Research,* 18, 6069 (1990)], pCR-Script Amp SK(+) [manufactured by Stratagene, *Strategies,* 5, 6264 (1992)], pT7Blue (manufactured by Novagen), pCR II [manufactured by Invitrogen, Biotechnology, 9, 657 (1991)], pCR-TRAP (manufactured by Genehunter), pNo-TA$_{T7}$ (manufactured by 5'→3') and the like.

Novelty of the nucleotide sequence determined in this manner can be verified by searching a data base, such as GenBank, EMBL, DDBJ and the like, using a homology searching program, such as blast and the like, thereby finding that there is no nucleotide sequence which shows an obvious homology that coincides with the nucleotide sequences in the data base.

Examples of the thus obtained partial DNA fragment of cDNA of the IgA nephropathy-related gene include DNA comprising a nucleotide sequence selected from the nucleotide sequences represented by SEQ ID NO:8 to NO:33 and SEQ ID NO:41 to NO:44.

When the DNA obtained by the above-described method is a partial DNA fragment of cDNA which corresponds to IgA nephropathy-related mRNA, full length cDNA can be obtained by the following method (1) or (2) using the DNA obtained by the above-described method.

(1) Application of cDNA Library

A full length cDNA can be obtained by carrying out screening according to hybridization using the above-described DNA fragment as the probe and various cDNA libraries.

The method for the preparation of cDNA libraries is described below.

Examples of the method for the preparation of cDNA libraries include methods described in *Molecular Cloning,* 2nd. ed., *Current Protocols in Molecular Biology,* or *DNA Cloning* 1: *Core Techniques, A Practical Approach,* Second Addition, Oxford University Press (1995), etc. or methods using a commercially available kit, such as SuperScript Plasmid System for cDNA Synthesis and Plasmid Cloning (manufactured by Gibco BRL) or ZAP-cDNA Synthesis Kit (manufactured by Stratagene). Additionally, commercially available cDNA libraries, such as a human leukocyte cDNA library (manufactured by Life Technologies) and the like, can also be used.

In preparing the cDNA library, any one of phage vectors, plasmid vectors and the like can be used as the cloning vector which replicates autonomously in *Escherichia coli* K12. Examples include ZAP Express [manufactured by Stratagene, *Strategies,* 5, 58 (1992)], pBluescript II SK(+) [*Nucleic Acids Research,* 17, 9494 (1989)], λ zap II (manufactured by Stratagene), λgt10, λgt11 [*DNA Cloning, A Practical Approach,* 1, 49 (1985)], λTriplEx (manufactured by Clontech), λBlueMid (manufactured by Clontech), λExCell (manufactured by Pharmacia), pcD2 [*Mol. Cell. Biol.,* 3, 280 (1983)], pUC18 [*Gene,* 33, 103 (1985)], and the like.

With regard to the *Escherichia coli* used to transform with the vector containing the cDNA, any microorganism belonging to *Escherichia coli* can be used. Examples include *Escherichia coli* XL1-Blue MRF' [manufactured by Stratagene, *Strategies,* 5, 81 (1992)], *Escherichia coli* C600 [*Genetics,* 39, 440 (1954)], *Escherichia coli* Y1088 [*Science,* 222, 778 (1983)], *Escherichia coli* Y1090 [*Science,* 222, 778 (1983)], *Escherichia coli* NM522 [*J. Mol. Biol.,* 166, 1 (1983)], *Escherichia coli* K802 [*J. Mol. Biol.,* 16, 118 (1966)], *Escherichia coli* JM105 [*Gene,* 38, 275 (1985)], and the like.

A cDNA clone can be selected from the cDNA library according to a colony hybridization or plaque hybridization method (*Molecular Cloning,* 2nd ed.) using a probe labeled with an isotope or digoxigenin.

The DNA of interest can be obtained from the thus selected clone in the usual way.

(2) The DNA of interest can also be obtained by the 5'-RACE (rapid amplification of cDNA ends) and 3'-RACE method [Proc. Natl. Acad. Sci. USA, 85, 8998 (1988)] in which cDNA is synthesized from mRNA by the above-described method, adapters are added to both ends of the cDNA and then PCR is carried out using primers based on the nucleotide sequence of the adapter and the nucleotide sequence of the amplified fragment.

The nucleotide sequence of the DNA obtained by these methods can be determined by the above-described nucleotide sequence determining method. Novelty of the sequence can also be verified by the above-described method.

Examples of the novel full length cDNA of the IgA nephropathy-related gene obtained in this manner include DNAs having the nucleotide sequences represented by SEQ ID NO:1 to NO:7.

Once a DNA of IgA nephropathy-related gene is obtained and a nucleotide sequence thereof is determined in the above-described manner, the DNA of interest can be obtained by PCR [*PCR Protocols,* Academic Press (1990)] by preparing primers based on the nucleotide sequence and using cDNA synthesized from the mRNA or a cDNA library as the template. Alternatively, the DNA of interest may be prepared by chemical synthesis using a DNA synthesizer based on the determined DNA nucleotide sequence. Examples of the DNA synthesizer include DNA Synthesizer Model 392 (manufactured by Perkin-Elmer) using the phosphoramidite method.

On the basis of the nucleotide sequence information of the DNA and DNA fragments isolated according to the above methods, an oligonucleotide having a partial sequence of the IgA nephropathy-related DNA and a corresponding antisense oligonucleotide can be prepared according to the usual methods described in *Molecular Cloning,* 2nd ed. etc. or a DNA synthesizer using the nucleotide sequence information of the DNA.

Examples of the oligonucleotide include DNA comprising a sequence which is the same as continuous 5 to 60 nucleotides in a nucleotide sequence of the above DNA, and DNA comprising a sequence complementary to the DNA. Specific examples include DNA comprising a continues 5 to 60 nucleotides in a nucleotide sequence represented by SEQ ID NO:1 to NO:7, and DNA having a sequence complementary to the DNA.

As the sense primer and antisense primer, the above-described oligonucleotides in which melting point ($T_m$) and the number of bases are not significantly different from each other are preferred. Specific examples include oligonucleotides comprising a nucleotide sequence selected from the nucleotide sequences represented by SEQ ID NO:45 to NO:106 and the like.

Also, analogues of these oligonucleotide (hereinafter also referred to as "analogous oligonucleotides") can also be used as the oligonucleotide of the present invention.

Examples of the analogous oligonucleotides include analogous oligonucleotides in which a phosphodiester bond in an oligonucleotide is converted to a phosphorothioate bond, analogous oligonucleotides in which a phosphodiester bond in an oligonucleotide is converted to an N3'-P5' phosphoamidate bond, analogous oligonucleotides in which ribose and a phosphodiester bond in an oligonucleotide is converted to a peptide nucleic acid bond, analogous oligonucleotides in which uracil in an oligonucleotide is replaced with C-propynyluracil, analogous oligonucleotides in which uracil in an oligonucleotide is replaced with C-5 thiazoluracil, analogous oligonucleotides in which cytosine in an oligonucleotide is replaced with C-5 propynylcytosine, analogous oligonucleotides in which cytosine in an oligonucleotide is replaced with phenoxazin-modified cytosine, analogous oligonucleotides in which ribose in an oligonucleotide is replaced with 2'-O-propylribose, analogous oligonucleotides in which ribose in an oligonucleotide is replaced with 2'-methoxyethoxyribose, and the like [*Cell Engineering,* 16, 1463 (1997)].

2. Production of Protein Having an Activity Related to IgA Nephropathy

The full length cDNA of IgA nephropathy-related gene obtained by the method described in the above section 1 encodes a protein having an activity related to IgA nephropathy (referred to as "IgA nephropathy-related protein" hereinafter).

The IgA nephropathy-related protein of the present invention can be prepared by expressing the IgA nephropathy-related gene in a host cell using the method described in *Molecular Cloning,* 2nd ed., *Current Protocols in Molecular Biology,* and the like, for example, according to the following method.

A DNA fragment having a suitable length containing a portion encoding the protein (hereinafter referred to as "IgA nephropathy protein-encoding DNA") is prepared from the full length cDNA as occasion demands.

Also, DNA in which nucleotides in a nucleotide sequence at a part encoding the protein of the present invention are replaced to give a codon suitable for expression of the host cell as occasion demands. The DNA is useful for efficiently producing the protein of the present invention.

An expression plasmid of the protein is prepared by inserting the DNA fragment or the full length cDNA into a downstream site of the promoter in the expression vector.

As the host cell, bacteria, yeasts, animal cells, insect cells, plant cells, and the like can be used so long as they can express the gene of interest.

Examples of the expression vector include those which can replicate autonomously in the above-described host cell or can be integrated into chromosome and have a promoter at such a position that the IgA nephropathy protein-encoding DNA can be transcribed.

When a bacterium or the like is used as the host cell, it is preferred that the IgA nephropathy protein-encoding DNA expression vector can replicate autonomously in the bacterium and is a recombinant vector constructed with a promoter, a ribosome binding sequence, the IgA nephropathy protein-encoding DNA and a transcription termination sequence. A promoter controlling gene can also be contained.

Examples of the expression vector include pBTrp2, pBTac1 and pBTac2 (all available from Boehringer Mannheim Co.), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agric. Biol. Chem.*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(–) (manufactured by Stratagene), pTrs30[prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM B-400), Japanese Published Unexamined Patent Application No. 221091/85], pGKA2 [*Escherichia coli* IGKA2 (FERM BP-6798), Japanese Published Unexamined Patent Application No. 221091/85], pTerm2 (U.S. Pat. Nos. 4,686,191, 4,939,094 and 5,160,735), pSupex, pUB110, pTP5, pC194, pEG400 [*J. Bacteriol.*, 172, 2392 (1990)], pGEX (manufactured by Pharmacia), pET system (manufactured by Novagen), and the like.

With regard to the promoter, any promoter can be used so long as it can function in the host cell. Examples include promoters originated from *Escherichia coli*, phage and the like, such as trp promoter (Ptrp), lac promoter (Plac), $P_L$ promoter, $P_R$ promoter, T7 promoter and the like, SPO1 promoter, SPO2 promoter, penP promoter and the like. Also, artificially designed and modified promoters, such as a promoter in which two Ptrp are linked in series (Ptrp×2), tac promoter, letI promoter [*Gene*, 44, 29 (1986)] and lacT7 promoter and the like, can be used.

It is preferred to use a plasmid in which the space between Shine-Dalgarno sequence which is the ribosome binding sequence and the initiation codon is adjusted to an appropriate distance (for example, 6 to 18 bases).

The transcription termination sequence is not always necessary for the expression of the IgA nephropathy-related gene of the present invention. However, it is preferred to arrange the transcription terminating sequence at just downstream of the structural gene.

Examples of the host cell include microorganisms belonging to the genus *Escherichia*, *Serratia*, *Bacillus*, *Brevibacterium*, *Corynebacterium*, *Microbacterium*, *Pseudomonas*, and the like. Specific examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Escherichia coli* GI698, *Escherichia coli* TB1, *Serratia ficaria*, *Serratia fonticola*, *Serratia liquefaciens*, *Serratia marcescens*, *Bacillus subtilis*, *Bacillus amyloliquefaciens*, *Brevibacterium ammoniagenes*, *Brevibacterium immariophilum* ATCC 14068, *Brevibacterium saccharolyticum* ATCC 14066, *Brevibacterium flavunm* ATCC 14067, *Brevibacterium lactofermentum* ATCC 13869, *Corynebacterium glutamicum* ATCC 13032, *Corynebacterium glutamicum* ATCC 13869, *Corynebacterium acetoacidophilum* ATCC 13870, *Microbacterium ammoniaphilum* ATCC 15354, *Pseudomonas putida*, *Pseudomonas* sp. D-0110 and the like.

With regard to the method for the introduction of the recombinant vector, any method for introducing DNA into the above-described host cells, such as a method in which calcium ion is used [*Proc. Natl. Acad. Sci. USA*, 69, 2110 (1972)], a protoplast method (Japanese Published Unexamined Patent Application No. 2483942/88), the methods described in *Gene*, 17, 107 (1982) and *Molecular & General Genetics*, 168, 111 (1979) and the like, can be used.

When yeast is used as the host cell, examples of expression vector include YEp13 (ATCC 37115), YEp24 (ATCC 37051), YCp50 (ATCC 37419), pHS19, pHS15, and the like.

Any promoter can be used so long as it can drive the expression in yeast. Examples include a promoter of a gene in the glycolytic pathway, such as hexose kinase and the like, PHO5 promoter, PGK promoter, GAP promoter, ADH promoter, gal 1 promoter, gal 10 promoter, a heat shock protein promoter, MF al promoter, CUP 1 promoter, and the like.

Examples of the host cell include microorganisms belonging to the genus *Saccharomyces*, the genus *Schizosaccharomyces*, the genus *Kluyveromyces*, the genus *Trichosporon*, the genus *Schwanniomyces*, the genus *Pichia*, the genus *Candida* and the like. Specific examples include *Saccharomyces cerevisiae*, *Schizosaccharomyces pombe*, *Kluyveromyces lactis*, *Trichosporon pullulans*, *Schwanniomyces alluvius*, *Candida utilis* and the like.

With regard to the method for the introduction of the recombinant vector, any method for introducing DNA into yeast, such as an electroporation method [*Methods. Enzymol.*, 194, 182 (1990)], a spheroplast method [*Proc. Natl. Acad. Sci. USA*, 75, 1929 (1978)], a lithium acetate method [*J. Bacteriol.*, 153, 163 (1983)], a method described in *Proc. Natl. Acad. Sci. USA*, 75, 1929 (1978) and the like, can be used.

When animal cells are used as the host cells, examples of expression vector include pcDNAI and pcDM8 (both available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pcDM8 [*Nature*, 329, 840 (1987)], pcDNAI/Amp (manufactured by Invitrogen), pREP4 (manufactured by Invitrogen), pAGE103 [*J. Biochem.*, 101, 1307 (1987)], pAGE210, and the like.

Any promoter can be used so long as it can function in animal cell. Examples include a promoter of IE (immediate early) gene of *cytomegalovirus* (CMV), an early promoter of SV40, a promoter of retrovirus, a metallothionein promoter, a heat shock promoter, SRα promoter, and the like. Also, the enhancer of the IE gene of human CMV may be used together with the promoter.

Examples of the host cell include human Namalwa cell, monkey COS cell, Chinese hamster CHO cell, HST5637 (Japanese Published Unexamined Patent Application No. 299/88), and the like.

With regard to the method for the introduction of the recombinant vector into animal cells, any method for introducing DNA into animal cells, such as an electroporation method [*Cytotechnology*, 3, 133 (1990)], a calcium phosphate method (Japanese Published Unexamined Patent Application No. 227075/90), a lipofection method [*Proc.*

*Natl. Acad. Sci. USA*, 84, 7413 (1987)] and the method described in *Virology*, 52, 456 (1973), can be used. Preparation and culturing of transformants can be carried out in accordance with the method described in Japanese Published Unexamined Patent Application No. 227075/90 or Japanese Published Unexamined Patent Application No. 257891/90.

When an insect cell is used as the host cell, the protein can be expressed by known methods described in, for example, *Bacurovirus Expression Vectors, A Laboratory Manual, Current Protocols in Molecular Biology*, supplement 1–38 (1987–1997) *Bio/Technology*, 6, 47 (1988), or the like.

That is, a recombinant gene transfer vector and bacurovirus are simultaneously inserted into an insect cell to obtain a recombinant virus in an insect cell culture supernatant, and then the insect cells are infected with the thus obtained recombinant virus to effect expression of the protein.

Examples of the gene introducing vector used in the method include pVL1392, pVL1393, pBlueBacIII (all manufactured by Invitrogen), and the like.

Examples of the bacurovirus include *Autographa californica* nuclear polyhedrosis virus with which insects of the family Barathra are infected, and the like.

Examples of the insect cell include *Spodoptera frugiperda* oocytes Sf9 and Sf21 (*Bacurovirus Expression Vectors, A Laboratory Manual*, W.H. Freeman and Company, New York, (1992)), *Trichoplusia ni* oocyte High 5 (manufactured by Invitrogen) and the like.

The method for the co-transfer of the above-described recombinant gene transfer vector and the above-described bacurovirus for the preparation of the recombinant virus include calcium phosphate method (Japanese Published Unexamined Patent Application No. 227075/90), lipofection method [*Proc. Natl. Acad. Sci. USA*, 84, 7413 (1987)] and the like.

When a plant cell is used as the host cell, examples of expression vector include a Ti plasmid, a tobacco mosaic virus vector, and the like.

Any promoter can be used so long as it can drive the expression in a plant cell. Examples include 35S promoter of cauliflower mosaic virus (CaMV), rice actin 1 promoter, and the like.

Examples of the host cell include plant cells and the like, such as tobacco, potato, tomato, carrot, soybean, rape, alfalfa, rice, wheat, barley, and the like.

With regard to the method for the introduction of the recombinant vector, any method for introducing DNA into plant cells, such as the *Agrobacterium* method (Japanese Published Unexamined Patent Application No. 140885/84, Japanese Published Unexamined Patent Application No. 70080/85, WO 94/00977), the electroporation method (Japanese Published Unexamined Patent Application No. 251887/85), the particle gun method (Japanese Patents 2606856 and 2517813), and the like.

With regard to the gene expression method, a secretion production, a fusion protein expression and the like can be effected in accordance with the method described in *Molecular Cloning*, 2nd ed., in addition to the direct expression.

When expressed in a yeast, an animal cell or an insect cell, a glycoprotein or glycosylated protein can be obtained.

The IgA nephropathy-related protein can be produced by culturing the transformant of the present invention obtained in the above in a culture medium to produce and accumulate the IgA nephropathy-related protein, and recovering the protein from the resulting culture.

Culturing of the transformant used in the production of the IgA nephropathy-related protein of the present invention in a culture medium is carried out in accordance with a usual method used in culturing of respective host cells.

When the transformant of the present invention is an prokaryote, such as *Escherichia coli* or the like, or an eukaryote, such as yeast or the like, the medium used in culturing of these transformants may be either a natural medium or a synthetic medium, so long as it contains a carbon source, a nitrogen source, an inorganic salt and the like which can be assimilated by the transformants and can perform culturing of the transformant efficiently.

Examples of the carbon source include those which can be assimilated by respective transformants, such as carbohydrates (for example, glucose, fructose, sucrose, molasses containing them, starch, starch hydrolysate, and the like), organic acids (for example, acetic acid, propionic acid, and the like), and alcohols (for example, ethanol, propanol, and the like).

Examples of the nitrogen source include ammonia, various ammonium salts of inorganic acids or organic acids (for example, ammonium chloride, ammonium sulfate, ammonium acetate, ammonium phosphate, and the like), other nitrogen-containing compounds, peptone, meat extract, yeast extract, corn steep liquor, casein hydrolysate, soybean meal and soybean meal hydrolysate, various fermented cells and hydrolysates thereof, and the like.

Examples of inorganic substance used in the culture medium include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is carried out under aerobic conditions by shaking culture, aeration stirring culture or the like means. The culturing temperature is preferably from 15 to 45° C., and the culturing time is generally from 16 hours to seven days. The pH of the medium is maintained at 3.0 to 9.0 during the culturing. Adjustment of the medium pH is carried out using an inorganic or organic acid, an alkali solution, urea, calcium carbonate, ammonia and the like.

Also, antibiotics (for example, ampicillin, tetracycline, and the like) may be added to the medium during the culturing as occasion demands.

When a microorganism transformed with a recombinant vector containing an inducible promoter is cultured, an inducer may be added to the medium as occasion demands. For example, isopropyl-β-D-thiogalactopyranoside (IPTG) or the like may be added to the medium when a microorganism transformed with a recombinant vector containing lac promoter is cultured, or indoleacrylic acid (IAA) or the like may by added thereto when a microorganism transformed with an expression vector containing trp promoter is cultured.

Examples of the medium used in the culturing of a transformant obtained using an animal cell as the host cell include RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 Medium [*Proceeding of the Society for the Biological Medicine*, 73, 1 (1950)], and any one of these media further supplemented with fetal calf serum.

The culturing is carried out generally at pH of 6 to 8 and at a temperature of 30 to 40° C. for a period of 1 to 7 days in the presence of 5% $CO_2$.

As occasion demands, antibiotics (for example, kanamycin, penicillin, and the like) may be added to the medium during the culturing.

Examples of the medium used in the culturing of a transformant obtained using an insect cell as the host cell, include TNM-FH medium (manufactured by Pharmingen), Sf-900 II SFM (manufactured by Life Technologies), ExCell 400 or ExCell 405 (both manufactured by JRH Biosciences), Grace's Insect Medium [*Nature,* 195, 788 (1962)], and the like.

The culturing is carried out generally at pH of 6 to 7 and at a temperature of 25 to 30° C. for a period of 1 to 5 days.

Additionally, antibiotics (for example, gentamicin, and the like) may be added to the medium during the culturing as occasion demands.

A transformant obtained by using a plant cell as the host cell can be used as the cell or after differentiating a plant cell or organ. Examples of the medium used in the culturing of the transformant include Murashige and Skoog (MS) medium, White medium, media to which a plant hormone, such as auxin, cytokinine, or the like has been added, and the like.

The culturing is carried out generally at pH of 5 to 9 and at a temperature of 20 to 40° C. for a period of 3 to 60 days.

Additionally, antibiotics (for example, kanamycin, hygromycin and the like) may be added to the medium during the culturing as occasion demands.

As described above, the protein can be produced by culturing a transformant derived from a microorganism, animal cell or plant cell containing a recombinant vector to which a DNA encoding the protein of the present invention has been inserted according to the general culturing method to produce and accumulate the protein, and recovering the protein from the resulting culture.

With regard to the gene expression method, a secretion production, a fusion protein expression and the like can be effected in accordance with the method described in *Molecular Cloning,* 2nd ed., in addition to the direct expression.

The method for producing the protein of the present invention includes a method of intracellular expression in a host cell, a method of extracellular secretion from a host cell, or a method of production on a host cell membrane outer envelope. The method can be selected by changing the used host cell or the structure of the produced protein.

When the protein of the present invention is produced in a host cell or on a host cell membrane outer envelope, the protein can be positively secreted extracellularly according to the method of Paulson et al. [*J. Biol. Chem.,* 264, 17619 (1989)], the method of Lowe et al. [*Proc. of Natl. Acad. Sci. USA,* 86, 8227 (1989); *Genes Develop.,* 4, 1288 (1990)], and the methods described in Japanese Published Unexamined Patent Application No. 336963/93, WO 94/23021, and the like.

Specifically, the protein of the present invention can be positively secreted extracellularly by expressing it in the form that a signal peptide has been added to the foreground of a protein containing an active site of the protein of the present invention according to the recombinant DNA technique.

Furthermore, the production amount can be increased by utilizing a gene amplification system using a dihydrofolate reductase gene according to the method described in Japanese Published Unexamined Patent Application No. 227075/90.

Moreover, the protein of the present invention can be produced by redifferentiating a transgenic animal or plant cell to develop a transgenic animal individual (transgenic nonhuman animal) or plant individual (transgenic plant) and using the individual.

When the transformant is the animal individual or plant individual, the protein of the present invention can be produced by breeding or cultivating it to produce and accumulate the protein, and recovering the protein from the animal individual or plant individual.

Examples of the method for producing the protein of the present invention using the animal individual include a method for producing the protein of the present invention in an animal developed by inserting a gene according to a known method [*American Journal of Clinical Nutrition,* 63, 639S (1996), *American Journal of Clinical Nutrition,* 63, 627S (1996), *Bio/Technology,* 9, 830 (1991)].

In the animal individual, the protein can be produced by breeding a transgenic nonhuman animal to which the DNA encoding the protein of the present invention has been inserted to produce and accumulate the protein in the animal, and recovering the protein from the animal. Examples of the production and accumulation place in the animal include milk (Japanese Published Unexamined Patent Application No. 309192/88), egg and the like of the animal. Any promoter can be used, so long as it can drive the expression in the animal. Suitable examples include an α-casein promoter, a β-casein promoter, a β-lactoglobulin promoter, a whey acidic protein promoter, and the like, which are specific for mammary glandular cells.

Examples of the method for producing the protein of the present invention using the plant individual include a method for producing the protein of the present invention by cultivating a transgenic plant to which the DNA encoding the protein of the present invention by a known method [*Tissue Culture,* 20 (1994), *Tissue Culture,* 21 (1994), *Trends in Biotechnology,* 15, 45 (1997)] to produce and accumulate the protein in the plant, and recovering the protein from the plant.

When the protein of the present invention having an activity related to IgA nephropathy is isolated and purified from a culture of the transformant of the present invention, usual methods for the isolation and purification of enzymes may be used.

For example, when the protein of the present invention is expressed in a dissolved state inside the cells, the cells after completion of the culturing are recovered by centrifugation, suspended in a buffer of aqueous system and then disrupted using ultrasonic oscillator, French press, Manton Gaulin homogenizer, dynomill or the like to obtain a cell-free extract. A purified product can be obtained from a supernatant fluid prepared by centrifugation of the cell-free extract, by employing a technique or a combination of techniques, such as solvent extraction, salting out with ammonium sulfate or the like, desalting, precipitation with organic solvents, anion exchange chromatography using a resin [for example, diethylaminoethyl (DEAE)-Sepharose, DIAION HPA-75 (manufactured by Mitsubishi Chemical), or the like], cation exchange chromatography using a resin [for example, S-Sepharose FF (manufactured by Pharmacia), or the like], hydrophobic chromatography using a resin (for example, butyl-Sepharose, phenyl-Sepharose, or the like), gel filtration using a molecular sieve, affinity chromatography, chromatofocusing, electrophoresis (for example, isoelectric focusing).

Also, when the protein is expressed inside the cells in the form of an inclusion body, the cells are recovered, disrupted and centrifuged to thereby recover the inclusion body of the protein as a precipitated fraction.

The recovered inclusion body of the protein is solubilized using a protein denaturing agent.

The protein is renatured into a normal solid structure by diluting or dialyzing the thus-obtained solubilized solution to lower the protein denaturing agent in the solubilized solution. After this operation, a purified product of the protein is obtained by the isolation and purification method in the same manner as described above.

When the protein of the present invention or a derivative thereof, such as a sugar-modified product, is secreted extracellularly, the protein or the derivative can be recovered from the culture supernatant. That is, the purified product can be obtained by recovering culture supernatant from the culture by a technique, such as centrifugation or the like, and then subjecting the culture supernatant to the above-described isolation and purification method.

Examples of the protein obtained in this manner include proteins having an amino acid sequence selected from the amino acid sequences represented by SEQ ID NO:34 to NO:40.

Additionally, the protein expressed by the above-described method can be produced by a chemical synthesis method, such as Fmoc method (fluorenylmethyloxycarbonyl method), tBoc method (t-butyloxycarbonyl method) or the like. It can also be synthesized using a peptide synthesizer available from Sowa Boeki (manufactured by Advanced ChemTech, USA), Perkin-Elmer Japan (manufactured by Perkin-Elmer, USA), Pharmacia Biotech (manufactured by Pharmacia Biotech, Sweden), Aroka (manufactured by Protein Technology Instrument, USA), KURABO (manufactured by Synthecell-Vega, USA), Japan PerSeptive Limited (manufactured by PerSeptive, USA) or Shimadzu Corporation or the like.

3. Preparation of Antibody which Recognizes the Protein of the Present Invention (1) Preparation of Antigen A purified product of a full length or a partial fragment of the protein obtained by the method described in the above section 2 or a peptide having a partial amino acid sequence of the protein of the present invention is used as the antigen.

A partial protein sequence having 5 to 30 residues is selected as the partial peptide for the antigen. In order to obtain an antibody which recognizes the protein having a non-denatured natural structure, a partial sequence stereo-structurally present on the surface of the protein is preferably selected as the antigen peptide. The part stereostructurally present on the surface of the protein can be supposed by expecting a partial sequence having high hydrophilicity according to the method of Kyte and Doolittle [*Journal of Molecular Biology*, 157, 105–132 (1982)] and the like. Specifically, generally, a part having a low hydrophilicity is often present in the inside of the protein stereostructurally, whereas a part having a high hydrophilicity is present on the surface of the protein. Furthermore, the N-terminal and C-terminal of the protein are often present on the surface of the protein. However, the thus selected peptide is not always used as an antigen for the objective antibody.

When the partial peptide is used as the antigen, cysteine can be added to the terminal so that the peptide can be crosslinked with other protein. When the sequence inside of the protein is selected, the N-terminal and C-terminal are optionally acetylated and amidated, respectively.

The partial peptide can be synthesized by liquid-phase and solid-phase peptide synthesis methods, a method in which they are suitably combined, or a method following them [*International Journal of Peptide Protein Research*, 35, 161–214 (1990), *Methods in Enzymology*, 289, (1997), *Methods in Molecular Biology*, 35, (1994)].

Moreover, an automatic peptide synthesizer can also be used. Synthesis using the automatic peptide synthesizer can be carried out by using $N^\alpha$-Fmoc amino acid or $N^\alpha$-Boc amino acid of which side chain has been suitably protected etc. with a commercially available peptide synthesizer, such as a peptide synthesizer manufactured by Shimadzu Corporation, a peptide synthesizer manufactured by Advanced ChemTech Inc., USA (hereinafter referred to as "ACT Co."), or the like, according to a respective synthesis program. A protecting amino acid and a carrier resin as starting materials can be obtained from ABI Co., Shimadzu Corporation, Kokusan Kagaku Co., Ltd., NovaBiochem, ACT Co., AnaSpec Inc., Peptide Institute. Inc., or the like.

(2) Immunization of Animal and Preparation of Antibody (i) Production of Polyclonal Antibody A polyclonal antibody can be produced by administering the antigen obtained by the above method to an animal.

Examples of the animal to be administered include rabbits, goats, rats, mice, hamsters and the like.

Preferable dosage of antigen is 50 to 100 µg per animal.

The immunization is carried out by administering to an animal the antigen through subcutaneous, intravenous or intraperitoneal injection together with an appropriate adjuvant (for example, complete Freund's adjuvant, aluminum hydroxide gel, pertussis vaccine, or the like). When the antigen is a partial peptide, a conjugate with a carrier protein, such as BSA (bovine serum albumin), KLH (keyhole limpet hemocyanin), or the like, is produced, and it is used as the immunogen.

The administration of the antigen is carried out 3 to 10 times at the intervals of 1 or 2 weeks after the first administration. On the 3rd to 7th day after each administration, a blood sample is collected from the venous plexus of the eyeground, and it is confirmed that the serum reacts with the antigen by the enzyme immunoassay [*Antibodies—A Laboratory Manual*, Cold Spring Harbor Laboratory (1988)] or the like.

Serum is obtained from a non-human mammal having an enough antibody titer against the antigen used for the immunization, and the serum is isolated and purified to obtain a polyclonal antibody.

With regard to the method for the isolation and purification, centrifugation, salting out by 40–50% ammonium sulfate, caprylic acid precipitation [Antibodies, A Laboratory manual, Cold Spring Harbor Laboratory (1988)], or chromatography using a DEAE-Sepharose column, an anion exchange column, a protein A or G-column, a gel filtration column and the like may be employed alone or as a combination thereof.

(ii) Production of Monoclonal Antibody

A monoclonal antibody can be prepared by preparing a hybridoma through fusion of the antibody-producing cells with myeloma cells of a non-human mammal and culturing the hybridoma, or administering the hybridoma to an animal to induce ascites tumor in the animal, and then isolating and purifying it from the culture medium or ascitic fluid.

Examples of the antibody-producing cells include spleen cells, lymph nodes and antibody-producing cells in peripheral blood. Particularly, spleen cells are preferred.

A method for producing a monoclonal antibody using spleen cells is described below; however, other antibody-producing cells can also be carried out in the same manner.

The spleen is excised from rats showing an antibody titer 3 to 7 days after the final immunization.

The spleen is cut to pieces in MEM medium (manufactured by Nissui Pharmaceutical), loosened using a pair of forceps, followed by centrifugation at 1,200 rpm for 5 minutes, and the resulting supernatant is discarded.

The spleen in the precipitated fraction is treated with a Tris-ammonium chloride buffer (pH 7.65) for 1 to 2 minutes to eliminate erythrocytes and washed three times with MEM medium, and the resulting spleen cells were used as antibody-producing cells.

(b) Preparation of Myeloma Cells

As myeloma cells, an established cell line obtained from mouse or rat is used. Examples include cell lines derived from mouse, such as P3-X63Ag8-U1 (hereinafter referred to as "P3-U1") [*Current Topics in Microbiology and Immunology*, 81, 1 (1978), *European J. Immunology*, 6, 511 (1976)], SP2/O-Ag14 (SP-2) [*Nature*, 276, 269 (1978)], P3-X63-Ag8653 (653) [*J. Immunology*, 123, 1548 (1979)], P3-X63-Ag8 (X63) cell line [*Nature*, 256, 495 (1975)] and the like, which are 8-azaguanine-resistant mouse (BALB/c) myeloma cell lines. These cell lines were subcultured in 8-azaguanine medium [medium in which, to a medium obtained by adding glutamine (1.5 mM), 2-mercaptoethanol ($5 \times 10^{-5}$ M), gentamicin (10 $\mu$g/ml) and fetal calf serum (FCS) (manufactured by CSL, 10%) to RPMI-1640 medium (hereinafter referred to as the "normal medium"), 8-azaguanine has been further added] and cultured in the normal medium 3 or 4 days before cell fusion, and $2 \times 10^7$ or more of the cells are used for the fusion.

(c) Production of Hybridoma

The antibody-producing cells obtained in (a) and the myeloma cells obtained in (b) are washed with MEM medium or PBS (disodium hydrogen phosphate: 1.83 g, sodium dihydrogen phosphate: 0.21 g, sodium chloride: 7.65 g, distilled water: 1 liter, pH: 7.2) and mixed to give a ratio of antibody-producing cells:myeloma cells=5 to 10:1, followed by centrifugation at 1,200 rpm for 5 minutes, and the supernatant is discarded.

The cells in the resulting precipitated fraction were thoroughly loosened, 0.2 to 1 ml of a mix solution of 2 g polyethylene glycol-1000 (PEG-1000), 2 ml MEM medium and 0.7 ml dimethylsulfoxide (DMSO) per $10^8$ antibody-producing cells is added to the cells under stirring at 37° C., and then 1 to 2 ml of MEM medium is further added thereto several times at 1 to 2 minute intervals.

After the addition, MEM medium is added to give a total amount of 50 ml. The resulting prepared solution is centrifuged at 900 rpm for 5 minutes, and then the supernatant is discarded. The cells in the resulting precipitated fraction were gently loosened and then gently suspended in 100 ml of HAT medium [the normal medium to which hypoxanthine ($10^{-4}$ M), thymidine ($1.5 \times 10^{-5}$ M) and aminopterin ($4 \times 10^{-7}$ M) have been added] by repeated drawing up into and discharging from a measuring pipette.

The suspension is poured into a 96 well culture plate at 100 $\mu$L/well and cultured at 37° C. for 7 to 14 days in an atmosphere of 5% $CO_2$ in a 5% $CO_2$ incubator.

After culturing, a part of the culture supernatant is recovered, and a hybridoma which specifically reacts with a partial fragment protein of the protein of the present invention is selected according to the enzyme immunoassay described in *Antibodies, A Laboratory manual,* Cold Spring Harbor Laboratory, Chapter 14 (1998) and the like.

A specific example of the enzyme immunoassay is described below.

A 1 to 50 $\mu$g/ml portion of the antigen used in the immunization is poured into a 96 well plate for EIA at 10 to 100 $\mu$l/hole, and allowed to stand at 4° C. overnight for coating on the plate.

After allowing to stand, PBS solution containing 1% BSA (hereinafter referred to as "BSA-PBS") at 100 to 200 $\mu$l/hole and allowed to stand at room temperature for 1 to 2 hours or at 4° C. for one to two nights for blocking protein-binding residues which remain on the plate.

After blocking, BSA-PBS is discarded, and the plate is washed sufficiently with PBS.

The immunized animal serum, polyclonal antibody obtained by purifying from the antiserum, hybridoma culturing supernatant or purified antibody obtained in (d) described below is used as a first antibody, and 1 to 10 $\mu$g/ml of the antibody is poured to the plate at 20 to 100 $\mu$l/hole, and allowed to stand at room temperature for 2 to 3 hours or at 4° C. overnight.

After washing the plate sufficiently with PBS or PBS-0.05% Tween, 1 to 50 $\mu$g/ml of an anti-immunoglobulin antibody labeled with a biotin, a chemical luminous substance, a radiation substance or the like as a second antibody is poured at 50 to 100 $\mu$l/hole and allowed to react at room temperature for 1 to 2 hours.

After washing the plate sufficiently with PBS-Tween, a reaction is carried out according to the labeled substance of the second antibody.

A hybridoma which specifically reacts with the protein of the present invention in the reaction is selected as one capable of producing a monoclonal antibody of the present invention.

Cloning is repeated using the hybridoma twice by limiting dilution analysis [HT medium (a medium in which aminopterin has been removed from HAT medium) is firstly used, and the normal medium is secondly used], and a hybridoma which shows stable and an enough antibody titer is selected as a hybridoma capable of producing a monoclonal antibody of the present invention.

(d) Preparation of Monoclonal Antibody

The monoclonal antibody-producing hybridoma cells obtained in (c) are injected intraperitoneally into 8- to 10-week-old mice or nude mice treated with pristane [intraperitoneal administration of 0.5 ml of 2,6,10,14-tetramethylpentadecane (pristane), followed by 2 weeks of feeding] at 5 to $20 \times 10^6$ cells/animal. The hybridoma causes ascites tumor in 10 to 21 days.

The ascitic fluid is collected from the mice or nude mice, and centrifuged to remove solid contents.

A monoclonal antibody can be purified and isolated from the resulting supernatant according to the method similar to that used in the polyclonal antibody.

The subclass of the antibody can be determined using a mouse monoclonal antibody typing kit or a rat monoclonal antibody typing kit. The protein amount can be determined by the Lowry method or by calculation based on the absorbance at 280 nm.

4. Application of IgA Nephropathy-Related DNA, Protein or Antibody (1) Using the DNA described in the above section 1, mRNA of the IgA nephropathy-related gene of the present invention can be detected by northern hybridization (Molecular Cloning, 2nd ed.), PCR [*PCR Protocols*, Academic Press (1990)], RT (reverse-transcribed)-PCR and the like. Particularly, RT-PCR is simple and easy and can therefore be applied to the diagnosis of IgA nephropathy.

For example, diagnosis of IgA nephropathy may be effected by carrying out PCR using the DNA described in the above section 1 which corresponds to the mRNA to be detected as a pair of oligonucleotide primers and detecting the amplified fragment. In that case, the nucleotide sequence moiety to be amplified may be any nucleotide sequence region of the mRNA, but a nucleotide sequence region which has a length of from 50 bp to 2 kbp and does not contain a repeating sequence or GC (guanine-cytosine) bases-rich sequence is preferred.

(2) Using the antisense oligonucleotide (RNA/DNA) described in the above section 1 [*Chemistry*, 46, 681 (1991), *Biotechnology*, 9, 358 (1992)], treatment of IgA nephropathy can be effected by inhibiting transcription of DNA or translation of mRNA.

An example of the antisense oligonucleotide (RNA/DNA) of the above section 1 used in this case is an antisense oligonucleotide which has a partial nucleotide sequence, preferably a sequence of from 10 to 50 bases in the translation initiation region, of a DNA which encodes the protein described in the above section 2.

(3) Using the DNA described in the above section 1, the IgA nephropathy-related protein of the present invention can be obtained by the method described in the above section 2.

(4) Using the protein described in the above section 2 as the antigen, antibodies can be produced by the method described in the above section 3.

(5) Using the antibody described in the above section 3, the IgA nephropathy-related protein can be detected or determined immunologically.

Examples of the immunological detection method include ELISA method using a microtiter plate, fluorescent antibody technique, western blot technique, immunohistochemical staining and the like.

Examples of the immunological determination method include sandwich ELISA method in which, among antibodies which react with the protein of the present invention in solution, two monoclonal antibodies having different epitopes are used and radioimmunoassay method in which the protein of the present invention labeled with radioactive isotope, such as $^{125}$I or the like, and an antibody which recognizes the protein of the present invention are used.

(6) Using the antibody described in the above section 3, the presence or absence of IgA nephropathy in a person to be inspected can be diagnosed by immunologically detecting or determining an IgA nephropathy-related protein in leukocytes collected from a healthy person and the person to be inspected, comparing its amounts in the healthy person and person to be inspected and then examining the quantitative fluctuation. As a specific sample to be tested, leukocytes separated from peripheral blood samples of a healthy person and a person to be inspected can be used. Additionally, when the IgA nephropathy-related protein to be detected is a protein secreted from leukocytes, the presence or absence of IgA nephropathy in a person to be inspected can be detected and diagnosed by immunologically detecting or determining the protein in blood plasma samples collected from a healthy person and the person to be inspected, comparing its amounts in the healthy person and person to be inspected and then examining its quantitative fluctuation.

(7) The antibody described in the above section 3 can be applied to the treatment or prevention of IgA nephropathy.

When the DNA, protein and antibody of the present invention is used for the diagnosis, treatment or prevention of IgA nephropathy, a diagnostically or pharmacologically acceptable carrier may be added.

The diagnosis and treatment of IgA nephropathy can be effected using the DNA, protein and antibody of the present invention.

Examples of the present invention are given below by way of illustration and not by way of limitation.

EXAMPLE 1

Differential Display of Leukocytes of IgA Nephropathy Patients and Healthy Persons (1) Preparation of Total RNA from Leukocytes of IgA Nephropathy Patients and Healthy Persons A 20 ml portion of blood was collected from each of five IgA nephropathy patients and five healthy persons.

This was mixed with 500 µl of 1,000 units/ml heparin solution to inhibit coagulation, transferred into a centrifugation tube and then centrifuged at 3,300 rpm for 15 minutes at room temperature, and the resulting intermediate layer buffy coat containing leukocytes was transferred into another centrifugation tube.

Thereafter, total RNAs were obtained in accordance with the AGPC method [*Experimental Medicine*, 9, 1937 (1991)] or using an RNA recovering kit, RNAeasy (manufactured by QIAGEN).

(2) Fluorescence Differential Display Using Leukocyte Total RNAs of IgA Nephropathy Patients and Healthy Persons Distilled water was added to 2.5 µg of each of the total RNAs obtained in the above step (1) to a total volume of 9 µl, and the solution was mixed with 1 µl of an anchor primer (50 µM, custom-synthesized by Sawady Technology) whose 5'-end had been fluorescence-labeled with fluorescein isothiocyanate (referred to as "FITC" hereinafter), heated at 70° C. for 5 minutes and then immediately cooled on an ice bath.

Since each of the three primers FAH (nucleotide sequence is shown in SEQ ID NO:107), FGH (nucleotide sequence is shown in SEQ ID NO:108) and FCH (nucleotide sequence is shown in SEQ ID NO:109) was used in each reaction as the 5'-end fluorescence-labeled anchor primer, a total of three combinations of reactions were carried out for one sample of total RNAs.

A 4 µl portion of 5× reverse transcriptase reaction buffer [250 mM tris(hydroxymethyl)aminomethane (Tris)-HCl (pH 8.3), 375 mM KCl, 15 mM MgCl$_2$] was mixed with 2 µl of 100 mM dithiothreitol (DTT), 1 µl of 10 mM DNTP (DATP, dGTP, dTTP and dCTP), 1 µl of distilled water and 1 µl (200 units) of a reverse transcriptase SUPERSCRIPT II RNase H-Reverse Transcriptase (manufactured by Life Technologies), and the resulting mixture was allowed to stand at room temperature for 10 minutes, allowed to react at 42° C. for 50 minutes to synthesize a cDNA, and then heated at 90° C. for 5 minutes to terminate the reaction.

After the reaction, to the reaction solution was added 40 µl of TE buffer [10 mM Tris-HCl (pH 8.0), 1 mM disodium ethylenediaminetetraacetate (EDTA) (pH 8.0)].

Next, 14.7 µl of distilled water, 2 µl of 10×PCR buffer [100 mM Tris-HCl (pH 8.8), 500 mM KCl, 15 mM MgCl$_2$, 1% Triton X-100], 0.8 µl of 2.5 mM DNTP, 0.3 µl of 50 µM fluorescence-labeled anchor primer (the same among FAH, FGH and FCH used in the cDNA synthesis), 1 µl of 10 µM arbitrary primer (manufactured by Operon) and 0.2 µl of Gene Taq DNA polymerase (5 units/µl, manufactured by Nippon Gene) were added to 1 µl of each of the thus synthesized cDNA samples, and the resulting mixture was arranged in Thermal Cycler to carry out PCR.

The PCR was effected by carrying out the reaction at 94° C. for 3 minutes, 40° C. for 5 minutes and 72° C. for 5 minutes, subsequently carrying out a total of 27 cycles of the reaction in which one cycle was composed of the steps of 95° C. for 15 seconds, 40° C. for 2 minutes and 72° C. for 1 minute, and finally carrying out 5 minutes of the reaction at 72° C.

Since each reaction was carried out by a combination of one of the above-described three types as the fluorescence-labeled anchor primer with one of 60 types of OPD-1 to 20, OPE-1 to 20 and OPV-1 to 20 manufactured by Operon Technologies as the arbitrary primer, a total of 180 reactions, and since a reaction of the fluorescence-labeled anchor primer FGH with an arbitrary primer OPB-2 (manufactured by Operon Technologies) was also carried out, a total of 181 reactions were carried out for each of the total RNAs.

A 4 µl portion of each of the PCR reaction solutions was mixed with 3 µl of electrophoresis sample buffer use (95% formamide, 0.1% xylene cyanol, 0.1% Bromophenol Blue), and the mixture was heated at 95° C. for 2 minutes, immediately cooled thereafter on an ice bath and then subjected to 2.5 hours of 6% acrylamide gel electrophoresis at 1,500 V. A solution composed of 89 mM Tris, 89 mM boric acid and 2 mM EDTA was used as the electrophoresis buffer. By measuring fluorescence of the gel after electrophoresis using Fluor Imager (manufactured by Molecular Dynamics), the fragments amplified by PCR were detected and compared. In comparison with 5 cases of the healthy persons, a band which significantly increased or decreased in leukocytes of 5 cases of the IgA nephropathy patients was recorded.

Total RNAs were prepared from other 3 cases of IgA nephropathy patients and 3 cases of healthy persons in the same manner as described in the above step (1) to carry out the differential display of the step (2).

A total of 197 bands which showed increased or decreased fluorescence in both of the above two trials of the differential display were cut off from the gels.

38 µl of distilled water, 5 µl of 10×PCR buffer, 4 µl of 2.5 mM DNTP, 0.6 µl of an anchor primer (no fluorescence labeling: 34 µM, custom-synthesized by Sawady Technology), 2 µl of 10 µM arbitrary primer and 0.5 µl of Gene Taq DNA polymerase were added to about ¼ portion of each of the gels thus cut off, the resulting mixture was heated at 94° C. for 3 minutes and then a total of 30 cycles of the reaction was carried out in which one cycle was comprised of the steps of 95° C. for 15 seconds, 40° C. for 2 minutes and 72° C. for 1 minute, subsequently carrying out 5 minutes of the reaction at 72° C. to complete PCR.

Each of the resulting reaction solutions was extracted with phenol-chloroform (1:1) and then with chloroform-isoamyl alcohol (24:1), subsequently carrying out ethanol precipitation.

The thus obtained precipitate (amplified DNA fragments) was dissolved in TE buffer and subjected to 1.5% low melting point agarose gel (SEA PLAQUE GTG, manufactured by FMC Bioproducts) electrophoresis.

After the electrophoresis, the resulting gels were stained with ethidium bromide and then the bands containing amplified fragments were cut off.

The gel was heated at 65° C. for 15 minutes to melt agarose and then extracted with phenol-chloroform and then with chloroform-isoamyl alcohol.

The thus obtained extract was subjected to ethanol precipitation and the resulting precipitate (amplified fragments) was dissolved in 10 µl of TE buffer.

A 1 µl portion of each of the amplified fragments was mixed with 1 µl of a vector for PCR fragment cloning use, pT7BlueT-Vector (manufactured by Novagen), and the amplified fragment was cloned into the plasmid using DNA Ligation Kit ver.1 (manufactured by Takara Shuzo) in accordance with the manual attached to the kit.

Using the thus obtained recombinant plasmid, *Escherichia coli* DH5α (manufactured by Gibco BRL) was transformed in accordance with a known method, and the resulting transformant was spread on LB agar medium containing 50 µg/ml of ampicillin and cultured overnight at 37° C.

The thus grown ampicillin-resistant transformant was suspended in 20 µl of distilled water, the suspension was mixed with 2.5 µl of 10×PCR buffer, 2 µl of 2.5 mM dNTP, 0.3 µl of 34 µM anchor primer, 1 µl of 10 µM arbitrary primer and 0.5 µl of a Gene Taq DNA polymerase, and the mixture was subjected to PCR under the same conditions of the above-described re-amplification of amplified fragments and then analyzed by electrophoresis which recognized that an amplified fragment has the same length as in the first differential display.

Nucleotide sequence of the amplified fragment was determined using DNA Sequencer (manufactured by Perkin Elmer). In carrying out the nucleotide sequence determination, Dye Primer Cycle Sequencing Kit manufactured by Perkin Elmer and the method described in the manual attached to the kit were used.

Using restriction enzymes capable of cleaving restriction enzyme sites in the determined nucleotide sequence, the reaction product obtained by the above-described differential display was cleaved and then subjected to electrophoresis to recognize that the position of electrophoresis band corresponding to the thus cut off amplified fragment was changed.

Each of the thus obtained nucleotide sequences was compared with a nucleotide sequence data base GenBank to select a total of 66 clones which were not present among the known nucleotide sequences in the data base or coincided only with the expressed sequence tag among nucleotide sequences in the data base.

EXAMPLE 2

Detection of Specificity of mRNA Expression by RT-PCR

Using 2 µg of each of the total RNAs obtained in Example 1 from leukocytes of five cases of IgA nephropathy patients and 5 cases of healthy persons, a single-stranded cDNA was synthesized using a single-stranded cDNA synthesis kit, Superscript Preamplification System (manufactured by Life Technologies) in accordance with the method described in the manual attached to the kit.

A 21 µl portion of the thus obtained solution containing the single-stranded cDNA was adjusted to a total volume of 420 µl by adding distilled water.

Using 10 µl portion of the thus prepared solution, the expression level of mRNA corresponding to each amplified fragment was detected by carrying out RT-PCR in the following manner.

That is, 10 µl of the leukocyte single-stranded cDNA solution was mixed with 15.8 µl of distilled water, 4 µl of 10×PCR buffer, 3.2 µl of 2.5 mM dNTP, 2 µl of DMSO, 2 µl of 10 µM gene-specific 5'-end side sense primer, 2 µl of 10 µM gene-specific 3' side antisense primer and 2 µl of Gene Taq DNA polymerase which had been diluted to 1 unit/µl, and the resulting mixture was heated at 97° C. for 5 minutes, cooled on an ice bath for 5 minutes and then a total of 28 cycles of PCR was carried out in which one cycle was comprised of the steps of 94° C. for 30 seconds, 65° C. for 1 minute and 72° C. for 2 minutes.

After completion of the PCR, 2% agarose gel electrophoresis was carried out, the resulting gel was stained with 0.01% Cyber Green (manufactured by Takara Shuzo), and the amount of the thus stained amplified fragment was determined by Fluor Imager and used as relative expression quantity of mRNA.

In order to make a correction of the amount of mRNA, the same reaction was carried out on a house keeping gene, glyceraldehyde 3-phosphate dehydrogenase (G3PDH) gene, using specific primers (SEQ ID NO:112 and NO:113) and the expression level of mRNA for each gene was corrected based on the ratio of the expression level of G3PDH mRNA, and then the average value of five cases of IgA nephropathy patients and the average value of 5 cases of healthy persons were compared and 30 gene clones having a difference in their values were selected as genes whose expression quantity was changed in patients with IgA nephropathy. The thus selected genes are summarized in Tables 1—1 and 1-2.

TABLE 1-1

| No | Gene | Amplification primer[1] | bp[2] | Expression fluctuation[3] | RT-PCR primer[4] | SEQ ID NO.[5] | RT-PCR cycle number |
|---|---|---|---|---|---|---|---|
| 1 | INM063-7 | FGH/OPB-2 | 155 | 12.5 | 45, 46 | 8 | 28 |
| 2 | INP303A | FAH/OPD-5 | 305 | 9.9 | 47, 48 | 41 | 28 |
| 3 | INM315-10 | FAH/OPD-9 | 278 | 2.8 | 49, 50 | 9 | 35 |
| 4 | INP319-3 | FAH/OPD-10 | 135 | 14.4 | 51, 52 | 10 | 28 |
| 5 | INP324A | FAH/OPD-12 | 197 | 19.9 | 53, 54 | 11 | 28 |
| 6 | INP332A | FAH/OPD-16 | 137 | 16.6 | 55, 56 | 12 | 28 |
| 7 | INM335-3 | FAH/OPD-17 | 274 | 4.2 | 57, 58 | 13 | 28 |
| 8 | INM336A | FAH/OPD-17 | 171 | 0.14 | 59, 60 | 14 | 28 |
| 9 | INM351-10 | FCH/OPD-4 | 161 | 1.8 | 61, 62 | 15 | 28 |
| 10 | INP356-4 | FCH/OPD-7 | 323 | 18.5 | 63, 64 | 16 | 35 |
| 11 | INP364A | FCH/OPD-12 | 138 | 3.8 | 65, 66 | 17 | 28 |
| 12 | INP377A | FGH/OPD-1 | 256 | 5.0 | 67, 68 | 42 | 28 |
| 13 | INP379A | FGH/OPD-2 | 244 | 8.6 | 69, 70 | 43 | 35 |
| 14 | INP380A | FGH/OPD-2 | 135 | 15.7 | 71, 72 | 18 | 35 |
| 15 | INP401A | FGH/OPD-20 | 258 | 16.7 | 73, 74 | 44 | 24 |
| 16 | INM403A | FAH/OPE-3 | 219 | 2.3 | 75, 76 | 19 | 28 |
| 17 | INP407A | FAH/OPE-5 | 191 | 9.1 | 77, 78 | 20 | 28 |
| 18 | INM408A | FAH/OPE-5 | 148 | 0.65 | 79, 80 | 21 | 28 |
| 19 | INP410-5 | FAH/OPE-6 | 306 | 2.0 | 81, 82 | 22 | 28 |
| 20 | INM419-14 | FAH/OPE-11 | 357 | 0.064 | 83, 84 | 23 | 35 |

TABLE 1-2

| No | Gene | Amplification primer[1] | bp[2] | Expression fluctuation[3] | RT-PCR primer[4] | SEQ ID NO.[5] | RT-PCR cycles number |
|---|---|---|---|---|---|---|---|
| 21 | INP429A | FGH/OPE-7 | 219 | 2.4 | 85, 86 | 24 | 28 |
| 22 | INP431A | FGM/OPE-8 | 251 | 13.1 | 87, 88 | 25 | 24 |
| 23 | INP438A | FGH/OPE-11 | 233 | 5.4 | 89, 90 | 26 | 24 |
| 24 | INP444A | FGH/OPE-15 | 176 | 3.3 | 91, 92 | 27 | 24 |
| 25 | INP451-2 | FCH/OPE-4 | 241 | 14.0 | 93, 94 | 28 | 32 |
| 26 | INP458A | FCH/OPE-11 | 217 | 9.2 | 95, 96 | 29 | 28 |
| 27 | INP463A | FCH/OPE-19 | 233 | 18.2 | 97, 98 | 30 | 35 |
| 28 | INP470A | FCH/OPV-4 | 228 | 5.8 | 99, 100 | 31 | 28 |
| 29 | INP482A | FCH/OPV-10 | 298 | 9.9 | 101, 102 | 32 | 28 |
| 30 | INP485-6 | FCH/OPV-17 | 291 | 8.5 | 103, 104 | 33 | 28 |

[1] A combination of the anchor primer with the arbitrary primer used in the differential display is shown.
[2] The length of the amplified fragment of the differential display is shown.
[3] Expression fluctuation is shown as the value of "the average value of mRNA expression levels in 5 cases of IgA nephropathy patients/the average value of mRNA expression levels in 5 cases of healthy persons".
[4] The primer used in the RT-PCR is shown by the SEQ ID NO.
[5] SEQ ID NO. of the Sequence Listing corresponding to the nucleotide sequence of amplified fragment obtained by the differential display described in Example 1 is shown.

Thus, it becomes possible to carry out diagnosis of nephropathy by observing the expression levels of these genes in the leukocytes samples to be tested by PT-PCR using primers of these genes and mRNAs of the samples.

EXAMPLE 3

Cloning of Full Length cDNA and Analysis of Each cDNA Clone (1) Cloning of Full Length cDNA Cloning of a cDNA containing the nucleotide sequence of amplified fragment obtained by differential display was carried out by optionally using a gene trapper method, plaque hybridization of a cDNA library and a 5"-RACE method. The methods are described below.

(A) Gene Trapper Method

A cDNA clone was obtained from a human leukocyte cDNA library (manufactured by Life Technologies) by the following method in which pCMV-SPORT (manufactured by Life Technologies) was used as the vector, using GENE TRAPPER cDNA Positive Selection System (manufactured by Life Technologies).

That is, clones in the cDNA library were made into single-stranded DNA (correspond to the antisense strand of cDNA) using Gene II protein and exonuclease III, and hybridization was carried out using a probe, namely a biotinated oligonucleotide specific for each gene (the 5'-end sense primer specific to each gene, used in the RT-PCR in Example 2, was used).

By allowing the biotinated probe to bind to magnetic beads to which streptoavidin had been immobilized, the above-described single-stranded cDNA hybridized with the probe was isolated.

The single-stranded cDNA clone was released from the probe, made into double-stranded DNA using a DNA polymerase and then *Escherichia coli* was transformed with the double-stranded DNA to obtain a transformant containing the cDNA clone.

Illustrative method employed was as described in the manual attached to the kit.

Each of the thus obtained transformants was suspended in 18 μl of distilled water, the suspension was mixed with 2.5 μl of 10×PCR buffer, 2 μl of 2.5 mM dNTP, 1 μl of 10 μM gene-specific 5' side sense primer, 1 µl of 10 µM gene-specific 3' side antisense primer and 0.5 µl of Gene Taq DNA polymerase, and the resulting mixture was subjected to PCR under the same conditions as the RT-PCR, subsequently carrying out electrophoresis to isolate a transformant as the cDNA clone of interest in which a fragment having a length deduced from the positions of primers was amplified.

(B) Screening of cDNA Library

Screening of cDNA clones was carried out by means of plaque hybridization using a cDNA library of leukocytes of patient with IgA nephropathy and a cDNA library of a neuroblastoma cell line NB-1.

Prior to the plaque hybridization of each library, PCR was carried out in the same manner as in Example 2, using each cDNA library as the template and using each of the gene-specific RT-PCR primers used in Example 2, and a library, in which a fragment having a length deduced from the position of the primer was amplified, was selected as the library that contains the cDNA clone of the gene of interest.

Using the library, DNAs in plaques were blotted on a nylon membrane Hybond N+ (manufactured by Amersham).

Using a plasmid which contained the amplified fragment of each gene and was obtained by the differential display of Example 1, as the template, and each of the gene-specific primers used for the RT-PCR in Example 2 as a primer, PCR was carried out by adding PCR DIG labeling mix (manufactured by Boehringer Mannheim) to the reaction solution, thereby amplifying and labeling each gene-specific fragment.

Using each of the thus amplified and labeled gene-specific fragments as a probe, hybridization and detection of positive plaques were carried out in accordance with the manual provided by Boehringer Mannheim.

DIG Nucleic Acid Detection Kit (manufactured by Boehringer Mannheim) was used for the detection.

(B-1) Preparation of IgA Nephropathy Patient Leukocyte cDNA Library

A 50 ml portion of blood sample was collected from each of four patients with IgA nephropathy, and each of the blood samples was centrifuged using Polymorphprep to isolate respective leukocyte fractions. The specific method was described in the manual attached to the Polymorphprep.

Using the thus isolated leukocytes, total RNAs were prepared by employing the guanidine thiocyanate-cesium trifluoroacetate method [*Methods in Enzymology*, 154, 3 (1987)]. From a total of 200 ml of blood samples, 320.7 µg of total RNAs was obtained.

A 272.6 µg portion of the thus obtained total RNAs was passed through an oligo(dT) cellulose column to obtain 10.7 µg of mRNA as poly (A)+ RNA.

In the same manner, 6.9 µg of mRNA was obtained from other four patients of IgA nephropathy.

Using 10.0 µg and 6.4 µg of the thus obtained respective mRNA samples, synthesis of cDNA, addition of EcoRI adapter and digestion reaction with XhoI were carried out using uniZAP-cDNA Synthesis Kit (manufactured by Stratagene), and the resulting fragments were inserted between EcoRI/XhoI of λ Zap II by ligation to prepare a cDNA library in which the cDNA was inserted in such a direction that its 5'-end was always present in the EcoRI site side of the vector.

The above specific method was described in the manual provided by Stratagene.

After packaging using a λ phage packaging kit Gigapack III Gold packaging extract (manufactured by Stratagene), *Escherichia coli* XL1-Blue MRF' was infected with the obtained library. The thus obtained cDNA library was used as the final cDNA library. The packaging and infection were carried out in accordance with the manual provided by Stratagene.

(B-2) Preparation of Neuroblastoma Cell Line NB-1 cDNA

Using RPMI 1640 medium (manufactured by Nissui Pharmaceutical) containing 10% fetal calf serum (manufactured by Biotech International), 2% penicillin (5,000 units/ml) streptomycin (5 mg/ml) solution (manufactured by Life Technology), 0.19% $NaHCO_3$ (manufactured by Sigma) and 4 mM glutamine, culturing and subculturing of a neuroblastoma cell line NB-1 (*The Autonomic Nervous System*, 10, 115 (1973), available from Human Science Research Resource Bank as JCRB0621) were carried out at 37° C. in an atmosphere of 5% $CO_2$, and $1.25\times10^8$ of confluent cells were recovered.

After washing of the thus recovered cells with PBS, 10.2 µg of purified mRNA was obtained using Fast Track mRNA Isolation Kit (manufactured by Invitrogen).

A 6 µg portion of the thus obtained mRNA and 1.5 µg of NotI-primer-adapter (manufactured by Promega) were put into a container, adjusted to 7 µl by adding distilled water, heated at 70° C. for 10 minutes and then rapidly cooled on an ice bath.

The thus rapidly cooled solution was mixed with 4 µl of 5× reverse transcriptase reaction buffer (attached to the enzyme), 2 µl of 100 mM DTT, 1 µl of 10 mM DNTP and 1 µl of [α-$^{32}$P] dCTP (110 TBq/mmol; manufactured by Amersham) as a tracer, and the mixture was incubated at 37° C. for 2 minutes, mixed with 5 µl of (1,000 units) of a reverse transcriptase, SUPERSCRIPT II RNase H− Reverse Transcriptase, and then allowed to react at 44° C. for 1 hour to synthesize a cDNA.

The thus obtained reaction solution was mixed with 82 µl of distilled water, 32 µl of 5× reaction buffer [100 mM Tris-HCl, 500 mM KCl, 25 mM $MgCl_2$, 50 mM $(NH_4)_2SO_4$, 10 mM DTT, 250 mg/ml bovine serum albumin (BSA), 750 mM β-nicotinamide dinucleotide], 2.75 µl of 10 mM dNTP, 2.75 µl of [α-$^{32}$P] dCTP, 5.5 µl of 100 mM DTT, 2.5 µl of 6 units/µl *E. coli* DNA ligase (manufactured by Takara Shuzo), 11.5 µl of 3.5 units/µl *E. coli* DNA polymerase (manufactured by Takara Shuzo) and 2 µl of 0.6 unit/µl of *E. coli* ribonuclease H (manufactured by Takara Shuzo), and the thus prepared mixture was allowed to react at 16° C. for 3 hours to decompose the mRNA and obtain a double-stranded cDNA.

The reaction solution was mixed with 4.8 µl of 1 unit/µl T4 DNA polymerase (manufactured by Takara Shuzo) and subjected to 5 minutes of the reaction at 16° C. to form blunt ends at both termini.

The reaction solution was mixed with 2 µl of 500 mM EDTA (pH 8.0) and 2 µl of 10% sodium dodecyl sulfate (SDS) to terminate the reaction and then extracted with phenol-chloroform to denature and remove the enzyme. An aqueous layer was obtained.

In order to remove the cDNA of 400 bp or less in length and unreacted NotI-primer-adapter and nucleotide, the thus obtained aqueous layer was put on SizeSep-400 span column (manufactured by Pharmacia) which had been equilibrated with TE buffer and centrifuged at 400 g for 2 minutes, and the resulting eluate was subjected to ethanol precipitation to recover the cDNA.

The thus recovered cDNA was dissolved by adding 5 µl (50 pmol) of EcoRI adapter (manufactured by Promega) and mixed with 40 µl of the (A) solution and then with 5 µl of the (B) solution of Ligation Kit Ver.1 (manufactured by Takara Shuzo), and the resulting mixture was allowed at 15° C. for 2 hours to effect addition of the EcoRI adapter to both termini of the cDNA.

The reaction solution was mixed with 40 µl of 10 mM EDTA (pH 8.0) and heated at 65° C. for 15 minutes to terminate the reaction, and then the cDNA was recovered by ethanol precipitation.

The thus recovered cDNA was dissolved in 36 µl of distilled water and mixed with 5 µl of 10× reaction buffer [500 mM Tris-HCl (pH 7.6), 100 mM $MgCl_2$], 2.5 µl of 100 mM DTT, 2.5 µl of 10 mM ATP and 4 µl of 6 units/µl T4 polynucleotide kinase (manufactured by Takara Shuzo), and the mixture was allowed to react at 37° C. to for 30 minutes to phosphorylate the 5'-end of the added EcoRI adapter.

The reaction solution was mixed with 7.2 µl of distilled water, 1.8 µl of 5 M NaCl and 8 units (1 µl) of NotI, and the mixture was subjected to 2 hours of the reaction at 37° C. to cut off the NotI site in the NotI-primer-adapter.

After adding 6 µl of 500 mM EDTA to terminate the reaction, the reaction solution was mixed with 1 µl of 20 µg/µl tRNA and then extracted with phenol-chloroform to denature and remove the enzyme. An aqueous layer was obtained.

In order to remove unreacted EcoRI adapter, the thus obtained aqueous layer was put on SizeSep-400 span column which had been equilibrated with TE buffer and centrifuged at 400 g for 2 minutes to recover the eluate.

The thus recovered eluate was overlaid on potassium acetate solution having a concentration gradient of from 5 to 20%, ultracentrifuged at 50,000 rpm for 3 hours. Then, 21 fractions were recovered from the bottom of the centrifugation tube using a peristaltic pump.

Each of the fractions was subjected to ethanol precipitation to recover cDNA, a portion of each of the thus recovered samples was subjected to agarose gel electrophoresis and then to autoradiography to measure the length of cDNA contained in each fraction, and the samples were recovered in three fractions, namely a fraction (H) containing cDNA of about 3 kb or more, a fraction (M) containing cDNA of 1 to 3 kb and a fraction (L) containing cDNA of 1 kb or less.

A 9 µg (9 µl) portion of a cloning vector ZAP II (manufactured by Stratagene) was mixed with 10 µl of 10×H restriction enzyme buffer (manufactured by Takara Shuzo), 75 µl of distilled water and 90 units (6 µl) of EcoRI, and the mixture was subjected to 2 hours of the reaction at 37° C.

The reaction solution was mixed with 1 µl of 5 M NaCl and 40 units (5 µl) of NotI, allowed to react at 37° C. for 2 hours, and further mixed with 8 units (1 µl) of NotI and again subjected to 1 hour of the reaction at 37° C. to cleave the EcoRI site and NotI site of the vector.

The reaction solution was mixed with 100 µl of 2 M Tris-HCl (pH 8.0) and 1 unit (2 µl) of E. coli C75 alkaline phosphatase (manufactured by Takara Shuzo) and allowed to react at 60° C. for 30 minutes to dephosphorylate the 5'-ends of the vector cleaved by EcoRI and NotI, and then these enzymes were removed by repeating phenol-chloroform extraction twice.

After removal of the enzymes, chloroform extraction was carried out and the resulting water layer was subjected to ethanol precipitation to recover the vector DNA which was subsequently dissolved in TE buffer.

Each of the cDNA samples recovered in three fractions was mixed with 1 µg of the vector DNA and subjected to ethanol precipitation, and the thus recovered vector DNA and cDNA were dissolved in 4 µl of a ligase buffer [100 mM Tris-HCl (pH 7.6), 5 mM $MgCl_2$, 300 mM NaCl], mixed with 4 µl of the (B) solution of Ligation Kit Ver. 1 and then allowed to react at 26° C. for 10 minutes to ligate the cDNA to the vector DNA.

A 4 µl portion of each of the reaction solutions was subjected to packaging using a λ phage packaging kit, Giga-Pack Gold II (manufactured by Stratagene). The reagents and methods were described in the manual attached to the kit.

E. coli XL1-Blue MRF' was infected with the thus obtained phage and the titer was measured. Thereafter, the cDNA library was amplified once by growing the phage on a plate medium and recovering it in SM buffer and used as the final cDNA library. The measurement of titer and amplification of library were carried out in accordance with the manual attached to the λ phage packaging kit. A library prepared from the (H) fraction containing cDNA of about 3 kb or more was used for the screening of the present invention.

(C) 5'-RACE

5'-RACE of the IgA nephropathy patient cDNA prepared in the above method (B) was carried out using 5'-RACE System ver. 2 (manufactured by Life Technologies). The specific method was described in the manual attached to the kit.

Using the above methods (A) to (C), cDNA cloning of the seven genes shown in Table 2 was achieved.

TABLE 2

| Gene name | SEQ ID NO. | cDNA clone | Method[1] | cDNA source |
|---|---|---|---|---|
| INP303A | 1 | GTINP303A-41a | A | human leukocytes |
|  |  | INP303A phi-3 | B | NB-1 |
|  |  | INP303A-R1 | C | IgA nephropathy leukocytes |
| INP377A | 2 | GTINP377A-46C | A | human leukocytes |
| INF379A | 3 | PHINP379A-16-2 | B | IgA nephropathy leukocytes |
| INP401A | 4 | PHINP401A-8-1 | B | IgA nephropathy leukocytes |
|  | 5 | PHINP401A-14-1 | B | IgA nephropathy leukocytes |
| GTINP-332A-21 | 6 | GTINP332A-21 | A | human leukocytes |
|  |  | PHDTINP332A-21-28-1 | B | IgA nephropathy leukocytes |
| INM063-7 | 7 | INM063-7 ph5-1 INM063-7 ph4-1 INM063-7 ph9-1 | B | NB-1 |

[1]Cloning method of each cDNA clone obtained:
A: gene trapper method,
B: plaque hybridization of cDNA library
C: 5'-RACE method.

Nucleotide sequence of the cDNA moiety of each of the thus obtained cDNA clones was determined using 377 DNA Sequencer manufactured by Perkin Elmer. Determination of the nucleotide sequence was carried out using Dye cycle sequencing FS Ready Reaction Kit in accordance with the manual attached to the kit. Additionally, the nucleotide sequence was translated into amino acid sequence by three frames to examine whether an open reading frame (ORF) composed of 100 or more amino acids is present.

(1) INP303A

A cDNA clone GTINP303A-41a was obtained by the gene trapper method, but this was considered to be an incomplete cDNA clone because of the absence of ORF, which corresponds to 100 or more amino acids, in the nucleotide sequence of the cDNA.

In order to obtain a full length cDNA clone, 5'-RACE was carried out using specific primers (nucleotide sequences are shown in SEQ ID NO:110 and NO:111) which correspond to a moiety close to the 5'-end of GTINP303A-41a to obtain cDNA clone INP303A-R1. Also, since a part of the cDNA nucleotide sequence of GTINP303A-41a was not able to determine, another cDNA clone INP303A-ph1-3 was obtained from an NB-1 cDNA library by plaque hybridization.

By combining nucleotide sequences of these cDNA clones thus obtained, a 4,276 bp nucleotide sequence of the cDNA of INP303A was determined as shown in SEQ ID NO:1.

The nucleotide sequence of a fragment obtained by differential display (SEQ ID NO:41) coincided with the complementary chain nucleotide sequence corresponding to the positions 2,797 to 3,101 of SEQ ID NO:1. Therefore, it was considered that the anchor primer was not annealed to the 3'-end poly(A) sequence of mRNA but to the complementary strand of the sequence wherein continuous T's were present at the 2782nd to 2795th positions in SEQ ID NO:1.

An ORF corresponding to 239 amino acids (corresponds to the positions 53 to 742 of SEQ ID NO:1, the amino acid sequence is shown in SEQ ID NO:34) was found in the nucleotide sequence of the cDNA of INP303A-R1.

When the amino acid sequence of the ORF was compared with an amino acid data base, it was found that this sequence has a homology with C40H1 which was estimated to be a protein encoded by a Nematoda genomic gene clone C40H1, mouse cytoplasmic polyadenylation element binding protein (CPEBP) and *Drosophila* orb gene.

It was found also that an amino acid sequence just downstream of the region where these proteins showed a homology with the INP303A protein also showed a homology with the amino acid sequence encoded by the nucleotide sequence of positions 3,346 to 3,577 of SEQ ID NO:1. Therefore, it was assumed that this cDNA is a result of abnormal splicing in which a 2,689 bp nucleotide sequence (corresponds to positions 713 to 3,352 in SEQ ID NO:1) which seems to be an intron originally remained in the nucleotide sequence of INP303A.

It was found that the nucleotide sequence of a fragment which was obtained by the differential display and whose expression quantity increased in IgA nephropathy patients is present in this insertion sequence and the amount of mRNA which caused such an abnormal splicing increases in IgA nephropathy patients. It is highly possible that a protein translated from an mRNA which caused the abnormal splicing does not exert its original function, because its amino acid sequence at and after the 220 position is different from the original protein encoded by INP303A, namely a protein (295 amino acids) encoded by a nucleotide sequence resulting from the elimination of intron deduced from the a homology.

(2) INP377A

Nucleotide sequence of the cDNA of cDNA clone, GTINP377A-46C isolated by the gene trapper method was determined, with the thus obtained nucleotide sequence shown in SEQ ID NO:2.

When the nucleotide sequence of INP377A cDNA was compared with a nucleotide sequence data base, it was found that a sequence of the positions 1 to 552 of a human gene LUCA15 (GenBank accession No. U23946) which has a homology with a *Drosophila* cancer inhibition gene Sx1 coincides with the 50 to 527 position nucleotide sequence and 1,010 to 1,083 position nucleotide sequence of GTINP377A-46C. Consequently, it was assumed that GTINP377A-46C is a cDNA clone in which an intron of LUCA15 remained by an abnormal splicing.

A nucleotide sequence (SEQ ID NO:44) of a fragment obtained by the differential display method coincided with the nucleotide sequence of a complementary chain corresponding to the positions 759 to 1,014 of SEQ ID NO:2. Accordingly, it was considered that the anchor primer was not annealed to the 3'-end poly (A) sequence of mRNA but to the complementary strand of the sequence wherein continuous T's were present at the 745th to 757th positions in SEQ ID NO:2. Since the nucleotide sequence of the fragment is considered to be present in the nucleotide sequence which seems to be an intron of LUCA15, it is probable that the amount of mRNA which caused such an abnormal splicing increases in IgA nephropathy patients.

It is highly possible that the protein of 143 amino acids (the amino acid sequence is shown in SEQ ID NO:35) which is encoded by GTINP377A-46C does not exert its original function, because its amino acid sequence at and after the 137 position is different from the original protein (815 amino acids) encoded by LUCA15 cDNA.

(3) INP379A

A cDNA clone of INP379A, namely PHINP379A-16-2, was obtained by plaque hybridization of a cDNA library prepared from leukocytes of IgA nephropathy patients.

When the nucleotide sequence of the cDNA was determined, the XhoI site and poly T sequence were present in a side which was thought to be the 5'-end, so that it was considered that this is a clone in which cDNA was inserted into the vector in the opposite direction.

Consequently, a nucleotide sequence complementary to the thus obtained nucleotide sequence, which is the original nucleotide sequence of the cDNA, is shown in SEQ ID NO:3.

The nucleotide sequence of a fragment obtained by differential display (SEQ ID NO:43) coincided with the nucleotide sequence of the positions 2,706 to 2,949 of SEQ ID NO:3. An ORF corresponding to 104 amino acids (the amino acid sequence is shown in SEQ ID NO:36) was present in this nucleotide sequence.

Since no sequences having a homology with this amino acid sequence were found in the amino acid sequence data base, this cDNA was considered to be a gene which encodes a novel protein.

(4) INP401A

Two cDNA clones of INP401A, namely PHINP401A-8-1 and PHINP401A-14-1, were obtained by plaque hybridization of a cDNA library prepared from leukocytes of IgA nephropathy patients.

When nucleotide sequences of both cDNAs were determined, it was found that both sequences contained the same ORF corresponding to 133 amino acids, except for only one different base and therefore only one corresponding amino acid. Also, since both sequences were different from each other with regard to their nucleotide sequences of 5'-side non-translation region and 3'-side non-translation region, the presence of mRNAs having different polymorphism and splicing of the gene was assumed.

The nucleotide sequence of PHINP401A-8-1 is shown in SEQ ID NO:4, the nucleotide sequence of PHINP401A-14-1 in SEQ ID NO:5, the amino acid sequence of the protein encoded by PHINP401A-8-1 is shown in SEQ ID NO:37, and the amino acid sequence of the protein encoded by PHINP401A-14-1 in SEQ ID NO:38.

The nucleotide sequence of a fragment obtained by differential display (SEQ ID NO:42) coincided with the complementary chain nucleotide sequence corresponding to the positions 960 to 1,217 of SEQ ID NO:4 and the complementary chain nucleotide sequence corresponding to the positions 1,313 to 1,570 of SEQ ID NO:5. Accordingly, it was considered that the anchor primer was not annealed to the 3'-end poly(A) sequence of mRNA but to the complementary strand of the sequence wherein continuous T's were present at the 947th to 959th positions in SEQ ID NO:4 or the 1302nd to 1312th positions in SEQ ID NO:5.

The nucleotide sequence of a fragment which was obtained by the differential display and whose expression quantity increased in IgA nephropathy patients was found to have a nucleotide sequence complementary to the nucleotide sequences of PHINP401A-8-1 and PHINP401A-14-1.

The homology of the proteins encoded by PHINP401A-8-1 and PHINP401A-14-1 was examined, but no sequences having a homology were found in the amino acid sequence data base. Accordingly, they were considered to encode novel proteins.

An analysis of hydrophilic property deduced from the amino acid sequence showed a possibility that the protein encoded by INP401A is a secretory protein, and, in that case, the 1 to 15 position amino acid sequence of SEQ ID NO:37 or NO:38 was assumed to the signal peptide.

(5) GTINP322A-21

An attempt was made to obtain a cDNA clone of INP332A by the gene trapper method; however, nucleotide sequence of the thus obtained cDNA clone GTINP322A-21 contained no nucleotide sequence which coincides with the amplified differential display fragment of INP332A. Accordingly, this was considered to be a cDNA clone of other gene.

With regard to GTINP332A-21, when the expression quantity of the gene in leukocytes of IgA nephropathy patients and healthy persons was examined by the RT-PCR method described in Example 2 using primers (SEQ ID NO:105 and NO:106) prepared based on the nucleotide sequence, 4.6 times higher increase in the expression quantity was found in the IgA nephropathy patients in comparison with the case of healthy persons.

Using the cDNA moiety of GTINP322A-21 as a probe, a cDNA clone PHGTINP332A-21-28-1 was obtained by plaque hybridization of the cDNA library of IgA nephropathy patient leukocytes.

Determination of the cDNA nucleotide sequence of the clone revealed the presence of an ORF corresponding to 128 amino acids. The cDNA nucleotide sequence of PHGTINP332A-21-28-1 is shown in SEQ ID NO:6, and the amino acid sequence of the protein encoded by the ORF is shown in SEQ ID NO:39.

It was found that the amino acid sequence of the ORF has a homology with the SH2 domain of, for example, phosphatidylinositol 3,4,5-triphospho-5-phosphatase, which has a function to bind to phosphorylated tyrosine.

(6) INM063-7

To isolate a full length cDNA clone, 3 cDNA clones (INM063-7 ph5-1, INM063-7 ph4-1 and INM063-7 ph9-1) were isolated by plaque hybridization from NB-1 cDNA library.

The nucleotide sequences of these isolated cDNA clones were combined so that the nucleotide sequence the cDNA of INM063-7 composed of 4343 bp represented by SEQ ID NO:7 was determined.

The nucleotide sequence (SEQ ID NO:8) of a fragment obtained by the differential display coincided with the nucleotide sequence of a complementary strand corresponding to the 2809th to 2964th positions in SEQ ID NO:7. Based on this fact, it was assumed that the anchor primer was not annealed to the polyA sequence at the 3'-end of mRNA but to the complementary strand of the sequence wherein continuous T's were present at the 2965th to 2974th positions in SEQ ID NO:7.

An ORF composed of 343 amino acids (corresponding to the 1st to 1029th positions in SEQ ID NO:7, having the amino acid sequence of SEQ ID NO:40) was found in the nucleotide sequence of the cDNA of INM063-7 composed of 4343 bp.

As a result of comparison of the amino acid sequence of the ORF with amino acid sequence data base, it was found that it was a splicing variant of iron-regulatory protein 2 (IRP2).

Since a nucleotide sequence of 2808 bp (corresponding to the 1024th to 3832nd positions in SEQ ID NO:7) inherently considered as an intron was present in the nucleotide sequence of INM063-7, INM063-7 was assumed to be a cDNA formed by abnormal splicing.

The nucleotide sequence of a fragment whose expression was increased in the IgA nephropathy patients obtained by the differential display was present in the sequence derived from the above-described intron, which indicated that mRNA suffering from this abnormal splicing was increased in IgA nephropathy patients. The protein translated from the mRNA having this abnormal splicing was different, in amino acid sequence after the 342nd position, from the protein encoded by the authentic INP063-7 gene composed of 963 amino acids. Thus, the mRNA would probably fail to exert its inherent function.

EXAMPLE 4

Production of Polyclonal Antibody Against the Protein of the Present Invention (1) Preparation of Antigen The amino acid sequence of each protein was analyzed and parts which were considered to be suitable for peptide antigens were selected from the amino acid sequences of highly hydrophilic parts, the N-end and the C-end, and Compounds 1 to 8 (SEQ ID NO:114 to NO:121) were synthesized. Physicochemical properties of these compounds were measured by the following methods.

Mass spectrometry was carried out according to the FAB-MS method using JMS-HX110A (manufactured by Japan Electron Optics Laboratory). Amino acids were analyzed according to the method of Cohen, S. A. et al. [*Analytical Biochemistry*, 222, 19 (1994)]. Hydrolysis was carried out in hydrochloric acid vapor at 110° C. for 20 hours and the amino acid composition of a hydrolysate was analyzed using an amino acid analyzer, Waters AccQ-Tag (manufactured by Waters).

(i) Synthesis of Peptide Having the Amino Acid Sequence Represented by SEQ ID NO:114 (Compound 1)

To produce an antibody against the proteins of SEQ ID NO:37 and NO:38, a peptide having the amino acid sequence corresponding to the C-terminal 14 amino acids of these proteins was synthesized according to the following method.

In a reactor of an automatic synthesizer (manufactured by ACT), 52.1 mg of a carrier resin to which 25 µmol of $N^\alpha$-9-fluorenylmethyloxycarbonyl-L-isoleucine (hereinafter referred to as "Fmoc-Ile") had been bound (Wang Resin, manufactured by Novabiochem) was introduced, and 0.5 ml of DMF was added thereto, followed by stirring for 3 minutes. Then the solution was discarded and the following operations were carried out.

(a) To the mixture, 1 ml of a solution (hereinafter referred to as the "25% piperidine-DMF solution") obtained by 25% of piperidine was added to N,N-dimethylformamide (hereinafter referred to as "DMF") was added, followed by stirring for 2 minutes, and the solution was discarded. To the mixture, 1 ml of the 25% piperidine-DMF solution was added again, followed by stirring for 10 minutes, and the solution was discarded.

(b) To the carrier resin, 1 ml of DMF was added. After stirring for 1 minute, the solution was discarded. After repeating this operation 6 times, the resin and the reactor were washed with 0.5 ml of DMF.

Thus, a carrier resin from which 9-fluorenylmethyloxycarbonyl (hereinafter referred to as "Fmoc") had been removed and to which H-Ile had been bound was obtained.

(c) To the resulting carrier resin, 500 µl of DMF, 250 µl of an N-methylpyrrolidone (hereinafter referred to as "NMP") solution containing 0.5 M of $N^\alpha$-9-fluorenylmethyloxycarbonyl-L-aspartic acid-β-t-butyl ester [hereinafter referred to as "Fmoc-Asp(OtBu)-OH"] and 0.5 M of N-hydroxybenzotriazole (hereinafter referred to as "HOBt") monohydrate, and 125 µl of an NMP solution containing 0.5 M of N,N'-diisopropylcarbodiimide (hereinafter referred to as "DIPC") were added, followed by stirring for 10 minutes and allowing to stand for 1 minute. After repeating the cycle of stirring for 10 minutes and allowing to stand for 1 minute 4 times, the solution was discarded.

(d) To the carrier resin, 1 ml of DMF was added, followed by stirring for 1 minute, and the solution was discarded. This operation was repeated twice.

(e) To the carrier resin, 375 µl of DMF, 250 µl of an NMP solution containing 0.5 M of Fmoc-Asp(OtBu)-OH and 0.5 M of HOBt monohydrate, 250 µl of a DMF solution containing 0.5 M of 2-(1H-benzotriazol-1-yl)-1,1,3,3-tetramethyluronium hexafluorophosphate (hereinafter referred to as "HBTU"), and 125 µl of a DMF solution containing 2 M of diisopropylethylamine (hereinafter referred to as "DIEA") were added, followed by stirring for 10 minutes and allowed to stand for 1 minute. After repeating the cycle of stirring for 10 minutes and allowing to stand for 1 minute three times, the solution was discarded.

(f) To the carrier resin, 1 ml of DMF was added, followed by stirring for 1 minute, and the solution was discarded. After repeating this operation twice, the resin and the reactor were washed with 0.5 ml of DMF.

Thus, a carrier to which Fmoc-Asp(OtBu)-Ile had been bound was obtained.

After completion of the above-described step (f), the operations of (a) and (b) for removing the Fmoc groups were carried out. After removing the Fmoc groups, a condensation reaction was carried out as in the step (c) but replacing Fmoc-Asp(OtBu)-OH with $N^\alpha$-9-fluorenylmethyloxycarbonyl-O-t-butyl-L-threonine [hereinafter referred to as "Fmoc-Thr(tBu)-OH"]. After completion of the condensation reaction, the washing operation of (d) was carried out, and then a condensation reaction was carried out again as in the step (e) but replacing Fmoc-Asp(OtBu)-OH with Fmoc-Thr(tBu)-OH, followed by the washing operation of the step (f). Thus, Fmoc-Thr(tBu)-Aps(OtBu)-Ile was synthesized on the carrier.

The operations in the steps (a) to (f) were repeated by successively using, in the steps (c) and (e), $N^\alpha$-9-fluorenylmethyloxycarbonyl-$N^g$-2,2,5,7,8-pentamethylchroman-6-sulfonyl-L-arginine [hereinafter referred to as "Fmoc-Arg(Pmc)-OH"], Fmoc-Thr(tBu)-OH, $N^\alpha$-9-uorenylmethyloxycarbonyl-L-phenylalanine (hereinafter referred to as "Fmoc-Phe-OH"), Fmoc-Phe-OH, Fmoc-Thr(tBu)-OH, $N^\alpha$-9-fluorenylmethyloxycarbonyl-L-glycine (hereinafter referred to as "Fmoc-Gly-OH"), Fmoc-Asp(OtBu)-OH, $N^\alpha$-9-fluorenylmethyloxycarbonyl-L-glutamic acid-γ-t-butyl ester [hereinafter referred to as "Fmoc-Glu(Ot-Bu)-OH"], Fmoc-Arg(Pmc)-OH, $N^\alpha$-9-fluorenylmethyloxycarbonyl-$N^\epsilon$-t-butyloxycarbonyl-L-lysine [hereinafter referred to "as Fmoc-Lys(Boc)-OH"], Fmoc-Thr(tBu)-OH, $N^\alpha$-9-fluorenylmethyloxycarbonyl-L-leucine (hereinafter referred to as "Fmoc-Leu-OH"), Fmoc-Thr(tBu)-OH, $N^\alpha$-9-fluorenylmethyloxycarbonyl-L-proline (hereinafter referred to as "Fmoc-Pro-OH"), and $N^\alpha$-9-fluorenylmethyloxycarbonyl-S-trityl-L-cysteine [hereinafter referred to as "Fmoc-Cys(Trt)-OH"], and then the operations of the steps (a) and (b) for removing the Fmoc groups were carried out.

The resin thus obtained was washed successively with methanol and butyl ether and dried under reduced pressure for 12 hours to give a carrier resin to which a side chain-protected peptide had been bound. To the carrier resin, 1 ml of a mixture solution composed of 82.5% of trifluoroacetic acid (hereinafter referred to as "TFA"), 5% of thioanisole, 5% of water, 3% of ethyl methyl sulfide, 2.5% of 1,2-ethanediol and 2% of thiophenol was added, followed by allowing to stand at room temperature for 8 hours, to remove the side chain-protective group and cut out the peptide from the resin. After filtering off the resin, about 10 ml of ether was added to the resulting solution. The precipitate thus formed was collected by centrifugation and decantation to give 49.0 mg of a crude peptide. This crude product was dissolved in a 2M aqueous acetic acid solution and then purified by HPLC using a reversed phase column (CAPCELL PAK C18, 30 mm I.D.×250 mm, manufactured by Shiseido). Then it was eluted by the linear concentration gradient method, wherein a 90% aqueous acetonitrile solution containing 0.1% of TFA was added to a 0.1% aqueous TFA solution, followed by detection at 220 nm to give a fraction containing Compound 1. This fraction was freeze-dried to give 18.0 mg of Compound 1.

Mass spectrometry [FABMS]; m/z=1797.4 (M+H$^+$)
Amino acid analysis: Asx 2.1(2), Glx 1.1(1), Gly 1.0(1), Arg 1.8(2), Thr 2.0(2), Pro 0.9(1), Cys 1.3(1), Lys 1.0(1), Ile 1.0(1), Leu 1.0(1), Phe 1.9(2)

(ii) Synthesis of Peptide Having the Amino Acid Sequence Represented by SEQ ID NO:115 (Compound 2)

To produce an antibody against the proteins of SEQ ID NO:37 and NO:38, a peptide having the amino acid sequence corresponding to the 15 amino acids at the 73rd to 87th positions of these proteins was synthesized according to the following method.

As a starting material, 45.5 mg of a carrier resin having 25 µmol of Fmoc-NH bound thereto (Rink Amide MBHA Resin, manufactured by Novabiochem) was used, and condensation was successively carried out using Fmoc-Glu(OtBu)-OH, Fmoc-Leu-OH, Fmoc-Arg(Pmc)-OH, Fmoc-Glu(OtBu)-OH, Fmoc-Arg(Pmc)-OH, Fmoc-Lys(Boc)-OH, $N^\alpha$-9-fluorenylmethyloxycarbonyl-O-t-butyl-L-serine [hereinafter referred to as "Fmoc-Ser(tBu)-OH"], Fmoc-Lys(Boc)-OH, $N^\alpha$-9-fluorenylmethyloxycarbonyl-$N^\gamma$-trityl-L-asparagine [hereinafter referred to as "Fmoc-Asn(Trt)-OH"], Fmoc-Phe-OH, Fmoc-Lys(Boc)-OH, Fmoc-Glu(OtBu)-OH, Fmoc-Leu-OH, Fmoc-Phe-OH, Fmoc-Ser(tBu) and Fmoc-Cys(Trt)-OH in the same manner as in (1)-(i). Removing of the Fmoc groups, washing and drying and were carried out to give a carrier resin to which a side chain-protected peptide had been bound. The side chain-protective group was cleaved and the peptide was cut out from the resin in the same manner as in (1)-(i) to give 67.1 mg of a crude peptide. After purifying by HPLC using a reversed phase column, 30.8 mg of Compound 2 was obtained.

Mass spectrometry [FABMS]; m/z=2013.1 (M+H⁺)
Amino acid analysis: Asx 1.0(1), Ser 1.8(2), Glx 3.2(3), Arg 1.9(2), Cys 1.3(1), Lys 3.0(3), Leu 1.9(2), Phe 2.0(2)

(iii) Synthesis of Peptide Having the Amino Acid Sequence Represented by SEQ ID NO:116 (Compound 3)

To produce an antibody against the proteins of SEQ ID NO:37 and NO:38, a peptide having the amino acid sequence corresponding to the 14 amino acids at the 104th to 116th positions of these proteins was synthesized according to the following method.

As a starting material, 45.5 mg of a carrier resin to which 25 μmol of Fmoc-NH was bound (Rink Amide MBHA Resin, manufactured by Novabiochem) was used, and condensation was successively carried out using Fmoc-Gly-OH, $N^{\alpha}$-9-fluorenylmethyloxycarbonyl-L-valine [hereinafter referred to as "Fmoc-Val-OH"], Fmoc-Lys(Boc)-OH, $N^{\alpha}$-9-fluorenylmethyloxycarbonyl-$N^{ind}$-t-butyloxycarbonyl-L-tryptophane [hereinafter referred to as "Fmoc-Trp(Boc)-OH"], Fmoc-Lys(Boc)-OH, Fmoc-Glu(OtBu)-OH, Fmoc-Phe-OH, Fmoc-Glu(OtBu)-OH, Fmoc-Gly-OH, Fmoc-Ser(tBu)-OH, Fmoc-Trp(Boc)-OH, $N^{\alpha}$-9-fluorenylmethyloxycarbonyl-$N^{im}$-trityl-L-histidine [hereinafter referred to as "Fmoc-His(Trt)-OH"], Fmoc-Glu(OtBu)-OH, $N^{\alpha}$-9-fluorenylmethyloxycarbonyl-L-alanine (hereinafter referred to as "Fmoc-Ala-OH") and Fmoc-Cys(Trt)-OH in the same manner as in (1)-(i). Removing of the Fmoc groups, washing and drying were carried out to give a carrier resin to which a side chain-protected peptide had been bound. To the carrier resin, 1 ml of a mixture solution composed of TFA containing 5 mg/ml of 2-methylindole (90%), thioanisole (5%) and 1,2-ethanediol (5%) was added, followed by allowing to stand at room temperature for 2 hours to cleave the side chain-protective group and cutting out the peptide from the resin. Then, 50.6 mg of a crude peptide was obtained in the same manner as in (1)-(i). It was purified by HPLC using a reversed phase column to give 6.6 mg of Compound 3.

Mass spectrometry [FABMS]; m/z=1792.5 (M+H⁺)
Amino acid analysis: Ser 1.0(1), Glx 3.0(3), Gly 2.2(2), His 0.8(1), Ala 0.8(1), Cys 1.1(1), Val 1.1(1), Lys 2.1(2), Phe 1.1(1), Trp: not analyzed (iv) Synthesis of Peptide Having the Amino Acid Sequence Represented by SEQ ID NO:117 (Compound 4)

To produce an antibody against the protein of SEQ ID NO:34, a peptide having the amino acid sequence corresponding to the C-terminal 15 amino acids of this protein was synthesized according to the following method.

As a starting material, 49.0 mg of a carrier resin to which 25 μmol of Fmoc-Phe was bound (Wang Resin, manufactured by Novabiochem) was used, and condensation was successively carried out using Fmoc-Lys(Boc)-OH, Fmoc-Gly-OH, Fmoc-Phe-OH, Fmoc-His(Trt)-OH, Fmoc-Leu-OH, Fmoc-Ile-OH, Fmoc-Leu-OH, Fmoc-Ser(tBu)-OH, Fmoc-Val-OH, Fmoc-Arg(Pmc)-OH, Fmoc-Lys(Boc)-OH, Fmoc-Asp(OtBu)-OH, Fmoc-Ile-OH, Fmoc-Glu(OtBu)-OH and Fmoc-Cys(Trt)-OH in the same manner as in (1)-(i). Removing of the Fmoc groups, washing and drying were carried out to give a carrier resin to which a side chain-protected peptide had been bound. The side chain-protective group was cleaved and the peptide was cut out from the resin in the same manner as in (1)-(i) to give 41.2 mg of a crude peptide. It was purified by HPLC with the use of a reversed phase column, 14.6 mg of Compound 4 was obtained.

Mass spectrometry [FABMS]; m/z=1905.8 (M+H⁺)
Amino acid analysis: Asx 1.0(1), Ser 0.9(1), Glx 1.0(1), Gly 1.1(1), His 1.1(1), Arg 0.9(1), Cys 1.3(1), Val 1.0(1), Lys 2.1(2), Ile 1.8(2), Leu 1.9(2), Phe 2.2(2)

(v) Synthesis of Peptide Having the Amino Acid Sequence Represented by SEQ ID NO:118 (Compound 5)

To produce an antibody against the protein of SEQ ID NO:35, a peptide having the amino acid sequence corresponding to the C-terminal 14 amino acids of this protein was synthesized according to the following method.

As a starting material, 42.2 mg of a carrier resin to which 25 μmol of Fmoc-Ser(tBu) had been bound (Wang Resin, manufactured by Novabiochem) was used, and condensation was carried out using Fmoc-Ser(tBu)-OH, Fmoc-Leu-OH, Fmoc-Leu-OH, Fmoc-Ser(tBu)-OH, Fmoc-Glu(OtBu)-OH, Fmoc-Gly-OH, Fmoc-Thr(tBu)-OH, Fmoc-Lys(Boc)-OH, Fmoc-Arg(Pmc)-OH, Fmoc-Lys(Boc)-OH, $N^{\alpha}$-9-fluorenylmethyloxycarbonyl-L-methionine (hereinafter referred to as "Fmoc-Met-OH"), Fmoc-Leu-OH, Fmoc-Arg(Pmc)-OH and Fmoc-Cys(Trt)-OH in the same manner as in (1)-(i). Removing of the Fmoc groups, washing and drying were carried out to give a carrier resin to which a side chain-protected peptide had been bound. The side chain-protective group was cleaved and the peptide was cut out from the resin in the same manner as in (1)-(i) to give 48.4 mg of a crude peptide. It was purified by HPLC using a reversed phase column to give 19.0 mg of Compound 5.

Mass spectrometry [FABMS]; m/z=1708.9 (M+H⁺)
Amino acid analysis: Ser 2.8(3), Glx 1.1(1), Gly 1.1(1), Arg 2.1(2), Thr 1.0(1), Cys 1.3(1), Met 0.4(1), Lys 2.1(2), Leu 3.0(3)

(vi) Synthesis of Peptide Having the Amino Acid Sequence Represented by SEQ ID NO:119 (Compound 6)

To produce an antibody against the protein of SEQ ID NO:40, a peptide having the amino acid sequence corresponding to the C-terminal 13 amino acids of this protein was synthesized according to the following method.

As a starting material, 42.4 mg of a carrier resin to which 25 μmol of Fmoc-Ser(tBu) had been bound (Wang Resin, manufactured by Novabiochem), and condensation was successively carried out using Fmoc-Val-OH, Fmoc-Lys(Boc)-OH, Fmoc-Thr(tBu)-OH, Fmoc-Ile-OH, Fmoc-Gly-OH, Fmoc-Leu-OH, Fmoc-Val-OH, Fmoc-Val-OH, Fmoc-Asp(OtBu)-OH, Fmoc-Ile-OH, Fmoc-Ser(tBu)-OH, Fmoc-Thr(tBu)-OH and Fmoc-Cys(Trt)-OH in the same manner as in (1)-(i). Removing of the Fmoc groups, washing and drying were carried out to give a carrier resin to which a side chain-protected peptide had been bound. To the carrier resin, 1 ml of a mixture solution composed of 90% of TFA, 5% of thioanisole and 5% of 1,2-ethanediol was added, followed by allowing to stand at room temperature for 2 hours, to remove the side chain-protective group and cut out from the resin. Then 32.8 mg of a crude peptide was obtained in the same manner as in (1)-(i) and purified by HPLC using a reversed phase column to give 11.0 mg of Compound 6.

Mass spectrometry [FABMS]; m/z 1434.7 (M+H⁺)
Amino acid analysis: Asx 1.1(1), Ser 1.9(2), Gly 1.1(1), Thr 2.0(2), Cys 1.2(1), Val 2.1(3), Lys 1.1(1), Ile 2.3(2), Leu 1.1(1)

(vii) Synthesis of Peptide Having the Amino Acid Sequence Represented by SEQ ID NO:120 (Compound 7)

To produce an antibody against the protein of SEQ ID NO:39, a peptide having the amino acid sequence corresponding to 15 amino acids at the 65th to 79th positions of this protein was synthesized according to the following method.

As a starting material, 45.5 mg of a carrier resin to which 25 μmol of Fmoc-NH had been bound (Rink Amide Resin, manufactured by Novabiochem) was used, and condensation was successively carried out using Fmoc-Lys(Boc)-OH, Fmoc-Arg(Pmc)-OH, Fmoc-Phe-OH, $N^\alpha$-9-fluorenylmethyloxycarbonyl-O-t-butyl-L-tyrosine [hereinafter referred to as "Fmoc-Tyr(tBu)-OH"], Fmoc-Arg (Pmc)-OH, Fmoc-Lys(Boc)-OH, Fmoc-His(Trt)-OH, Fmoc-Val-OH, Fmoc-Gly-OH, Fmoc-Pro-OH, $N^\alpha$-9-fluorenylmethyloxycarbonyl-L-alanine (hereinafter referred to as "Fmoc-Ala-OH"), Fmoc-Thr(tBu)-OH, Fmoc-Glu (OtBu)-OH, Fmoc-Ala-OH, Fmoc-Ser(tBu) and Fmoc-Cys (Trt)-OH in the same manner as in (1)-(i). Removing of the Fmoc groups, washing and drying were carried out to give a carrier resin to which a side chain-protected peptide had been bound. Then the side chain-protective group was cleaved and the peptide was cut out from the resin in the same manner as in (1)-(i) to give 42.4 mg of a crude peptide. The crude peptide was purified by HPLC using a reversed phase column to give 12.1 mg of Compound 7.

Mass spectrometry [FABMS]; m/z=1849.7 (M+H$^+$)
Amino acid analysis: Ser 0.9(1), Glx 1.0(1), Gly 1.0(1), His 0.7(1), Arg 2.0(2), Thr 0.9(1), Ala 1.9(2), Pro 1.0(1), Cys 1.4(1), Tyr 1.7(1), Val 0.7(1), Lys 2.1(2), Phe 1.1(1)

(viii) Synthesis of Peptide Having the Amino Acid Sequence Represented by SEQ ID NO:121 (Compound 8)

To produce an antibody against the protein of SEQ ID NO:36, a peptide having the amino acid sequence corresponding to the C-terminal 15 amino acids of this protein was synthesized according to the following method.

As a starting material, 61.0 mg of a carrier resin to which 25 μmol of H-Pro had been bound (Chlorotrityl Resin, manufactured by Novabiochem) was used, and the resin was washed with 1 ml of dichloromethane. Then, condensation was successively carried out using Fmoc-Tyr(tBu)-OH, Fmoc-Asn(Trt)-OH, Fmoc-Leu-OH, Fmoc-Val-OH, Fmoc-Asn (Trt)-OH, Fmoc-Gly-OH, Fmoc-Leu-OH, Fmoc-Leu-OH, $N^\alpha$-9-fluorenylmethyloxycarbonyl-$N^\epsilon$-trityl-L-glutamine [hereinafter referred to "Fmoc-Gln(Trt)-OH"], Fmoc-Lys(Boc)-OH, Fmoc-Glu(OtBu)-OH, Fmoc-Thr(Bu)-OH, Fmoc-Ile-OH, Fmoc-Lys-(Boc)-OH and Fmoc-Cys (Trt)-OH in the same manner as in (1)-(i), except for the synthesis started from the step (c) in (1)-(i). Removing of the Fmoc groups, washing and drying were carried out to give a carrier resin to which a side chain-protected peptide had been bound. The side chain-protective group was cleaved and the peptide was cut out from the resin in the same manner as in I-6 to give 53.1 mg of a crude peptide in the same manner as in (1)-(i). The crude was purified by HPLC using a reversed phase column to give 23.4 mg of Compound 8.

Mass spectrometry [FABMS]; m/z=1833.6 (M+H$^+$)
Amino acid analysis: Asx 2.1(2), Glx 2.1(2), Gly 1.1(1), Thr 0.9(1), Pro 1.0(1), Cys 1.4(1), Tyr 1.0(1), Val 0.9(1), Lys 1.9(2), Ile 1.0(1), Leu 2.9(3)

(2) Preparation of Immunogen

To enhance immunogenicity, conjugates of Compounds 1 to 8 obtained in the above (1) with KLH (manufactured by Calbiochem) were prepared in the following manner and employed as antigens.

Namely, KLH was dissolved in PBS to give a concentration of 10 mg/ml, and 25 mg/ml of MBS (manufactured by Nakalai Tesque) at 1/10 volume was added dropwise thereto, followed by reaction under stirring for 30 minutes.

The unreacted MBS was removed using Sephadex G-25 column which had been preliminarily equilibrated with PBS.

To 0.1 M sodium phosphate buffer (pH 7.0) in which 1 mg of each of Compounds 1 to 8 had been dissolved, 2.5 mg of the resulting KLH-MB was added and mixed, followed by reaction under stirring at room temperature for 3 hours.

After completion of the reaction, the reaction solution was dialyzed against PBS.

(3) Immunization of Animals and Preparation of Polyclonal Antibodies

To female (SD) rats of 5 weeks of age, 100 μg of the conjugate of each compound with KLH as prepared in the above (2) was administered, together with 2 mg of an aluminum gel and $1 \times 10^9$ pertussis vaccine cells (manufactured by Chiba Serum Institute). Two weeks after the administration, 100 μg of the conjugate was administered once a week 4 times in total. The blood of each animal was collected from the venous plexus of the eyeground and the serum antibody titer was examined by the enzyme immunoassay. The whole blood was collected from rats showing an enough titer to obtain the serum.

(4) Enzyme Immunoassay

As the antigen for the assay, conjugates of respective compounds obtained in the above (1) with thyroglobulin (hereinafter referred to as "THY") were used. The production was carried out according to the above (2), except that MBS was replaced with SMCC (manufactured by Sigma) as a crosslinking agent. Into a 96-well EIA plate (manufactured by Greiner), 10 μg/ml of each conjugate thus prepared was poured at 50 μl/well and allowed to be stand for adsorption at 4° C. overnight. After washing, 1% BSA-PBS was added at 100 μl/well and reaction was carried out at room temperature for 1 hour to block the remaining active groups. The 1% BSA-PBS was discarded, and the immunized rat antiserum was poured at 50 μl/well, followed by reaction for 2 hours. After washing with a solution of PBS to which 0.05% Tween had been added (hereinafter referred to as "0.05% Tween-PBS"), peroxidase-labeled rabbit anti-rat immunoglobulin (manufactured by Dako) was added at 50 μl/well, followed by reaction at room temperature for 1 hour. After washing with 0.05% Tween-PBS, color development was performed using an ABTS substrate solution [ammonium 2,2-adinobis(3-ethylbenzothiazole-6-sulfonate)], and the absorbance (OD) at 415 nm was measured with a plate reader (E-max, manufactured by Wako Pure Chemical Industries).

Figure 2:
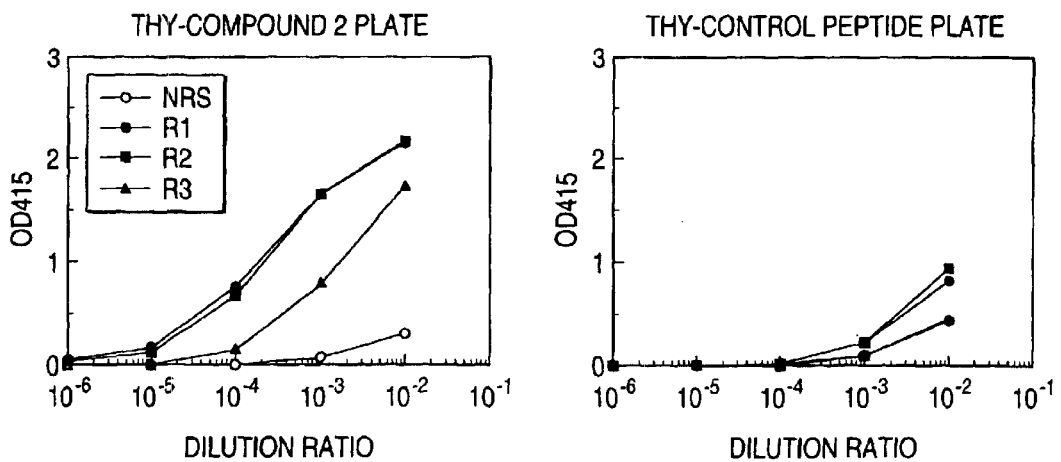
FIG. 2 is a graph showing the binding reactivity of rat antisera, which were obtained by immunizing rats with a conjugate of a peptide (Compound 2) having the amino acid sequence represented by SEQ ID NO:115 with KLH, to Compound 2 examined by the enzyme immunoassay. The binding reactivity to Compound 2 is shown in the left, while the binding reactivity to a control peptide is shown in the right. R1 to R3 and NRS show antisera of 3 rats immunized with Compound 2 and a normal rat serum, respectively.
Figure 5:
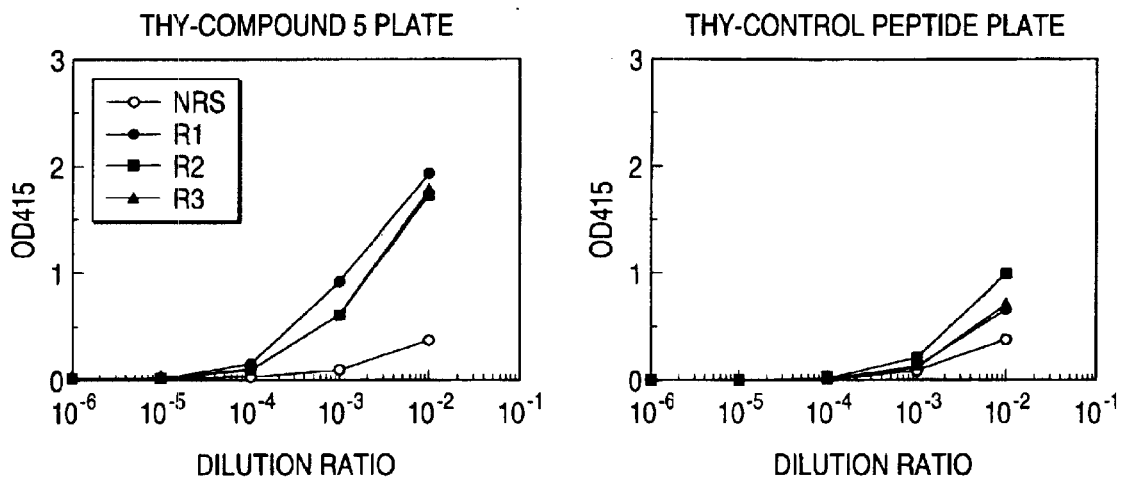
FIG. 5 is a graph showing the binding reactivity of rat antisera, which were obtained by immunizing rats with a conjugate of a peptide (Compound 5) having the amino acid sequence represented by SEQ ID NO:118 with KLH, to Compound 5 examined by the enzyme immunoassay. The binding reactivity to Compound 5 is shown in the left, while the binding reactivity to a control peptide is shown in the right. R1 to R3 and NRS show antisera of 3 rats immunized with Compound 5 and a normal rat serum, respectively.
Figure 6:
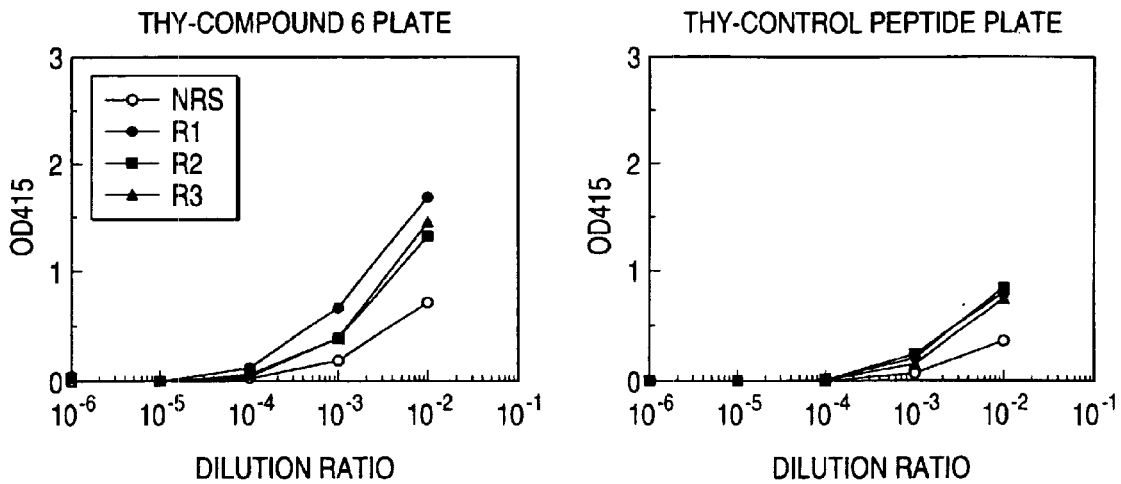
FIG. 6 is a graph showing the binding reactivity of rat antisera, which were obtained by the immunization with a conjugate of a peptide (Compound 6) having the amino acid sequence represented by SEQ ID NO:119 with KLH, to Compound 6 examined by the enzyme immunoassay. The binding reactivity to Compound 6 is shown in the left, while the binding reactivity to a control peptide is shown in the right. R1 to R3 and NRS show antisera of 3 rats immunized with Compound 6 and a normal rat serum, respectively.
Figure 7:
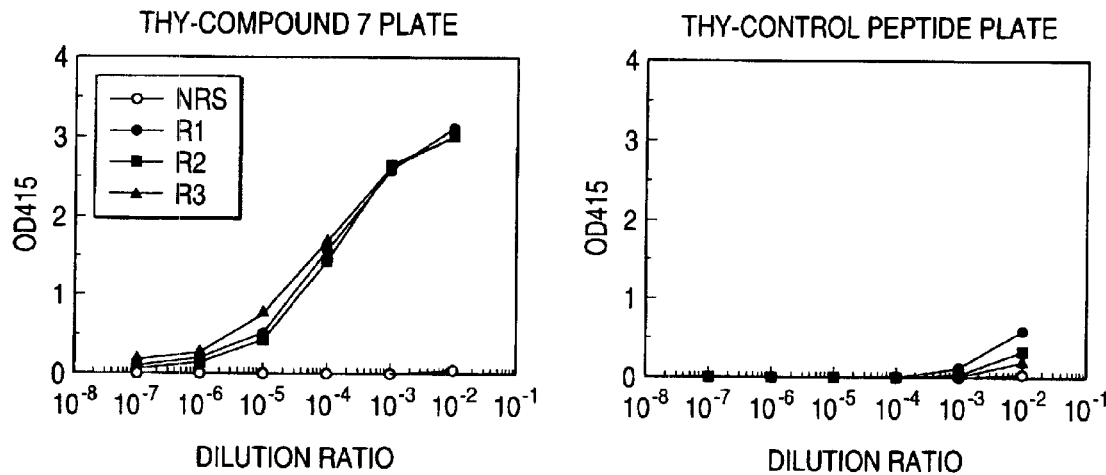
FIG. 7 is a graph showing the binding reactivity of rat antisera, which were obtained by immunizing rats with a conjugate of a peptide (Compound 7) having the amino acid sequence represented by SEQ ID NO:120 with KLH, to Compound 7 examined by the enzyme immunoassay. The binding reactivity to Compound 7 is shown in the left, while the binding reactivity data to a control peptide is shown in the right. R1 to R3 and NRS show antisera of 3 rats immunized with Compound 7 and a normal rat serum, respectively.
Figure 8:
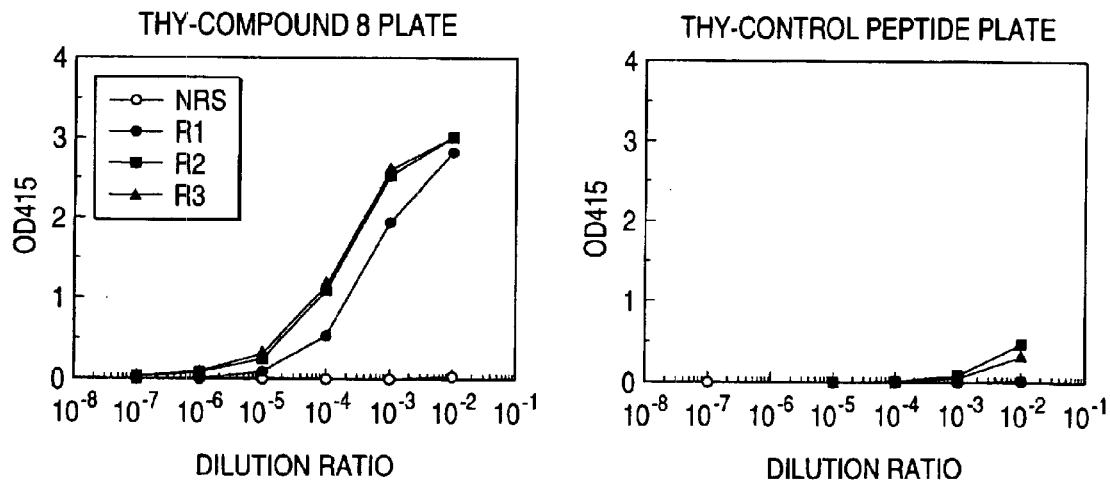
FIG. 8 is a graph showing the binding reactivity of rat antisera, which were obtained by immunizing rats with a conjugate of a peptide (Compound 8) having the amino acid sequence represented by SEQ ID NO:121 with KLH, to Compound 8 examined by the enzyme immunoassay. The binding reactivity to Compound 8 is shown in the left, while the binding reactivity to a control peptide is shown in the right. R1 to R3 and NRS show antisera of 3 rats immunized with Compound 8 and a normal rat serum, respectively.

The results are shown in FIGS. 1 to 8. Each of these antisera showed a specific reactivity to the compound used as the immunogen.

While the invention has been described in detail and with reference to specific embodiments thereof, it will be apparent to one of skilled in the art that various changes and modifications can be made therein without departing from the spirit and scope thereof.

What is claimed is:

1. An isolated DNA comprising a nucleotide sequence of SEQ ID NO:7.

2. An isolated DNA consisting of a nucleotide sequence of SEQ ID NO:45.

3. An isolated DNA consisting of a nucleotide sequence of SEQ ID NO:46.

4. A method for inhibiting transcription of an IgA nephropathy-related gene or translation of mRNA of an IgA nephropathy-related gene using the DNA according to claims 2 or 3.

5. A method for detecting mRNA of an IgA nephropathy-related gene using the DNA according to any one of claims 1, 2 or 3.

6. An isolated DNA encoding a protein comprising an amino acid sequence of SEQ ID NO:40.

7. A recombinant DNA obtained by inserting the DNA according to claim 6 into a vector.

8. A transformant obtained by introducing the recombinant DNA according to claim 7 into a host cell.

9. A method for producing a protein comprising an amino acid sequence of SEQ ID NO:40, comprising:

culturing the transformant according to claim 8 in a medium to produce and accumulate said protein in the culture; and recovering said protein form the resulting culture.

10. A method for diagnosing IgA nephropathy comprising:

(a) detecting a mRNA corresponding to the nucleotide sequence of SEQ ID NO:7 in leukocytes of a subject and healthy person using a DNA comprising a nucleotide sequence selected from the group of nucleotide sequences consisting of SEQ ID NO:7, 45, 46, a nucleotide sequence identical to continuous 5 to 60 residues in a nucleotide sequence represented by SEQ ID NO:7, and a nucleotide sequence complementary to continuous 5 to 60 residues in a nucleotide sequence of SEQ ID NO:7; and (b) diagnosing IgA nephropathy in the subject based on an increased level of said mRNA in leukocytes of a subject as compared with those of healthy persons.

* * * * *

UNITED STATES PATENT AND TRADEMARK OFFICE
CERTIFICATE OF CORRECTION

PATENT NO. : 6,962,984 B2
APPLICATION NO. : 09/730559
DATED : November 8, 2005
INVENTOR(S) : Tetsuyoshi Ishiwata et al.

It is certified that error appears in the above-identified patent and that said Letters Patent is hereby corrected as shown below:

Title page,
Item [56], References Cited, OTHER PUBLICATIONS,
"Genbank entry M58511," reference, "iron-respnsive" should read
-- iron-responsive --; and "Plant, Physiol," should read -- Plant Physiol, --;
"Lai Kar Neng, et al.," reference, "factor-βin" should read -- factor-B in --;
"International ," should read -- International, --; and
"Ichinose, et al.," reference, "crytokine" should read -- cytokine --.

Column 6,
Line 33, "Biotechnology," should read -- Biotechnology, --.

Column 10,
Line 2, "*Brevibacterium flavunm*" should read -- *Brevibacterium flavum* --; and
Line 24, "MF a1 promoter" should read -- MF α1 promoter --.

Column 12,
Line 47, "by" should read -- be --.

Column 20,
Line 29, "DNTP" should read -- dNTP --;
Line 30, "(DATP," should read -- (dATP, --; and
Line 42, "DNTP," should read -- dNTP, --.

Column 21,
Line 22, "DNTP," should read -- dNTP, --.

Column 23,
Line 59, "5"-RACE" should read -- 5'-RACE --.

Column 26,
Line 25, "DNTP" should read -- dNTP --.

Column 28,
Line 27, "INP303A phi-3" should read -- INP303A ph1-3 --.

Column 31,
Line 20, "to" should read -- to be --.

Column 34,
Line 66, "and" (second occurrence) should be deleted.

UNITED STATES PATENT AND TRADEMARK OFFICE
CERTIFICATE OF CORRECTION

PATENT NO.         : 6,962,984 B2
APPLICATION NO. : 09/730559
DATED              : November 8, 2005
INVENTOR(S)       : Tetsuyoshi Ishiwata et al.

It is certified that error appears in the above-identified patent and that said Letters Patent is hereby corrected as shown below:

<u>Column 38,</u>
Line 39, "be" should be deleted; and
Line 64, "of" should be deleted.

<u>Column 112,</u>
Line 4, "form" should read -- from --; and
Line 9, "healthy" should read -- a healthy --.

Signed and Sealed this

Twelfth Day of September, 2006

JON W. DUDAS
*Director of the United States Patent and Trademark Office*